(12) United States Patent
Ishiduka et al.

(10) Patent No.: US 7,713,679 B2
(45) Date of Patent: May 11, 2010

(54) RESIST COMPOSITION, METHOD OF FORMING RESIST PATTERN, NOVEL COMPOUND, AND ACID GENERATOR

(75) Inventors: Keita Ishiduka, Kawasaki (JP); Yoshiyuki Utsumi, Kawasaki (JP); Akiya Kawaue, Kawasaki (JP); Takehiro Seshimo, Kawasaki (JP); Hideo Hada, Kawasaki (JP)

(73) Assignee: Tokyo Ohka Kogyo Co., Ltd.

( * ) Notice: Subject to any disclaimer, the term of this patent is extended or adjusted under 35 U.S.C. 154(b) by 0 days.

(21) Appl. No.: 12/251,327

(22) Filed: Oct. 14, 2008

(65) Prior Publication Data

US 2009/0104563 A1 Apr. 23, 2009

(30) Foreign Application Priority Data

Oct. 22, 2007 (JP) ............................. 2007-274340
Feb. 28, 2008 (JP) ............................. 2008-048103

(51) Int. Cl.
G03F 7/004 (2006.01)

(52) U.S. Cl. .................. 430/270.1; 430/919; 430/920; 430/921; 430/922; 562/109; 562/112; 562/114

(58) Field of Classification Search ............. 430/270.1, 430/919, 920, 921, 922; 562/109, 112, 114
See application file for complete search history.

(56) References Cited

U.S. PATENT DOCUMENTS

| 5,945,517 | A | 8/1999 | Nitta et al. |
| 6,153,733 | A | 11/2000 | Yukawa et al. |
| 6,830,871 | B2 * | 12/2004 | Kanna et al. ............. 430/270.1 |
| 7,323,287 | B2 | 1/2008 | Iwai et al. |

| 2003/0194650 | A1 * | 10/2003 | Kanna et al. ............. 430/285.1 |
| 2005/0164123 | A1 * | 7/2005 | Mizutani ............. 430/270.1 |

FOREIGN PATENT DOCUMENTS

| JP | HEI9-208554 | 8/1997 |
| JP | HEI-11-035551 | 2/1999 |
| JP | HEI-11-035552 | 2/1999 |
| JP | HEI-11-035573 | 2/1999 |
| JP | HEI-11-322707 | 11/1999 |
| JP | 2003-241385 | 8/2003 |
| WO | WO 2004/074242 A2 | 9/2004 |

* cited by examiner

*Primary Examiner*—John S Chu
(74) *Attorney, Agent, or Firm*—Knobbe, Martens, Olson & Bear, LLP

(57) ABSTRACT

There is provided a compound represented by a general formula (B1-1) shown below, an acid generator composed of the above compound, a resist composition containing an acid generator composed of the above compound, and a method of forming a resist pattern:

[Chemical Formula 1]

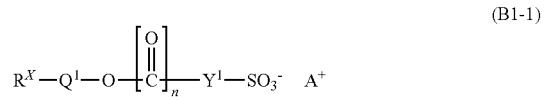

(B1-1)

(wherein $R^X$ represents a hydrocarbon group which may contain a substituent group; $Q^1$ represents an alkylene group of 1 to 12 carbon atoms which may contain a substituent group, or a single bond; n represents an integer of 0 or 1; $Y^1$ represents an alkylene group of 1 to 4 carbon atoms, or a fluorinated alkylene group of 1 to 4 carbon atoms; and $A^+$ represents an organic cation which contains a nitrogen atom).

11 Claims, No Drawings

RESIST COMPOSITION, METHOD OF FORMING RESIST PATTERN, NOVEL COMPOUND, AND ACID GENERATOR

TECHNICAL FIELD

The present invention relates to a resist composition, a method of forming a resist pattern using the resist composition, a novel compound suitable as an acid generator for the resist composition, and the acid generator.

This application claims priority from Japanese Patent Application No. 2007-274340 filed on Oct. 22, 2007, and Japanese Patent Application No. 2008-048103 filed on Feb. 28, 2008, the disclosure of which is incorporated by reference herein.

BACKGROUND ART

Lithography techniques include processes in which, for example, a resist film formed from a resist material is formed on top of a substrate, the resist film is selectively exposed with irradiation such as light, an electron beam or the like through a mask in which a predetermined pattern has been formed, and then a developing treatment is conducted, thereby forming a resist pattern of the prescribed shape in the resist film. Resist materials in which the exposed portions change to become soluble in a developing liquid are termed positive materials, whereas resist materials in which the exposed portions change to become insoluble in the developing liquid are termed negative materials.

In recent years, in the production of semiconductor elements and liquid crystal display elements, advances in lithography techniques have led to rapid progress in the field of miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are starting to be introduced in mass production of semiconductor elements. Furthermore, research is also being conducted into lithography techniques that use $F_2$ excimer lasers, electron beams (EB), extreme ultraviolet radiation (EUV) and X-rays.

Resist materials are required to have lithography properties such as high sensitivity to the aforementioned light source and enough resolution to reproduce patterns with very fine dimensions. As resist materials which fulfill the aforementioned requirements, there is used a chemically-amplified resist containing a base resin that displays changed alkali solubility under action of acid, and an acid generator that generates acid upon exposure. For example, a chemically-amplified positive resist includes a resin in which the alkali solubility increases under action of an acid as a base resin and an acid generator, and when an acid is generated from the acid generator upon exposure in the formation of a resist pattern, the exposed portions are converted to a soluble state in an alkali developing solution.

Until recently, polyhydroxystyrene (PHS) or derivative resins (PHS-based resins) in which the hydroxyl groups have been protected with acid dissociable, dissolution inhibiting groups, which exhibit a high degree of transparency relative to KrF excimer laser (248 nm), have been used as the base resin of chemically-amplified resists. However, because PHS-based resins contain aromatic rings such as benzene rings, their transparency is inadequate for light with a wavelength shorter than 248 nm, such as light of 193 nm. Accordingly, chemically-amplified resists that use a PHS-based resin as the base resin have a disadvantage in that they have low resolution in processes that use, for example, light of 193 nm. As a result, resins (acrylic resins) that contain structural units derived from (meth)acrylate esters within the main chain are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl(meth)acrylate, are mainly used (for example, see Patent Document 1).

Here, the term "(meth)acrylate ester" is a generic term that includes either or both of the acrylate ester having a hydrogen atom bonded with the α-position and the methacrylate ester having a methyl group bonded with the α-position. The term "(meth)acrylate" is a generic term that includes either or both of the acrylate having a hydrogen atom bonded with the α-position and the methacrylate having a methyl group bonded with the α-position. The term "(meth)acrylic acid" is a generic term that includes either or both of the acrylic acid having a hydrogen atom bonded with the α-position and the methacrylic acid having a methyl group bonded with the α-position.

As an acid generator used in a chemically-amplified resist, a large variety of acid generators are proposed, and examples thereof include onium salt-based acid generators such as iodonium salts and sulfonium salts.

[Patent Document 1]

Japanese Unexamined Patent Application, First Publication No. 2003-241385.

DISCLOSURE OF THE INVENTION

Problems to be Solved by the Invention

As an anion moiety of the onium salt-based acid generators described above, a perfluoroalkylsulfonate ion has generally been used. It is considered that a perfluoroalkyl chain included in such an anion moiety be preferably a long chain in order to suppress the diffusion of an acid after exposure. However, a perfluoroalkyl chain of 6 to 10 carbon atoms is persistent (hardly-degradable), therefore a nonafluorobutane sulfonate ion or the like has been used instead, because it can be handled more safely in terms of bioaccumulation potential. For these reasons, a novel compound more suitable as an acid generator for a resist composition is required.

The present invention takes the above circumstances into consideration, with an object of providing a novel compound suitable as an acid generator for a resist composition, an acid generator, a resist composition, and a method of forming a resist pattern.

Means for Solving the Problems

To achieve the above object, the present invention employs the following constitutions.

A first aspect of the present invention is a resist composition including a base component (A) which displays changed solubility in an alkali developing solution under action of acid, and an acid generator component (B) which generates an acid upon exposure, wherein the acid generator component (B) includes an acid generator (B1) composed of the compound represented by a general formula (B1-1) shown below.

[Chemical Formula 1]

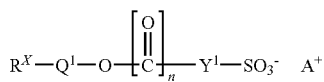
(B1-1)

(wherein, $R^X$ represents a hydrocarbon group which may contain a substituent group; $Q^1$ represents an alkylene group of 1 to 12 carbon atoms which may contain a substituent group, or a single bond; n represents an integer of 0 or 1; $Y^1$ represents an alkylene group of 1 to 4 carbon atoms or a fluorinated alkylene group of 1 to 4 carbon atoms; and $A^+$ represents an organic cation which contains a nitrogen atom.)

A second aspect of the present invention is a method of forming a resist pattern on a substrate by using a resist composition described in the first aspect of the present invention; exposing the resist film; and developing the resist film with an alkali to form a resist pattern.

A third aspect of the present invention is a compound represented by a general formula (B1-1) shown below (hereinafter, referred to as compound (B1)).

[Chemical Formula 2]

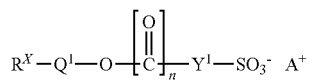
(B1-1)

(wherein, $R^X$ represents a hydrocarbon group which may contain a substituent group; $Q^1$ represents an alkylene group of 1 to 12 carbon atoms which may contain a substituent group, or a single bond; n represents an integer of 0 or 1; $Y^1$ represents an alkylene group of 1 to 4 carbon atoms or a fluorinated alkylene group of 1 to 4 carbon atoms; and $A^+$ represents an organic cation which contains a nitrogen atom.)

A fourth aspect of the present invention is an acid generator composed of the compound (B1) described in the third aspect.

In the present specification and claims, the term "alkyl group" is a concept containing a linear, branched, and cyclic monovalent saturated hydrocarbon group, unless another specific definition is provided.

The term "alkylene group" is a concept containing a linear, branched, and cyclic bivalent saturated hydrocarbon group, unless another definition is particularly provided.

The term "exposure" is used as a general concept involving irradiation with any form of radiation.

EFFECTS OF THE INVENTION

According to the present invention, there can be provided a novel compound useful as an acid generator for a resist composition, an acid generator, a resist composition, and a method of forming a resist pattern.

BEST MODE FOR CARRYING OUT THE INVENTION

Compound (B1)

Firstly, the compound (B1) according to the third aspect of the present invention will be described below. The compound (B1) is represented by the above general formula (B1-1).

In the formula (B1-1), $R^X$ represents a hydrocarbon group which may contain a substituent group.

Here, the term "may contain a substituent group" described above means that a part of or all of hydrogen atoms, or a part of carbon atoms in the hydrocarbon group may be substituted with substituent groups (atoms or groups other than the hydrogen atoms or carbon atoms). The number of the substituent groups in $R^X$ may be one, or two or more.

The hydrocarbon group for $R^X$ may be an aromatic hydrocarbon group or an aliphatic hydrocarbon group.

Here, the term "aliphatic" in the present specification is a relative concept used in relation to the term "aromatic", and defines a group or compound or the like that contains no aromaticity.

The aromatic hydrocarbon group for $R^X$ may be a group containing an aromatic hydrocarbon ring whose ring structure consists of carbon atoms, or may be a group containing an aromatic heterocyclic ring which includes a hetero atom other than carbon atoms in the ring structure of the aromatic ring. Specific examples thereof include aryl groups in which one hydrogen atom is removed from an aromatic hydrocarbon ring, such as a phenyl group, a biphenyl group, a fluorenyl group, a naphthyl group, an anthryl group, and a phenanthryl group; and arylalkyl groups such as a benzyl group, a phenethyl group, a 1-naphthylmethyl group, a 2-naphthylmethyl group, a 1-naphthylethyl group, and a 2-naphthylethyl group. The number of carbon atoms of the alkyl chain in the arylalkyl group is preferably 1 to 4, more preferably 1 or 2, and still more preferably 1.

The aromatic hydrocarbon group may contain a substituent group. For example, a part of carbon atoms which constitutes an aromatic ring included in the aromatic hydrocarbon group may be substituted with a hetero atom, or a part of hydrogen atoms bonded with an aromatic ring included in the aromatic hydrocarbon group may be substituted with a substituent group.

Examples of the former case include a heteroaryl group in which a part of carbon atoms which constitutes the ring of the aryl group described above is substituted with a hetero atom such as an oxygen atom, a sulfur atom, and a nitrogen atom; and a heteroarylalkyl group in which a part of carbon atoms which constitutes the ring of the arylalkyl group described above is substituted with the hetero atom.

On the other hand, examples of the substituent groups in the aromatic hydrocarbon group in the latter case include an alkyl group, an alkoxy group, a halogen atom, a halogenated alkyl group, a hydroxyl group, and an oxygen atom (=O).

The alkyl group for the substituent group in the aromatic hydrocarbon group is preferably an alkyl group of 1 to 5 carbon atoms, and most preferably a methyl group, an ethyl group, a propyl group, an n-butyl group, and a tert-butyl group.

The alkoxy group for the substituent group in the aromatic hydrocarbon group is preferably an alkoxy group of 1 to 5 carbon atoms, and more preferably a methoxy group, an ethoxy group, an n-propoxy group, an iso-propoxy group, an n-butoxy group, and a tert-butoxy group, and most preferably a methoxy group and an ethoxy group.

Examples of the halogen atom for the substituent group in the aromatic hydrocarbon group include a fluorine atom, a chlorine atom, a bromine atom, and an iodine atom. Of these, a fluorine atom is preferable.

Examples of the halogenated alkyl group for the substituent group in the aromatic hydrocarbon group include groups in which a part of or all of the hydrogen atoms of the above alkyl group are substituted with the halogen atoms.

The aliphatic hydrocarbon group for $R^X$ may be a saturated aliphatic hydrocarbon group or an unsaturated aliphatic hydrocarbon group.

The saturated aliphatic hydrocarbon group for $R^X$ is preferably a linear or branched alkyl group of 1 to 10 carbon atoms, or a cyclic alkyl group.

Examples of the linear alkyl group include a methyl group, an ethyl group, a propyl group, a butyl group, a pentyl group, a hexyl group, a heptyl group, an octyl group, a nonyl group, and a decanyl group. Of these, a methyl group is preferable.

Examples of the branched alkyl group include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, a 4-methylpentyl group.

The linear or branched alkyl group may contain a substituent group. Examples of the substituent group include an alkoxy group, a halogen atom, a halogenated alkyl group, a hydroxyl group, and an oxygen atom (=O). Specific examples thereof include those described as the substituent groups which the aromatic hydrocarbon groups may contain.

The cyclic alkyl group may be a monocyclic group or a polycyclic group. Examples thereof include groups in which one or more of hydrogen atoms have been removed from a monocycloalkane; and groups in which one or more of hydrogen atoms have been removed from a polycycloalkane such as a bicycloalkane, a tricycloalkane, or a tetracycloalkane. Specific examples include groups in which at least one hydrogen atom has been removed from a monocycloalkane such as cyclopentane and cyclohexane; and groups in which at least one hydrogen atom has been removed from a polycycloalkane such as adamantane, norbornane, isobornane, tricyclodecane or tetracyclododecane.

The cyclic alkyl group may contain a substituent group. For example, a part of carbon atoms which constitutes a ring included in the cyclic alkyl group may be substituted by hetero atoms; or a hydrogen atom bonded with the ring included in the cyclic alkyl group may be substituted with a substituent group. Examples of the former include groups in which one or more of hydrogen atoms are removed from a hetero cycloalkane in which a part of carbon atoms constituting the ring of the monocycloalkane or polycycloalkane are substituted with a hetero atom such as an oxygen atom, a sulfur atom, or a nitrogen atom. Also, an ester bond (—C(=O)—O—) may be contained in the above ring structure. Examples of the latter include those described as the substituent groups that the aromatic group for above $R^X$ may contain.

The unsaturated aliphatic hydrocarbon group for $R^X$ is preferably a linear or branched alkenyl group of 2 to 10 carbon atoms. The number of carbon atoms in the alkenyl group is preferably 2 to 5, more preferably 2 to 4, and still more preferably 3. Specific examples thereof include a vinyl group, a propenyl group (allyl group), a butynyl group, a 1-methylpropenyl group, and a 2-methylpropenyl group. Of these, a propenyl group is preferable.

The alkenyl group may contain a substituent group. Examples of the substituent group include those described as the substituent group which the linear or branched alkyl group may contain.

The alkylene group for $Q^1$ may be linear or branched. The alkylene group preferably has 1 to 5 carbon atoms, more preferably has 1 to 3 carbon atoms.

Specific examples of the alkylene group include a methylene group [—CH$_2$—]; an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an ethylene group [—CH$_2$CH$_2$—]; an alkylethelene group such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —CH(CH$_2$CH$_2$CH$_3$)CH$_2$—; a trimethylene group (n-propylene group) [—CH$_2$CH$_2$CH$_2$—]; an alkyltrimethylene group such as —CH(CH$_3$)CH$_2$CH$_2$—, and —CH$_2$CH(CH$_3$)CH$_2$—; an alkyltetramethylene group such as —CH(CH$_3$)CH$_2$CH$_2$CH$_2$—, and —CH$_2$CH(CH$_3$)CH$_2$CH$_2$—; and a pentamethylene group [—CH$_2$CH$_2$CH$_2$CH$_2$CH$_2$—].

$Q^1$ is preferably a methylene group, an ethylene group, an n-propylene group, or a single bond, and particularly preferably a single bond.

n represents an integer of 0 or 1, and preferably 0.

$Y^1$ represents an alkylene group of 1 to 4 carbon atoms or a fluorinated alkylene group of 1 to 4 carbon atoms.

Examples of $Y^1$ include —CF$_2$—, —CF$_2$CF$_2$—, —CF$_2$CF$_2$CF$_2$—, —CF(CF$_3$)CF$_2$—, —CF(CF$_2$CF$_3$)—, —C(CF$_3$)$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—, —CF(CF$_2$CF$_2$CF$_3$)—, —C(CF$_3$)(CF$_2$CF$_3$)—; —CHF—, —CH$_2$CF$_2$—, —CH$_2$CH$_2$CF$_2$—, —CH$_2$CF$_2$CF$_2$—, —CH(CF$_3$)CH$_2$—, —CH(CF$_2$CF$_3$)—, —C(CH$_3$)(CF$_3$)—, —CH$_2$CH$_2$CH$_2$CF$_2$—, —CH$_2$CH$_2$CF$_2$CF$_2$—, —CH(CF$_3$)CH$_2$CH$_2$—, —CH$_2$CH(CF$_3$)CH$_2$—, —CH(CF$_3$)CH(CF$_3$)—, —C(CF$_3$)$_2$CH$_2$—; —CH$_2$—, —CH$_2$CH$_2$—, —CH$_2$CH$_2$CH$_2$—, —CH(CH$_2$CH$_3$)—, —C(CH$_3$)$_2$—, —CH$_2$CH$_2$CH$_2$CH$_2$—, —CH(CH$_3$)CH$_2$CH$_2$—, —CH$_2$CH(CH$_3$)CH$_2$—, —CH(CH$_3$)CH(CH$_3$)—, —C(CH$_3$)$_2$CH$_2$—, —CH(CH$_2$CH$_3$)CH$_2$—, —CH(CH$_2$CH$_2$CH$_3$)—, and —C(CH$_3$)(CH$_2$CH$_3$)—.

$Y^1$ is preferably a fluorinated alkylene group, and particularly preferably a fluorinated alkylene group in which the carbon atom bonded with the adjacent sulfur atom is fluorinated. Examples of the fluorinated alkylene groups include —CF$_2$—, —CF$_2$CF$_2$—, —CF$_2$CF$_2$CF$_2$—, —CF(CF$_3$)CF$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)2CF2—, —CF(CF$_2$CF$_3$)CF$_2$—; —CH$_2$CF$_2$—, —CH$_2$CH$_2$CF$_2$—, —CH$_2$CF$_2$CF$_2$—; CH$_2$CH$_2$CH$_2$CF$_2$—, —CH$_2$CH$_2$CF$_2$CF$_2$—, and —CH$_2$CF$_2$CF$_2$CF$_2$—.

Of these, —CF$_2$—, —CF$_2$CF$_2$—, —CF$_2$CF$_2$CF$_2$—, or —CH$_2$CF$_2$CF$_2$— is preferable, —CF$_2$—, —CF$_2$CF$_2$—, or —CF$_2$CF$_2$CF$_2$— is more preferable, and —CF$_2$— or —CF$_2$CF$_2$— is still more preferable.

There is no particular restriction on the organic cation of A$^+$ as long as it contains a nitrogen atom, and those which contain a nitrogen atom may arbitrarily be selected from those conventionally suggested as a cation moiety of an onium salt-based acid generator.

Specific examples of A$^+$ include an onium ion (sulfonium ion, iodonium ion, or the like) which contain an aryl group and/or an alkyl group in which a substituent group containing a nitrogen atom is introduced into the aryl group and/or the alkyl group.

The substituent group containing a nitrogen atom (hereinafter, referred to as nitrogen-containing substituent group) is preferably a group which contains, at the terminal, at least one selected from the group consisting of a an amino group (—NH$_3$), a substituted amino group in which a part or all of hydrogen atoms in the amino group are substituted with a substituent group, and a cyclic group containing a nitrogen atom.

Examples of the substituent group in the substituted amino group include an alkyl group, an aliphatic cyclic group, and an aromatic cyclic group.

The alkyl group is preferably a linear or branched alkyl group, and the number of carbon atoms in the alkyl group is preferably 1 to 8, and more preferably 1 to 4.

The alkyl group may contain a substituent group. Examples of the substituent group in the alkyl group include an alkoxy group, a halogen atom, a halogenated alkyl group, a hydroxyl group, and an oxygen atom (=O). Specific examples thereof include the same as those described as the substituted groups that the aromatic group in $R^X$ may contain.

The aliphatic cyclic group is the same as those described as the cyclic alkyl group in $R^X$.

The aliphatic cyclic group may contain a substituent group. Examples of the substituent group in the aliphatic cyclic group include an alkyl group, an alkoxy group, a halogen atom, a halogenated alkyl group, a hydroxyl group, and an oxygen atom (=O). Specific examples thereof include the same as those described as the substituent groups that the aromatic group in $R^X$ may contain.

Examples of the aromatic cyclic group include the same as those described above as the aromatic hydrocarbon groups in $R^X$.

The aromatic cyclic group may contain a substituent group. Examples of the substituent group in the aromatic cyclic group include an alkyl group, an alkoxy group, a halogen atom, a halogenated alkyl group, a hydroxyl group, and an oxygen atom (=O). Specific examples thereof include the same as those described above as the substituent groups that the aromatic group in $R^X$ may contain.

$A^+$ preferably contains, as a nitrogen-containing substituent group, a group represented by a general formula (I) shown below.

[Chemical Formula 3]

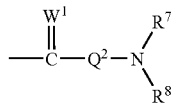

(I)

(in the formula, $W^1$ represents an oxygen atom or a sulfur atom; $Q^2$ represents an alkylene group or a single bond; and $R^7$ and $R^8$ each independently represents a hydrogen atom, an alkyl group which may contain a substituent group, an aliphatic cyclic group which may contain a substituent group, or an aromatic cyclic group which may contain a substituent group, wherein $R^7$ and $R^8$ may mutually be bonded to form a ring.)

In the formula, the alkylene group for $Q^2$ is preferably a linear or branched alkylene group, and the number of carbon atoms in the alkylene group is preferably 1 to 5, and more preferably 1 to 3.

Examples of the alkyl group, the aliphatic cylic group, and the aromatic cyclic group for $R^7$ and $R^8$, respectively, include the same as the alkyl group, the aliphatic cyclic group, and the aromatic cyclic group described above as the substituent group in the substituent amino group.

In the case that $R^7$ and $R^8$ are mutually bonded to form a ring, the ring is preferably a 3- to 8-membered ring, and more preferably a 5- to 7-membered ring.

The ring may contain a substituent group. Examples of the substituent group which the ring may contain include an alkyl group, an alkoxy group, a halogen atom, a halogenated alkyl group, a hydroxyl group, and an oxygen atom (=O). Specific examples thereof include those described above as the substituent groups which the aromatic hydrocarbon group for $R^X$ may contain.

In $A^+$, the group represented by the above general formula (I) is preferably bonded with an oxygen atom or a sulfur atom, in terms of the ease of manufacturing.

Specific examples of $A^+$ include a cation moiety represented by a general formula (b-1), (b-2), (b-5), or (b-6) shown below.

[Chemical Formula 4]

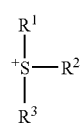

(b-1)

(wherein, $R^1$ to $R^3$ each independently represents an aryl group which may contain a substituent group, or an alkyl group which may contain a substituent group, at least one of $R^1$ to $R^3$ represents an aryl group, and at least one of $R^1$ to $R^3$ contains a substituent group represented by a general formula (I-1) shown below; alternatively, $R^1$ and $R^2$ are mutually bonded to form a ring together with the sulfur ion in the formula, $R^3$ represents an aryl group which may contain a substituent group, an alkyl group which may contain a substituent group, or a group of $-R^4-C(=O)-R^5$ (wherein, $R^4$ represents an alkylene group of 1 to 5 carbon atoms, and $R^5$ represents an aryl group which may contain a substituent group), and one or both of the ring and $R^3$ contain a substituent group represented by a general formula (I-1) shown below.)

[Chemical Formula 5]

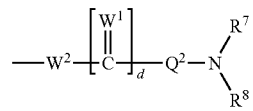

(I-1)

(wherein, $W^1$, $Q^2$, $R^7$, and $R^8$ are as defined above; $W^2$ represents a bivalent linking group; and d represents an integer of 0 or 1.)

[Chemical Formula 6]

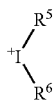

(b-2)

(In the formula, $R^5$ and $R^6$ each independently represents an aryl group which may contain a substituent group, or an alkyl group which may contain a substituent group; and at least one of $R^5$ and $R^6$ contains a substituent group represented by the general formula (I-1).)

[Chemical Formula 7]

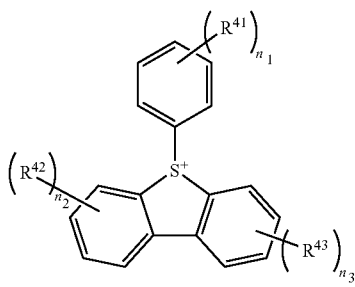

(b-5)

(In the formula, $R^{41}$ to $R^{43}$ each independently represents a substituent group represented by the general formula (I-1), an alkyl group, an acetyl group, an alkoxy group, a carboxy group, or a hydroxyalkyl group; at least one of $R^{41}$ to $R^{43}$ is a substituent group represented by the general formula (I-1); $n_1$ represents an integer of 0 to 5; $n_2$ and $n_3$ each independently represents an integer of 0 to 3; and $n_1+n_2+n_3$ is an integer of 1 or more.)

[Chemical Formula 8]

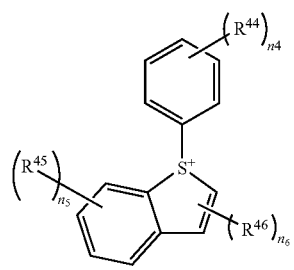

(b-6)

(in the formula, $R^{44}$ to $R^{46}$ each independently represents a substituent group represented by the general formula (I-1), an alkyl group, an acetyl group, an alkoxy group, a carboxy group, or a hydroxyalkyl group; at least one of $R^{44}$ to $R^{46}$ represents a substituent group represented by the general formula (I-1); $n_4$ represents an integer of 0 to 5; $n_5$ represents an integer of 0 to 3; $n_6$ represents an integer of 0 to 2; and $n_4+n_5+n_6$ is an integer of 1 or more.)

The cation moiety represented by the general formula (b-1), (b-2), (b-5), or (b-6) contains at least one substituent group represented by the general formula (I-1) (hereinafter, referred to as substituent group (I-1)).

In the formula (I-1), examples of the bivalent linking group for $W^2$ include an alkylene group, and a group containing a hetero atom (hereinafter, referred to as hetero atom-containing linking group).

The alkylene group is preferably a linear or branched alkylene group, and the number of carbon atoms in the alkylene group is preferably 1 to 5, and more preferably 1 to 3. Of these, an ethylene group is most preferable.

The term "hetero atom" in the hetero atom-containing linking group means an atom other than a carbon atom and hydrogen atom, and examples thereof include an oxygen atom, a sulfur atom, and a nitrogen atom.

Examples of the hetero atom-containing linking group include non hydrocarbon-based hetero atom-containing linking groups such as an oxygen atom (ether linkage; —O—), a sulfur atom (thioether linkage; —S—), a —NH— linkage (wherein, H may be substituted with a substituent group such as an alkyl group, an acyl group, or the like), an ester linkage (—COO—), an amide linkage (—CONH—), a carbonyl group (—CO—), or a carbonate linkage (—OCOO—); and combined groups of the non hydrocarbon-based hetero atom-containing linking groups with the alkylene groups. Examples of the above combined groups include a group of —$R^{91}$—O— (wherein, $R^{91}$ represents an alkylene group). In the above group of —$R^{91}$—O—, the alkylene group for $R^{91}$ is the same as the alkylene group described above as the bivalent linking group for $W^2$.

In the present invention, the bivalent linking group for $W^2$ is preferably an oxygen atom, a sulfur atom, or the above group of —$R^{91}$—O—, and more preferably an oxygen atom or the above group of —$R^{91}$—O—.

In the formula (b-1), there is no particular restriction on the aryl group for $R^1$ to $R^3$, and examples thereof include non-substituted aryl groups of 6 to 20 carbon atoms; and substituted aryl groups in which a part or all of hydrogen atoms in the above non-substituted aryl groups is substituted with the substituent group (I-1), an alkyl group, an alkoxy group, an alkoxyalkyloxy group, an alkoxycarbonylalkyloxy group, a halogen atom, a hydrogen atom, and the like.

The non-substituted aryl group is preferably an aryl group of 6 to 10 carbon atoms, because it can be synthesized inexpensively. Specific examples thereof include a phenyl group and a naphthyl group.

The alkyl group for the substituent group in the substituted aryl group is preferably an alkyl group of 1 to 5 carbon atoms, and most preferably a methyl group, an ethyl group, a propyl group, an n-butyl group, and a tert-butyl group.

The alkoxy group for the substituent group in the substituted aryl group is preferably an alkoxy group of 1 to 5 carbon atoms, and most preferably a methoxy group, an ethoxy group, an n-propoxy group, an iso-propoxy group, an n-butoxy group, and a tert-butoxy group.

The halogen atom for the substituent group in the substituted aryl group is preferably a fluorine atom.

Examples of the alkoxyalkyloxy group for the substituent group in the substituted aryl group include groups represented by a general formula —O—C($R^{47}$)($R^{48}$)—O—$R^{49}$ (wherein, $R^{47}$ and $R^{48}$ each independently represents a hydrogen atom, or a linear or branched alkyl group; and $R^{49}$ represents an alkyl group).

The alkyl group for $R^{47}$ and $R^{48}$ preferably has 1 to 5 carbon atoms, and may be either linear or branched. As the alkyl group, an ethyl group or a methyl group is preferable, and a methyl group is most preferable.

At least one of $R^{47}$ and $R^{48}$ is preferably a hydrogen atom. Particularly, it is preferable that one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched, or cyclic.

The linear or branched alkyl group for $R^{49}$ preferably has 1 to 5 carbon atoms, and examples thereof include a methyl group, an ethyl group, a propyl group, an n-butyl group, and a tert-butyl group.

The cyclic alkyl group for $R^{49}$ preferably has 4 to 15 carbon atoms, more preferably has 4 to 12 carbon atoms, and most preferably 5 to 10 carbon atoms. Specific examples of the cyclic alkyl group for $R^{49}$ include groups in which one or more hydrogen atoms have been removed from a monocycloalkane or a polycycloalkane such as a bicycloalkane, tricycloalkane or tetracycloalkane, in which an alkyl group of 1 to 5 carbon atoms, a fluorine atom, or a fluorinated alkyl group of 1 to 5 carbon atoms may or may not be included as a substituent group. Specific examples of monocycloalkanes include cyclopentane and cyclohexane. Specific examples of polycycloalkanes include adamantane, norbornane, isobornane, tricyclodecane, and tetracyclododecane. Of these, a group in which one or more hydrogen atoms have been removed from adamantane is preferable.

Examples of the alkoxycarbonylalkyloxy group for the substituent group in the substituted aryl group include groups represented by a general formula —O—$R^{50}$—C(=O)—$OR^{51}$ (wherein, $R^{50}$ represents a linear or branched alkylene group, and $R^{51}$ represents a tertiary alkyl group).

The linear or branched alkylene group for $R^{50}$ preferably has 1 to 5 carbon atoms, and examples thereof include a methylene group, an ethylene group, a trimethylene group, a tetramethylene group, and a 1,1-dimethylethylene group.

Examples of the tertiary alkyl group for $R^{51}$ include a 2-methyl-2-adamantyl group, 2-ethyl-2-adamantyl group, 1-methyl-1-cyclopentyl group, 1-ethyl-1-cyclopentyl group, 1-methyl-1-cyclohexyl group, 1-ethyl-1-cyclohexyl group, 1-(1-adamantyl)-1-methylethyl group, 1-(1-adamantyl)-1-methylpropyl group, 1-(1-adamantyl)-1-methylbutyl group, 1-(1-adamantyl)-1-methylpentyl group; 1-(1-cyclopentyl)-1-methylethyl group, 1-(1-cyclopentyl)-1-methylpropyl group, 1-(1-cyclopentyl)-1-methylbutyl group, 1-(1-cyclopentyl)-1-methylpentyl group 1; 1-(1-cyclohexyl)-1-methylethyl group, 1-(1-cyclohexyl)-1-methylpropyl group, 1-(1-cyclohexyl)-1-methylbutyl group, 1-(1-cyclohexyl)-1-methylpentyl group, tert-butyl group, tert-pentyl group, and tert-hexyl group.

There is no particular restriction on the alkyl group for $R^1$ to $R^3$, and examples thereof include a linear, branched, or cyclic alkyl group of 1 to 10 carbon atoms. The number of carbon atoms is preferably 1 to 5, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

The alkyl group for $R^1$ to $R^3$ may contain a substituent group. Examples of the substituent group include the substituent group (I-1), an alkoxy group, an alkoxyalkyloxy group, an alkoxycarbonylalkyloxy group, a halogen atom, and a hydroxyl group. Specific examples thereof include the same as those described above in the substituted aryl group.

At least one of $R^1$ to $R^3$ is an aryl group, preferably two of them are aryl groups, and most preferably all of them are aryl groups. The aryl group is preferably a phenyl group or a naphthyl group.

Also, preferably at least one of $R^1$ to $R^3$, more preferably one or two of them, and still more preferably only one of them contains the substituent group (I-1) as a substituent group. Also, the substituent group (I-1) is preferably bonded with the aryl group. That is, at least one of $R^1$ to $R^3$ is preferably an aryl group which contains the substituent group (I-1).

Also, $R^1$ to $R^3$ may contain a substituent group other than the substituent group (I-1), such as those described above.

In the formula (b-1), $R^1$ and $R^2$ may mutually be bonded to form a ring together with the sulfur ion in the formula. In this case, the ring is preferably a 3- to 10-membered ring including the sulfur ion, and more preferably a 5- to 7-membered ring.

In the case that $R^1$ and $R^2$ are mutually bonded to form a ring together with the sulfur atom in the formula, $R^3$ is an aryl group which may contain a substituent group, an alkyl group which may contain a substituent group, or a group of —$R^4$—C(=O)—$R^5$ (wherein, $R^4$ represents an alkylene group of 1 to 5 carbon atoms, and $R^5$ represents an aryl group which may contain a substituent group.).

The aryl group and alkyl group for $R^3$ is respectively the same as the aryl group and alkyl group for $R^1$ to $R^3$.

The alkylene group for $R^4$ is preferably a linear or branched alkykene group. The number of carbon atoms in the alkylene group is preferably 1 to 5.

The aryl group for $R^5$ is the same as the aryl group for $R^1$ to $R^3$.

In the case that $R^1$ and $R^2$ are mutually bonded to form a ring together with the sulfur atom in the formula, one or both of the ring and $R^3$ contain the substituent group.

The substituent group (I-1) is preferably bonded with an aryl group. That is, $R^3$ is preferably an aryl group which contains the substituent group (I-1), or the group of —($R^4$)—C(=O)—$R^5$ in which the substituent group (I-1) is bonded with the aryl group for $R^5$.

The cation moiety represented by the general formula (b-1) is preferably a cation moiety represented by a general formula (b-1-1) or (b-1-2) shown below, and particularly preferably a cation moiety represented by the general formula (b-1-1).

[Chemical Formula 9]

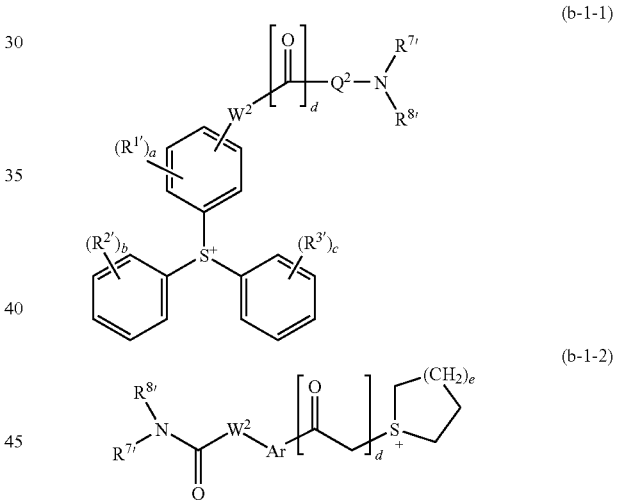

In the formula (b-1-1), $W^2$, $Q^2$, $R^{7'}$, and $R^{8'}$ are the same as $W^2$, $Q^2$, $R^7$, and $R^8$ in the formula (I-1), respectively.

There is no particular restriction on the binding position of the group of "—$W^2$—(C(=O))$_d$-$Q^2$-N($R^{7'}$)($R^{8'}$)", and it is preferably a 3- or 4-position of a phenyl group, and most preferably a 4-position thereof.

$R^{1'}$ is an alkyl group or an alkoxy group. Examples of the alkyl group and alkoxy group include the same as those described above as the alkyl group and alkoxy group, respectively, for the substituent group in the substituted aryl group for $R^1$ to $R^3$.

a represents an integer of 0 to 2.

d represents an integer of 0 or 1.

$R^{2'}$ and $R^{3'}$ each independently represents a group of —$W^2$—(C(=O))$_d$-$Q^2$-N($R^{7'}$)($R^{8'}$), an alkyl group, or an alkoxy group. The group of —$W^2$—(C(=O))$_d$-$Q^2$-N($R^{7'}$)($R^{8'}$), the alkyl group, and the alkoxy group are respectively as defined above.

b and c each independently represents an integer of 0 to 3, and is preferably 0 or 1.

In the formula (b-1-2), $W^2$, $R^{7\prime}$, and $R^{8\prime}$ are the same as $W^2$, $R^7$, and $R^8$ in the formula (I-1), respectively.

Ar represents an aryl group. Examples of the aryl group for Ar include the same as the aryl group for $R^1$ to $R^3$. Of these, a phenyl group is preferable.

d represents an integer of 0 or 1.

e represents an integer of 0 to 3, and is most preferably 1 or 2.

In the formula (b-2), the aryl group and alkyl group for $R^5$ and $R^6$ are respectively the same as the aryl group and alkyl group for $R^1$ to $R^3$.

It is preferable that at least one of $R^5$ and $R^6$ be an aryl group, and it is more preferable that both of $R^5$ and $R^6$ be aryl groups. Of these, it is most preferable that both of $R^5$ and $R^6$ be phenyl groups.

Also, at least one of $R^5$ and $R^6$, preferably one of $R^5$ and $R^6$ contains the substituent group (I-1). The substituent group (I-1) is preferably bonded with an aryl group. That is, at least one of $R^1$ to $R^3$ is preferably an aryl group which contains the substituent group (I-1).

Also, $R^5$ and $R^6$ may contain a substituent group other than the substituent group (I-1), such as those described above.

In the formula (b-5), the alkyl group for $R^{41}$ to $R^{43}$ is preferably an alkyl group of 1 to 5 carbon atoms, more preferably a linear or branched alkyl group, and still more preferably a methyl group, an ethyl group, a propyl group, an isopropyl group, an n-butyl group, or a tert-butyl group.

The alkoxy group for $R^{41}$ to $R^{43}$ is preferably an alkoxy group of 1 to 5 carbon atoms, more preferably a linear or branched alkoxy group, and particularly preferably a methoxy group or an ethoxy group.

The hydroxyalkyl group for $R^{41}$ to $R^{43}$ is preferably a group in which one or more hydrogen atoms in the alkyl group for $R^{41}$ to $R^{43}$ are substituted with hydroxyl groups, and examples thereof include a hydroxymethyl group, a hydroxyethyl group, and a hydroxypropyl group.

$n_1$ is preferably 1 to 3.

It is preferable that $n_2$ and $n_3$ be each independently 0 or 1, and it is more preferable that they be 0.

In the case that $n_1$, $n_2$, or $n_3$ is an integer of 2 or more, a plurality of $R^{41}$, $R^{42}$, or $R^{43}$ are the same or different, respectively.

At least one of $R^{41}$ to $R^{43}$, preferably only one of $R^{41}$ to $R^{43}$ are a substituent group (I-1). It is particularly preferable that $R^{41}$ have a substituent group (I-1).

Also, $R^{41}$ to $R^{43}$ may contain a substituent group other than the substituent group (I-1), such as those described above.

In the formula (b-6), $R^{44}$ to $R^{46}$ is the same as those described above in $R^{41}$ to $R^{43}$.

$n_4$ is preferably 1 to 3.

$n_5$ is preferably 0 or 1, and more preferably 0.

$n_6$ is preferably 0 or 1.

In the case that $n_4$, $n_5$, or $n_6$ is an integer of 2 or more, a plurality of $R^{44}$, $R^{45}$, or $R^{46}$ may respectively be the same, or different.

At least one of $R^{44}$ to $R^{46}$, preferably one of $R^{44}$ to $R^{46}$ is the substituent group (I-1). It is particularly preferable that $R^{44}$ have the substituent group (I-1).

Also, $R^{44}$ to $R^{46}$ may contain a substituent group other than the substituent group (I-1), such as those described above.

In the present invention, $A^+$ is preferably a cation moiety represented by the formula (b-1).

That is, the compound (B1) is preferably a compound represented by a general formula (B1-1-1) shown below.

[Chemical Formula 10]

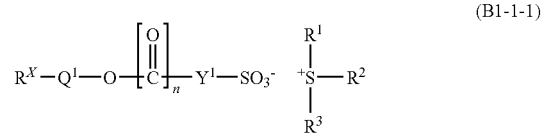

(B1-1-1)

(wherein, $R^X$, $Q^1$, $Y^1$, and $R^1$ to $R^3$ are as defined above, respectively.)

<Method of Manufacturing Compound (B1)>

There is no particular limitation on a method of manufacturing the compound (B1), and examples thereof include a manufacturing method which includes the step of reacting a compound (b0-1) represented by a general formula (b0-1) shown below with a compound (b0-2) represented by a general formula (b0-2) shown below.

[Chemical Formula 11]

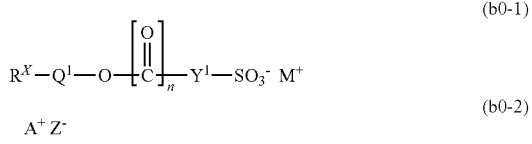

(b0-1)

(b0-2)

In the formula (b0-1), $R^X$, $Q^1$, n, and $Y^1$ are the same as $R^X$, $Q^1$, n, and $Y^1$ in the formula (B1-1), respectively.

$M^+$ represents an alkali metal ion. Examples of the alkali metal ion for $M^+$ include a sodium ion, a lithium ion, and a potassium ion. Of these, a sodium ion or a lithium ion is preferable.

In the formula (b0-2), $A^+$ is the same as $A^+$ in the formula (B1-1).

$Z^-$ represents a halogen ion, a sulfonate ion, $BF_4^-$, $AsF_6^-$, $SbF_6^-$, $PF_6^-$, or $ClO_4^-$.

Examples of the halogen ion for $Z^-$ include a bromine ion, a chlorine ion, and an iodine ion. Of these, a bromine ion and a chlorine ion are preferable.

Examples of the sulfonate ion for $Z^-$ include a p-toluenesulfonate ion, a methanesulfonate ion, a benzenesulfonate ion, and a trifluoromethanesulfonate ion.

As the compound (b0-1) or (b0-2), a commercially available compound may be used, or a compound obtained by the synthesis may be used.

There is no particular restriction on the method of manufacturing the compound (b0-1). For example, a compound represented by a general formula (b0-1-11) shown below is reacted in a solvent such as a tetrahydrofuran or water, or in an aqueous solution of an alkali metal hydroxide such as a sodium hydroxide or a lithium hydroxide, thereby obtaining a compound represented by a general formula (b0-1-12) shown below, and then the compound represented by the general formula (b0-1-12) is dehydratively-condensed with an alcohol represented by a general formula (b0-1-13) shown below, thereby obtaining a compound represented by the general formula (b0-1) in which n is 1 (that is, a compound represented by a general formula (b0-1-01) shown below).

[Chemical Formula 12]

$$R^{21}-O-\overset{O}{\underset{\|}{C}}-Y^1-SO_2F \quad (b0\text{-}1\text{-}11)$$

$$M^+\,{}^-O-\overset{O}{\underset{\|}{C}}-Y^1-SO_3^-\,M^+ \quad (b0\text{-}1\text{-}12)$$

$$R^X-Q^1-OH \quad (b0\text{-}1\text{-}13)$$

$$R^X-Q^1-O-\overset{O}{\underset{\|}{C}}-Y^1-SO_3^-\,M^+ \quad (b0\text{-}1\text{-}1)$$

(wherein, $R^{21}$ represents an alkyl group of 1 to 5 carbon atoms; $R^X$, $Q^1$, $Y^1$, and $M^+$ are respectively the same as $R^X$, $Q^1$, $Y^1$, and $M^+$ in the formula (b0-1).)

Also, for example, a compound represented by a general formula (b0-1-01) shown below and a compound represented by a general formula (b0-1-02) shown below are reacted in an organic solvent such as anhydrous diglyme, thereby obtaining a compound represented by a general formula (b0-1-03) shown below, and then the compound represented by the general formula (b0-1-03) is reacted with an alkali metal hydroxide such as a sodium hydroxide or a lithium hydroxide in an organic solvent such as a tetrahydrofuran, an acetone, and a methyl ethyl ketone, thereby obtaining a compound represented by the general formula (b0-1) in which n is 0 (that is, a compound represented by a general formula (b0-1-0) shown below).

The halogen atom for $X_h$ in the formula (b0-1-02) is preferably a bromine atom or a chlorine atom.

[Chemical Formula 13]

$$Y^1\underset{SO_2}{\overset{O}{\triangle}} \quad (b0\text{-}1\text{-}01)$$

$$R^X-Q^1-X_h \quad (b0\text{-}1\text{-}02)$$

$$R^X-Q^1-O-Y^1-SO_2F \quad (b0\text{-}1\text{-}03)$$

$$R^X-Q^1-O-Y^1-SO_3^-\,M^+ \quad (b0\text{-}1\text{-}0)$$

(wherein, $R^X$, $Q^1$, $Y^1$, and $M^+$ are respectively the same as $R^X$, $Q^1$, $Y^1$, and $M^+$ in the formula (b0-1); and $X_h$ represents a halogen atom.)

There is no particular limitation on a method of manufacturing the compound (b0-2). For example, the compound (b0-2) can be manufactured as follows. Generally, an onium salt which has conventionally been used as a raw material of an onium salt-based acid generator contains no nitrogen atom Here, a nitrogen-containing substituent group described above is introduced into a cation moiety of such an onium salt by using a conventional method, thereby enabling the compound (b0-2) to be obtained.

As a specific example, the case that the above $A^+$ is an onium salt containing the substituent group (I-1) will be described below. An onium salt which has a cation moiety containing a group of $-W^2-H$ (wherein, $W^2$ is as defined above) as a substituent group is provided, for example, and then the onium salt is reacted with a compound represented by a general formula (I-0) shown below. By the reaction, the hydrogen atom in the group of $-W^2-H$ is substituted with the group of $-(C(=W^1))_d-Q^2-N(R^7)(R^8)$. As a result, an onium salt which includes $A^+$ containing the substituent group (I-1) can be obtained.

[Chemical Formula 14]

$$X_{h'}{-}\!\!\left[\overset{W^1}{\underset{\|}{C}}\right]_{\!d}{-}Q^2{-}N\!\!\begin{array}{c}R^7\\ \diagdown\\ R^8\end{array} \quad (I\text{-}0)$$

(wherein, $W^1$, $Q^2$, $R^7$, and $R^8$ are as defined above; $X_{h'}$ represents a halogen atom; and d represents an integer of 0 or 1.)

Examples of the halogen atom for $X_{h'}$ include a bromine atom, a chlorine atom, and an iodine atom. Of these, a bromine atom or a chlorine atom is preferable.

As the compound (I-0), a commercially available compound can be used.

The reaction of the onium salt with the compound (I-0) can be performed, for example, by dissolving the onium salt in a solvent such as tetrahydrofuran, and then adding the compound (1-0) therein in the presence of a base.

The amount used of compound (I-0) is generally 1 to 100 mol-fold for the amount of the onium salt, and preferably 1.5 to 10 mol-fold.

Examples of the base used in the above reaction include triethylamine, pyridine, potassium hydroxide, sodium hydroxide, sodium hydrogen carbonate, and potassium hydrogen carbonate.

The amount used of the base is generally within a range of 1.0 to 10.0 mol-fold for the amount of the compound (I-0), and preferably 2.0 to 4.0 mol-fold.

The solvent used in the reaction is preferably an aprotic organic solvent such as tetrahydrofuran, toluene, dichloromethane, pyridine, DMF, DMSO, and acetone.

The reaction temperature is usually within a range of 20 to 150° C., and preferably within a range of 50 to 100° C. Also, the reaction time is usually within a range of 0.1 to 72 hours, and preferably within a range of 1 to 24 hours.

The reaction of the compound (b0-1) with the compound (b0-2) can be performed, for example, by dissolving these compounds in a solvent such as water, dichloromethane, acetonitrile, methanol, chloroform, or methylene chloride, and stirring the solution thus obtained.

The reaction temperature is preferably 0 to 150° C., and more preferably 0 to 100° C. Usually, the reaction time is preferably 0.5 to 10 hours, and more preferably 1 to 5 hours, although it is different according to the reactivity of the compound (b0-1) and the compound (b0-2), the reaction temperature, and the like.

The amount of the compound (b0-2) used in the above reaction is usually 0.5 to 2 mol, relative to 1 mol of the compound (b0-1).

The structure of the compound obtained by the above method can be confirmed by a general organic analysis method such as a $^1$H-nuclear magnetic resonance (NMR) spectrum method, a $^{19}$F-NMR spectrum method, an infrared resonance (IR) spectrum method, a mass spectrometry (MS) method, an element analysis method, and an X-ray crystallographic analysis method.

The compound (B1) is a novel compound which is available as an acid generator, and can be blended in a resist compound as an acid generator.

<<Acid Generator>>

An acid generator according to the fourth aspect of the present invention is composed of the compound (B1) described in the third aspect.

The acid generator is useful as an acid generator for a chemically-amplified resist composition, for example, as an acid generator component (B) of the resist composition according to the first aspect of the present invention, which is described below.

<<Resist Composition>>

A resist composition according to the first aspect of the present invention includes a base resin (A) which displays changed solubility in an alkali developing solution under action of acid (hereinafter, referred to as component (A)), and an acid generator component (B) which generates an acid upon exposure (hereinafter, referred to as component (B)), wherein the component (B) comprises an acid generator (B 1) composed of the compound represented by the general formula (B1-1).

A resist film formed by using the resist composition makes an acid generated from the component (B) when a selective exposure is conducted in the formation of the resist pattern, and the component (A) changes solubility in an alkali developing solution under action of acid thus generated from the component (B). As a result, whereas the exposed portions of the resist film change solubility in an alkali developing solution, the unexposed portions do not change solubility in an alkali developing solution. Therefore, if the resist composition is a positive resist composition, the exposed portions are dissolved to be removed by a developing treatment with alkali, thereby forming a resist pattern. On the other hand, if the resist composition is a negative resist composition, the unexposed portions are dissolved to be removed by a developing treatment with alkali, thereby forming a resist pattern.

The resist composition of the present invention may be a negative resist composition or a positive resist composition.

<Component (A)>

As the component (A), one kind of organic compound used as a resin component for a chemically-amplified resist can be used alone, or two or more of them can be used in combination.

Here, the term "base component" represents an organic compound which has a film-forming performance, and the molecular weight thereof is preferably 500 or more. When the molecular weight of the organic compound is 500 or more, the film-forming performance can be improved, and a nano-level resist pattern can easily be formed.

The organic compounds whose molecular weight is 500 or more can be classified broadly into a low molecular weight organic compound whose molecular weight is within a range from 500 to less than 2000 (hereinafter, referred to as low molecular weight compound), and a resin (polymer material) whose molecular weight is 2000 or more. As the low molecular weight compound, a non-polymer is usually used. In the case of using a resin (polymer, copolymer), the polystyrene equivalent molecular weight determined by gel permeation chromatography (GPC) is used as "molecular weight". Hereinafter, in the case of merely using the term "resin", it means a resin with a molecular weight of 2000 or more.

As the component (A), a resin which changes the solubility in an alkali solution under action of acid can be used, and also a low molecular weight compound which changes the solubility in an alkali solution under action of acid can be used.

In the case that the resist composition of the present invention is a negative resist composition, a resin soluble in an alkali developing solution is used as the component (A), and a cross-linking agent is blended with the negative resist composition.

In the negative resist composition, when acid is generated from the component (B) upon exposure, the action of this acid causes cross-linking reaction between the alkali-soluble resin and the cross-linking agent, and the cross-linked portion becomes poorly-soluble in an alkali developing solution. Therefore, in the formation of a resist pattern, when a resist film obtained by applying the negative resist composition on the substrate is subjected to selective exposure, the exposed area becomes poorly-soluble in an alkali developing solution, while the unexposed area remains soluble in the alkali developing solution, and hence a resist pattern can be formed by a developing treatment with an alkali.

A resin (hereinafter referred to as alkali-soluble resin) which is soluble in an alkali developing solution before exposure and changes to be insoluble after exposure is usually used as the component (A) of the negative resist composition.

As the alkali-soluble resin, it is preferable to use a resin having a structural unit derived from at least one of an α-(hydroxyalkyl)acrylic acid and a lower alkyl ester of α-(hydroxyalkyl)acrylic acid, because it enables formation of a satisfactory resist pattern with minimal swelling. Here, the term "α-(hydroxyalkyl)acrylic acid" represents one or both of an acrylic acid in which a hydrogen atom is bonded with the carbon atom at the α-position with which the carboxyl group bonded, and an α-hydroxyalkylacrylic acid in which a hydroxyalkyl group (preferably a hydroxyalkyl group of 1 to 5 carbon atoms) is bonded with the carbon atom at the α-position.

As a cross-linking agent, usually, an amino-based cross-linking agent such as a glycoluril that contains a methylol group or an alkoxymethyl group is preferable, because it enables an excellent resist pattern with minimal swelling to be formed. The blend quantity of the cross-linking agent is preferably within a range from 1 to 50 parts by weight, relative to 100 parts by weight of the alkali-soluble resin.

If the resist composition of the present invention is a positive resist composition, a base component which exhibits increased solubility in an alkali developing solution under action of acid can be used as the component (A). The component (A) is hardly-soluble in an alkali developing solution before exposure, and when an acid is generated from the component (B) upon exposure, the component (A) increases solubility in an alkali solution under action of acid. Therefore, in the formation of a resist pattern, when a resist film obtained by applying the positive resist composition on the substrate is subjected to selective exposure, the exposed area becomes soluble in an alkali, while the unexposed area remains insoluble in alkali, and hence a resist pattern can be formed by a developing treatment with an alkali.

In the resist composition of the present invention, the component (A) is preferably a base component which exhibits increased solubility in an alkali developing solution under action of acid. That is, the resist composition of the present invention is preferably a positive resist composition.

The component (A) may be a resin component (A1) which displays increased solubility in an alkali developing solution under action of acid (hereinafter, sometimes referred to as component (A1)), may be a low molecular weight compound (A2) which displays increased solubility in an alkali developing solution under action of acid (hereinafter, sometimes referred to as component (A2)), or may be a mixture of components (A1) and (A2).

[Component (A1)]

As the component (A1), one kind can be used alone selected from resin components (base resins) used as base components for a chemically-amplified resist, or two or more can be used in combination.

In the present invention, the component (A1) preferably contains a structural unit derived from an acrylate ester.

Herein, in the present specification and claims, the term "structural unit" means a monomer unit that contributes to the formation of a resin component (polymer compound).

The term "structural unit derived from an acrylate ester" means a structural unit that is formed by the cleavage of the ethylenic double bond of an acrylate ester.

The term "acrylate ester" is a concept containing an acrylate ester in which a hydrogen atom is bonded with a carbon atom at the α-position, and an α-substituted acrylate ester in which a hydrogen atom bonded with a carbon atom at the α-position is substituted with another substituent group (an atom or group other than a hydrogen atom). Examples of the substituent group include a lower alkyl group, and a halogenated lower alkyl group.

The term "α-position (carbon atom at the α-position)" in a structural unit derived from an acrylate ester represents a carbon atom with which a carbonyl group is bonded, if not otherwise specified.

The term "lower alkyl group" represents an alkyl group of 1 to 5 carbon atoms.

In the acrylate ester, specific examples of the lower alkyl group as the substituent group at the α-position include linear or branched lower alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated lower alkyl group include groups in which a part of or all of the hydrogen atoms of the aforementioned "lower alkyl group for the substituent group at the α-position" are substituted with halogen atoms. Examples of the halogen atom include a fluorine atom, a chlorine atom, an iodine atom, and a bromine atom. Of these, a fluorine atom is preferable.

In the present invention, the group which is bonded with the α-position is preferably a hydrogen atom, a lower alkyl group or a halogenated lower alkyl group, more preferably a hydrogen atom, a lower alkyl group or a fluorinated lower alkyl group, and still more preferably a hydrogen atom or a methyl group, in terms of industrial availability.

The component (A1) particularly preferably includes a structural unit (a1) derived from an acrylate ester which has an acid dissociable, dissolution inhibiting group.

Also, it is preferable that the component (A1) further includes a structural unit (a2) derived from an acrylate ester which has a lactone-containing cyclic group, in addition to the structural unit (a1).

Moreover, the component (A1) preferably includes a structural unit (a3) derived from an acrylate ester which has a polar group-containing aliphatic hydrocarbon group, in addition to the structural unit (a1), or the structural units (a1) and (a2).

Structural Unit (a1)

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) alkali-insoluble prior to dissociation, and then following dissociation by action of acid, causes the entire component (A1) to change to an alkali-soluble state. Generally, groups that form either a cyclic or chain-like tertiary alkyl ester with the carboxyl group of the (meth)acrylic acid; and acetal-type acid dissociable, dissolution inhibiting groups such as alkoxyalkyl groups are widely known.

Here, the term "tertiary alkyl ester" means a structure in which an ester is formed by substituting the hydrogen atom of a carboxyl group with a chain-like or cyclic alkyl group, and a tertiary carbon atom within the chain-like or cyclic alkyl group is bonded with the oxygen atom at the terminal of the carbonyloxy group (—C(O)—O—). In the tertiary alkyl ester, the bond of the oxygen atom with the tertiary carbon atom is cleaved by the action of acid.

Here, the chain-like or cyclic alkyl group may contain a substituent group.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of the tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" means a branched structure having no aromaticity. The "aliphatic branched, acid dissociable, dissolution inhibiting group" is not limited to groups (hydrocarbon groups) composed of carbon atoms and hydrogen atoms, and is preferably a hydrocarbon group. Further, the "hydrocarbon group" may be either saturated or unsaturated, and is preferably saturated.

Examples of aliphatic branched, acid dissociable, dissolution inhibiting groups include tertiary alkyl groups of 4 to 8 carbon atoms, and specific examples include a tert-butyl group, a tert-pentyl group and a tert-heptyl group.

The term "aliphatic cyclic group (alicyclic group)" means a monocyclic or polycyclic group which has no aromaticity. The "aliphatic cyclic group" within the structural unit (a1) may or may not contain a substituent group. Examples of substituent groups include a lower alkyl group of 1 to 5 carbon atoms, a fluorine atom, a fluorinated lower alkyl group of 1 to 5 carbon atoms, and an oxygen atom (=O).

The basic ring of the "aliphatic cyclic group" exclusive of substituent groups is not limited to groups (hydrocarbon groups) composed of carbon atoms and hydrogen atoms, and is preferably a hydrocarbon group. Further, the "hydrocarbon group" may be either saturated or unsaturated, and is preferably saturated. The "aliphatic cyclic group" is preferably a polycyclic group.

Examples of the aliphatic cyclic groups include groups in which one or more hydrogen atoms have been removed from a monocycloalkane or a polycycloalkane such as a bicycloalkane, tricycloalkane or tetracycloalkane in which a lower alkyl group, a fluorine atom or a fluorinated lower alkyl group may or may not be included as a substituent group. Specific examples include groups in which at least one hydrogen atom has been removed from a monocycloalkane such as cyclopentane and cyclohexane; and groups in which at least one hydrogen atom has been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples thereof include a 2-methyl-2-adamantyl group and a 2-ethyl-2-adamantyl group. Further, in the structural units represented by general formulae (a1"-1) to (a1"-6) shown below, groups bonded with the oxygen atom of the carbonyloxy group (—C(O)—O—), that is, groups having an aliphatic cyclic group such as an adamantyl group, a cyclohexyl group, a cyclopentyl group, a norbornyl group, a tricyclodecanyl group or a tetracyclodecanyl group, and a branched alkylene group having a tertiary carbon atom bonded thereto, can be exemplified.

[Chemical Formula 15]

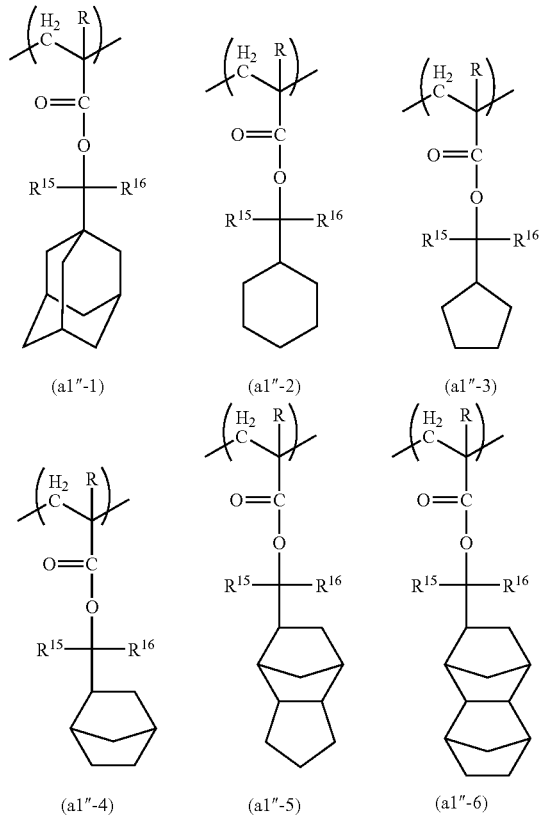

(wherein, R represents a hydrogen atom, a lower alkyl group or a halogenated lower alkyl group; and $R^{15}$ and $R^{16}$ each independently represents an alkyl group (which may be linear or branched, and is preferably an alkyl group of 1 to 5 carbon atoms).)

In the general formulae (a1"-1) to (a1"-6), the lower alkyl group or halogenated lower alkyl group for R are the same as the lower alkyl group or halogenated lower alkyl group which can be bonded with the α-position of the aforementioned acrylate ester.

An "acetal-type acid dissociable, dissolution inhibiting group" generally replaces a hydrogen atom at the terminal of an alkali-soluble group such as a carboxy group or a hydroxyl group, so as to be bonded with an oxygen atom. When acid is generated upon exposure, the generated acid acts to break the bond between the acetal-type acid dissociable, dissolution inhibiting group and the oxygen atom with which the acetal-type, acid dissociable, dissolution inhibiting group is bonded.

Examples of the acetal-type acid dissociable, dissolution inhibiting groups include groups represented by a general formula (p1) shown below.

[Chemical Formula 16]

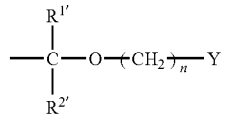

(p1)

(wherein, $R^{1'}$ and $R^{2'}$ each independently represents a hydrogen atom or a lower alkyl group; n represents an integer of 0 to 3; and Y represents a lower alkyl group or an aliphatic cyclic group.)

In the above formula, n is preferably an integer of 0 to 2, more preferably 0 or 1, and most preferably 0.

The lower alkyl group for $R^{1'}$ or $R^{2'}$ is the same as the lower alkyl groups described above in R. As the lower alkyl group of $R^{1'}$ or $R^{2'}$, a methyl group or an ethyl group is preferable, and a methyl group is most preferable.

In the present invention, at least one of $R^{1'}$ and $R^{2'}$ is preferably a hydrogen atom. That is, it is preferable that the acid dissociable, dissolution inhibiting group (p1) be a group represented by a general formula (p1-1) shown below.

[Chemical Formula 17]

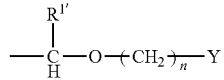

(p1-1)

(wherein, $R^{1'}$, n, and Y are as defined above.)

The lower alkyl group for Y is the same as the lower alkyl group described above in R.

As the aliphatic cyclic group for Y, any of the aliphatic monocyclic or polycyclic groups which have been proposed for conventional ArF resists and the like can be used by being appropriately selected from those. For example, the same groups described above in the "aliphatic cyclic group" can be exemplified.

Further, as the acetal-type, acid dissociable, dissolution inhibiting group, groups represented by general formula (p2) shown below can also be exemplified.

[Chemical Formula 18]

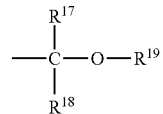

(p2)

(wherein $R^{17}$ and $R^{18}$ each independently represents a linear or branched alkyl group or a hydrogen atom; and $R^{19}$ represents a linear, branched, or cyclic alkyl group. Alternately, $R^{17}$ and $R^{19}$ each independently represents a linear or branched alkylene group, wherein the terminal of $R^{17}$ may be bonded with the terminal of $R^{19}$ thereby forming a ring.)

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly preferable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Specific examples of the cyclic alkyl group include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent group. Specific examples thereof include groups in which one or more hydrogen atoms have been removed from a monocycloalkane such as cyclopentane and cyclohexane, and a polycycloalkane such as adamantane, norbornane, isobornane, tricyclodecane, and tetracyclododecane. Of these, a group in which one or more hydrogen atoms have been removed from adamantane is preferable.

In the general formula (p2), $R^{17}$ and $R^{19}$ may each independently represent a linear or branched alkylene group (preferably an alkylene group of 1 to 5 carbon atoms), and the terminal of $R^{19}$ may be bonded with the terminal of $R^{17}$.

In such a case, a cyclic group is formed by $R^{17}$, $R^{19}$, the oxygen atom with which $R^{19}$ is bonded, and the carbon atom with which the oxygen atom and $R^{17}$ are bonded. Such a cyclic group is preferably a 4- to 7-membered ring, and more preferably a 4- to 6-membered ring. Specific examples of the cyclic group include a tetrahydropyranyl group and a tetrahydrofuranyl group.

As the structural unit (a1), it is preferable to use at least one member selected from the group consisting of structural units represented by a general formula (a1-0-1) shown below and structural units represented by a general formula (a1-0-2) shown below.

[Chemical Formula 19]

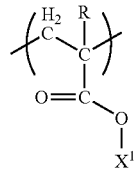

(a1-0-1)

(wherein, R represents a hydrogen atom, a lower alkyl group or a halogenated lower alkyl group; and $X^1$ represents an acid dissociable, dissolution inhibiting group.)

[Chemical Formula 20]

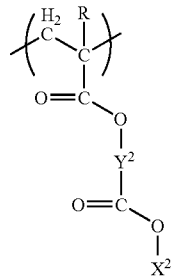

(a1-0-2)

(wherein, R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.)

In the general formula (a1-0-1), the lower alkyl group or halogenated lower alkyl group of R are the same as the lower alkyl group or halogenated lower alkyl group which can be bonded with the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In the general formula (a1-0-2), R is as defined above.

$X^2$ is the same as $X^1$ described in the general formula (a1-0-1).

$Y^2$ is preferably an alkylene group of 1 to 10 carbon atoms or a bivalent aliphatic cyclic group. As the aliphatic cyclic group, the same as those described in "aliphatic cyclic group" can be used, with the exception that two or more hydrogen atoms are removed.

When $Y^2$ represents an alkylene group of 1 to 10 carbon atoms, it is more preferable that the number of carbon atoms be 1 to 6, still more preferably 1 to 4, and most preferably 1 to 3.

When $Y^2$ represents a divalent aliphatic cyclic group, it is particularly preferable that the divalent aliphatic cyclic group be a group in which two or more hydrogen atoms have been removed from a cyclopentane, a cyclohexane, a norbornane, an isobornane, an adamantane, a tricyclodecane or a tetracyclododecane.

Specific examples of the structural unit (a1) include structural units represented by the general formulae (a1-1) to (a1-4) shown below.

[Chemical Formula 21]

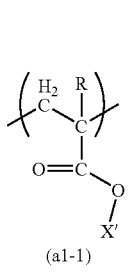

(a1-1)

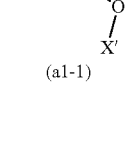

(a1-2)

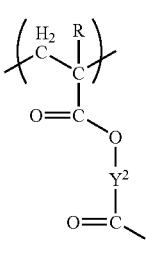

(a1-3)

-continued

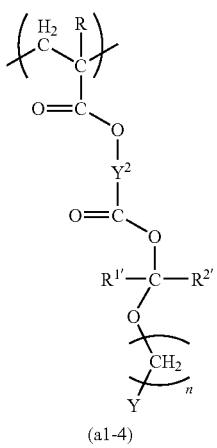

(a1-4)

(wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; and $R^{1'}$ and $R^{2'}$ each independently represents a hydrogen atom or a lower alkyl group of 1 to 5 carbon atoms.)

In the formula, X' is the same as a tertiary alkyl ester-type acid dissociable, dissolution inhibiting group described in $X^1$.

$R^{1'}$, $R^{2'}$, n, and Y are the same as $R^{1'}$, $R^{2'}$, n, and Y in the general formula (p1) shown above in "acetal-type acid dissociable, dissolution inhibiting group".

$Y^2$ is the same as $Y^2$ in the general formula (a1-0-2).

Specific examples of structural units represented by the general formulae (a1-1) and (a1-4) shown above include the following.

[Chemical Formula 22]

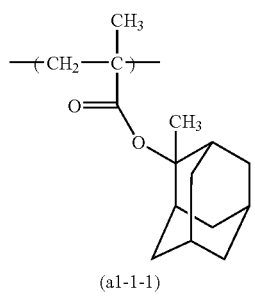
(a1-1-1)

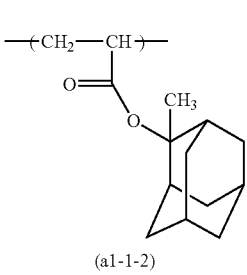
(a1-1-2)

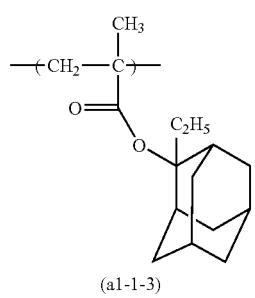
(a1-1-3)

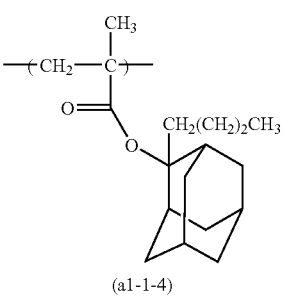
(a1-1-4)

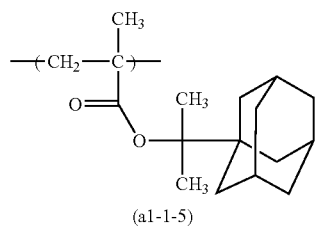
(a1-1-5)

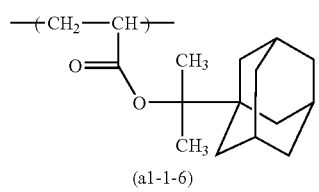
(a1-1-6)

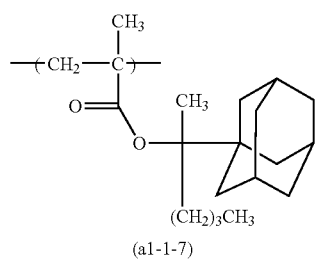
(a1-1-7)

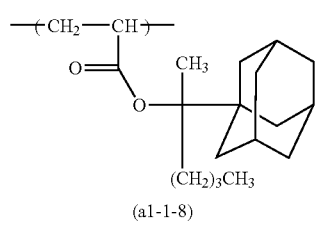
(a1-1-8)

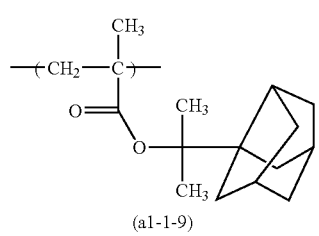
(a1-1-9)

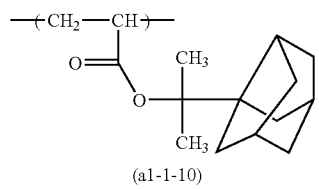
(a1-1-10)

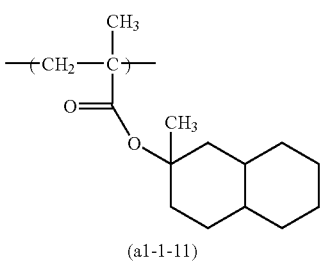
(a1-1-11)

-continued (a1-1-12)

(a1-1-13)

(a1-1-14)

(a1-1-15)

(a1-1-16)

[Chemical Formula 23]

(a1-1-17)   (a1-1-18)

-continued (a1-1-19)

(a1-1-20)

(a1-1-21)   (a1-1-22)

(a1-1-23)   (a1-1-24)

(a1-1-25)   (a1-1-26)

(a1-1-27)   (a1-1-28)

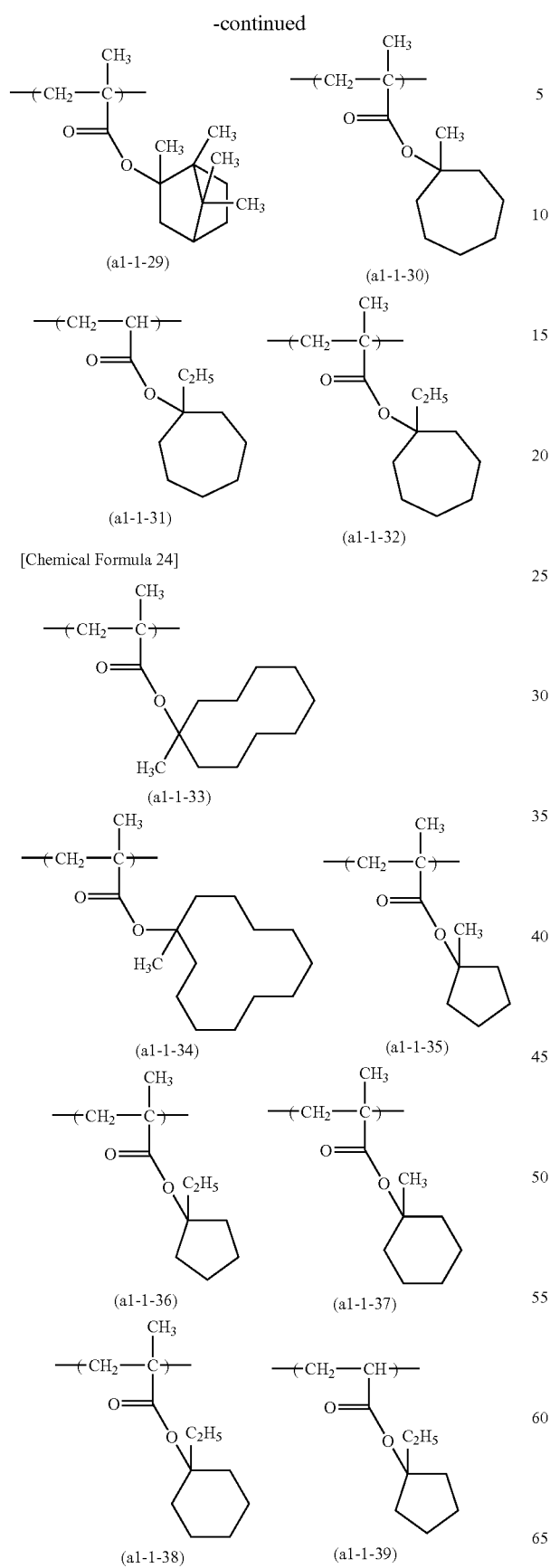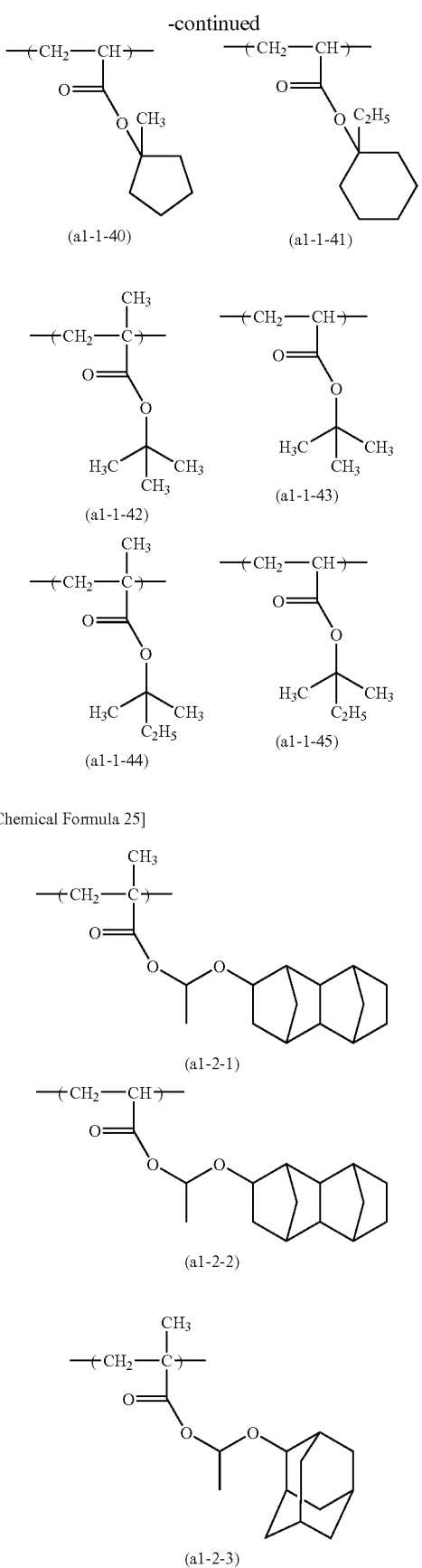

-continued
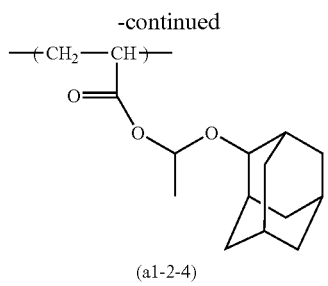
(a1-2-4)
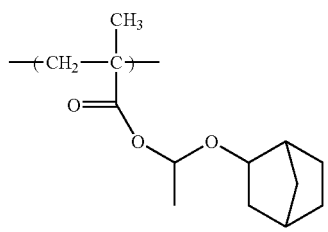
(a1-2-5)
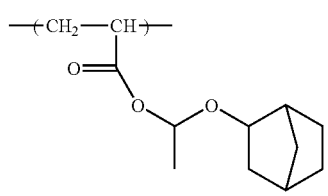
(a1-2-6)
[Chemical Formula 26]
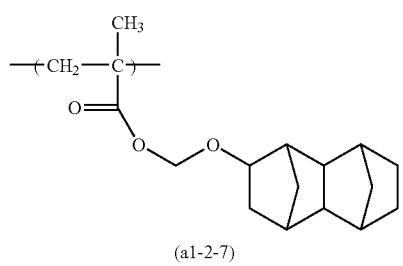
(a1-2-7)
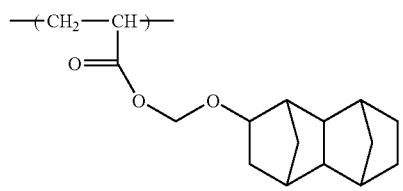
(a1-2-8)
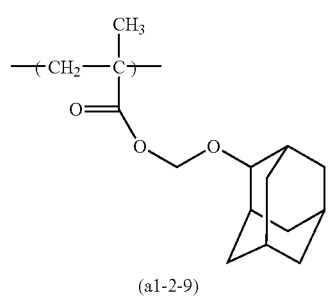
(a1-2-9)
-continued
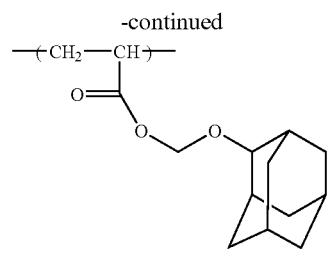
(a1-2-10)
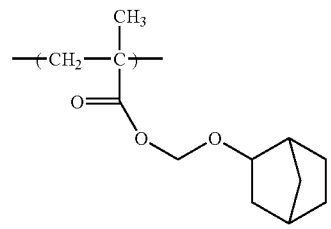
(a1-2-11)
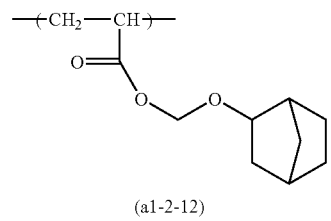
(a1-2-12)
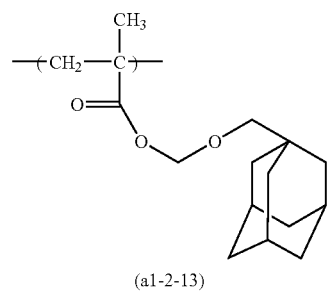
(a1-2-13)
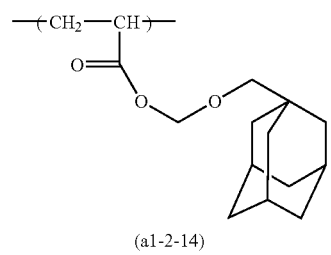
(a1-2-14)
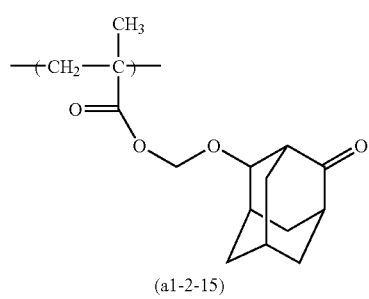
(a1-2-15)

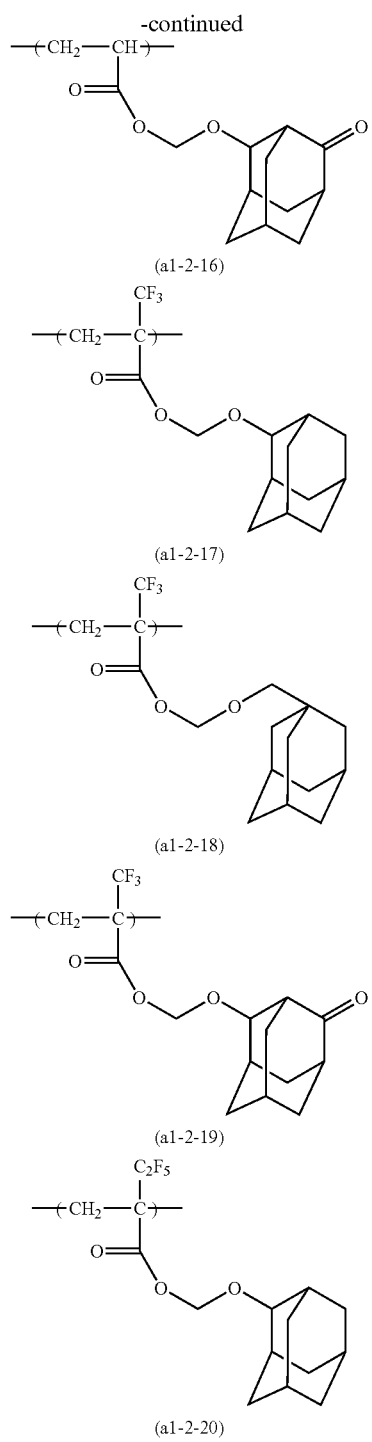
(a1-2-16)
(a1-2-17)
(a1-2-18)
(a1-2-19)
(a1-2-20)
[Chemical Formula 27]
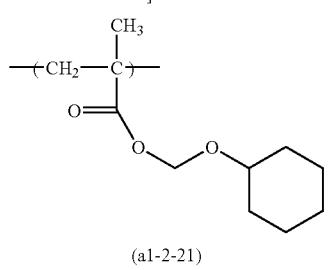
(a1-2-21)
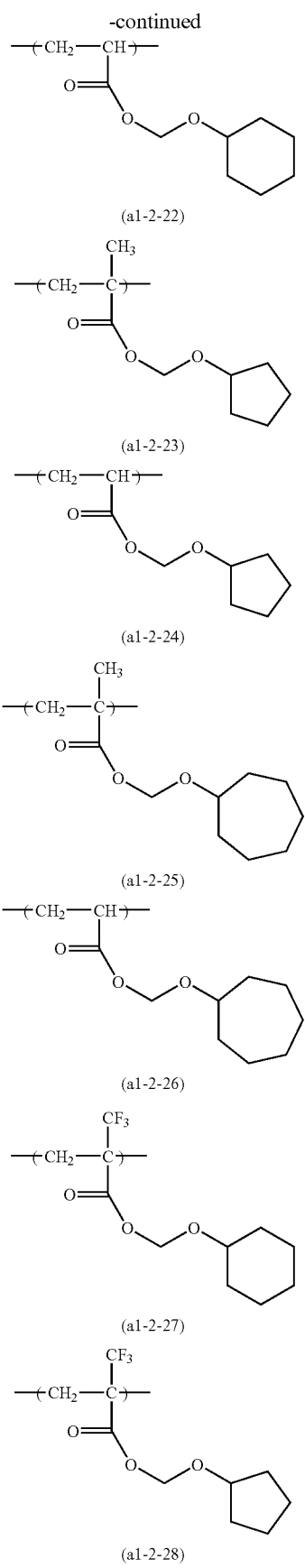
(a1-2-22)
(a1-2-23)
(a1-2-24)
(a1-2-25)
(a1-2-26)
(a1-2-27)
(a1-2-28)

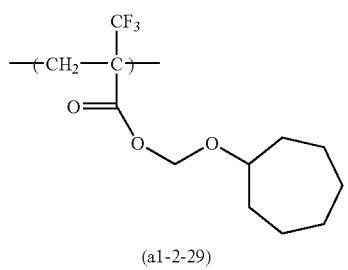
(a1-2-29)
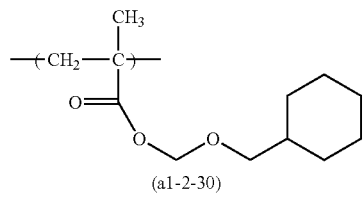
(a1-2-30)
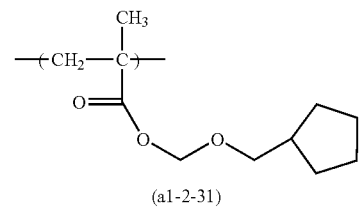
(a1-2-31)
[Chemical Formula 28]
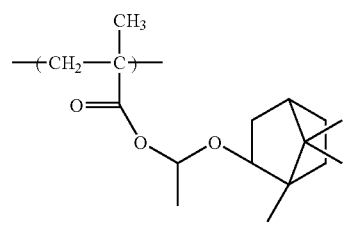
(a1-2-32)
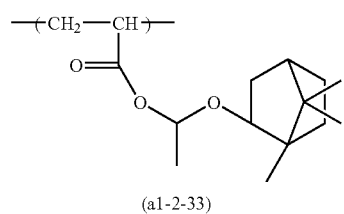
(a1-2-33)
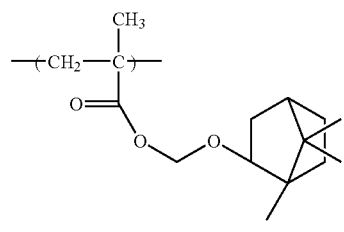
(a1-2-34)
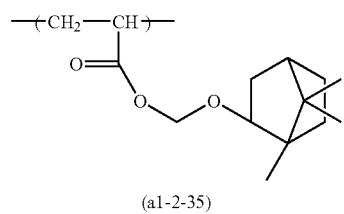
(a1-2-35)
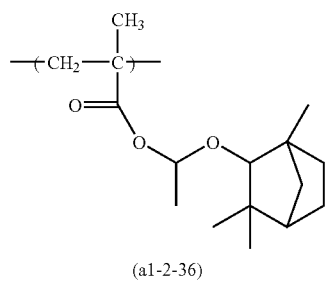
(a1-2-36)
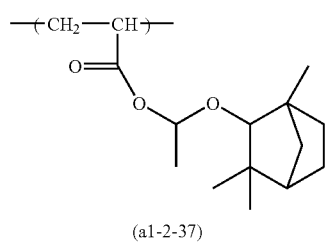
(a1-2-37)
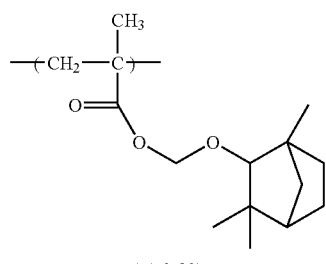
(a1-2-38)
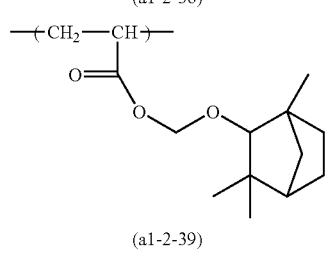
(a1-2-39)
[Chemical Formula 29]
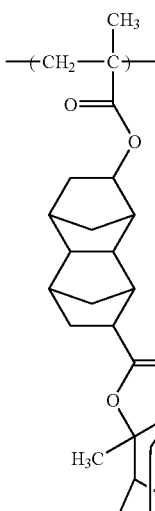
(a1-3-1)
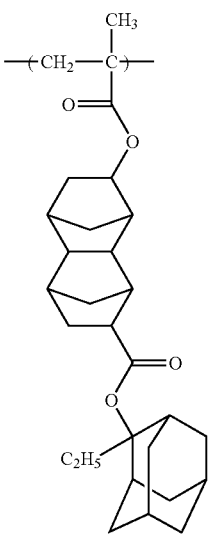
(a1-3-2)

-continued
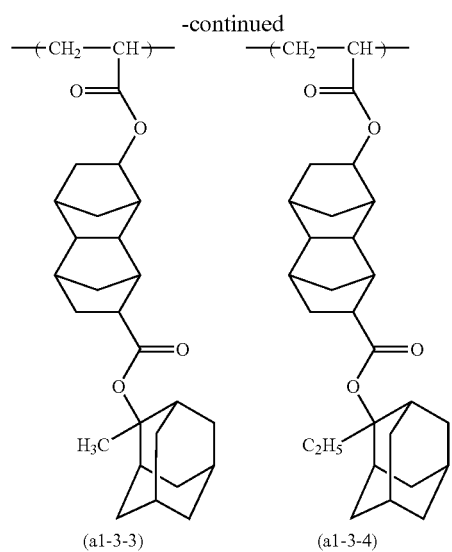
(a1-3-3) (a1-3-4)
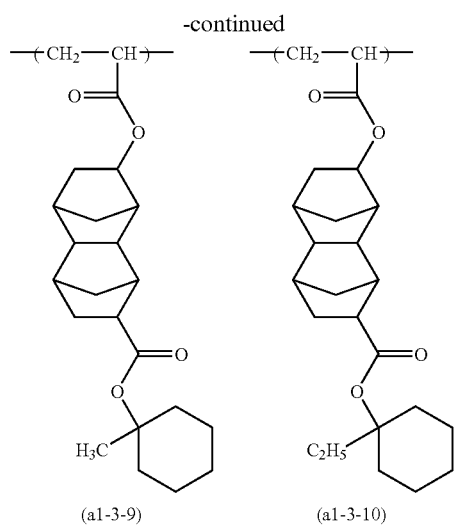
(a1-3-9) (a1-3-10)
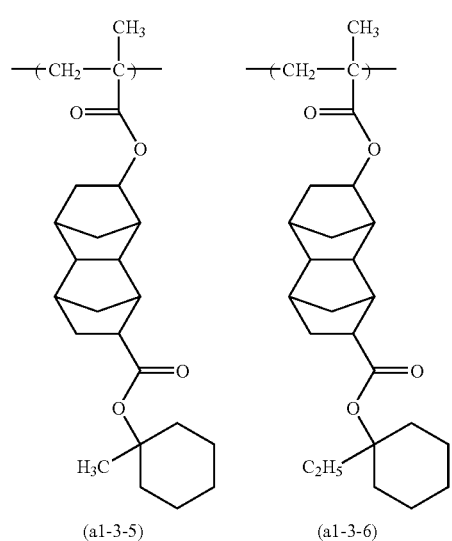
(a1-3-5) (a1-3-6)
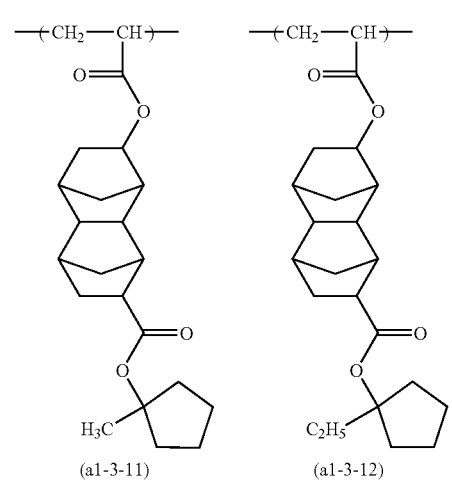
(a1-3-11) (a1-3-12)
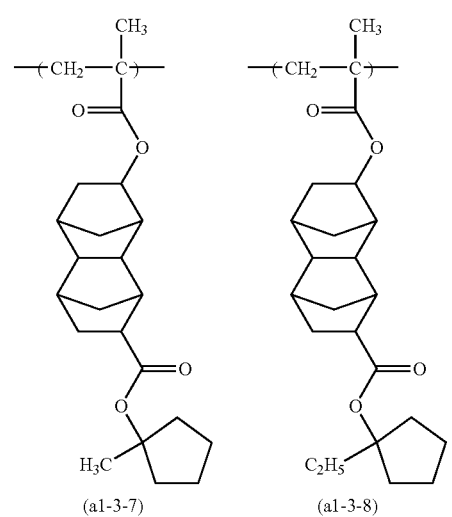
(a1-3-7) (a1-3-8)
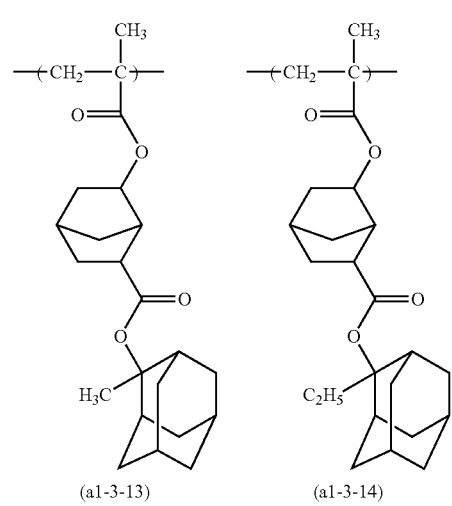
(a1-3-13) (a1-3-14)

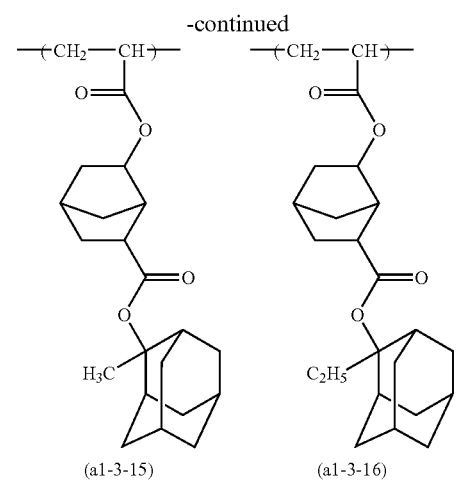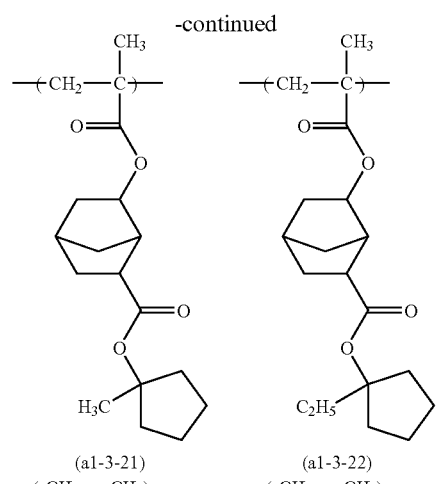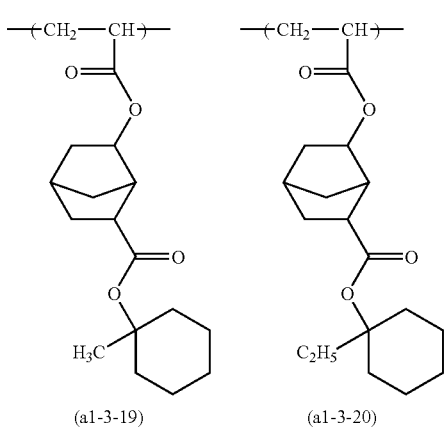

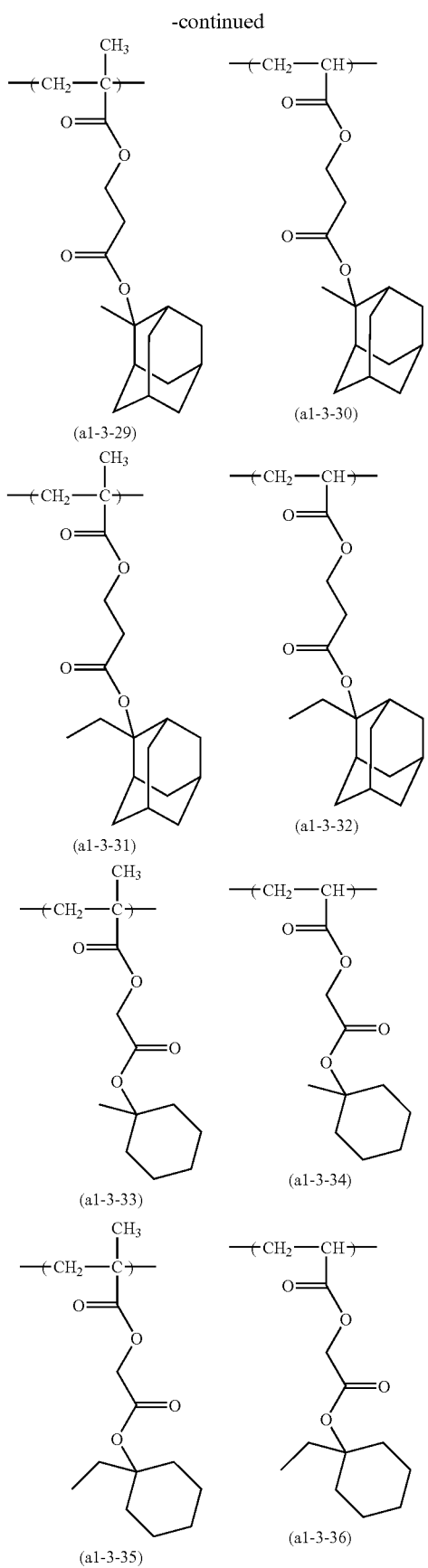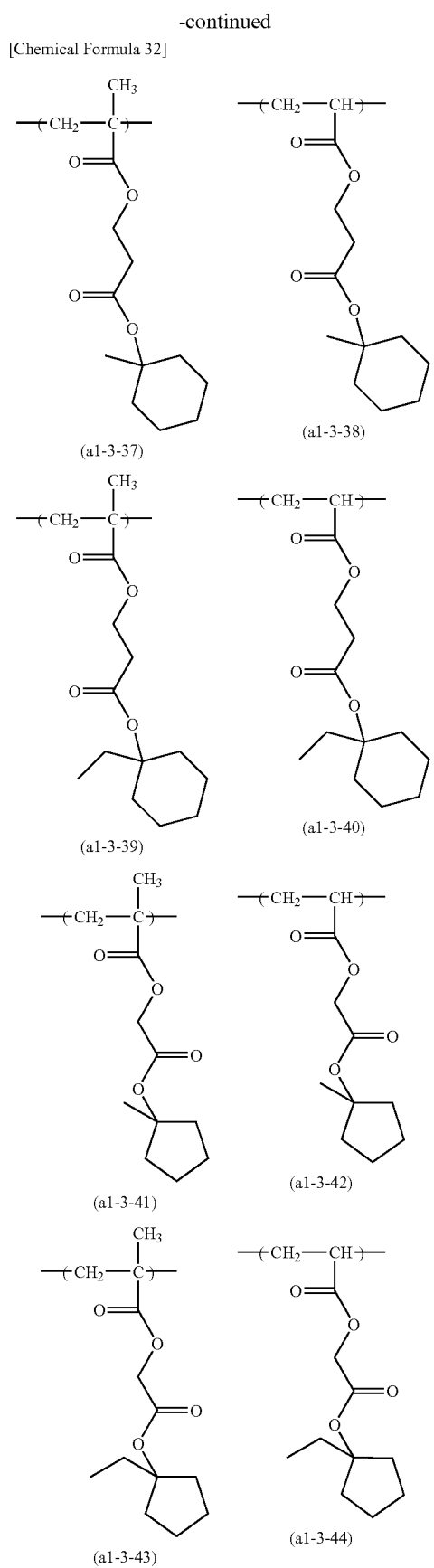

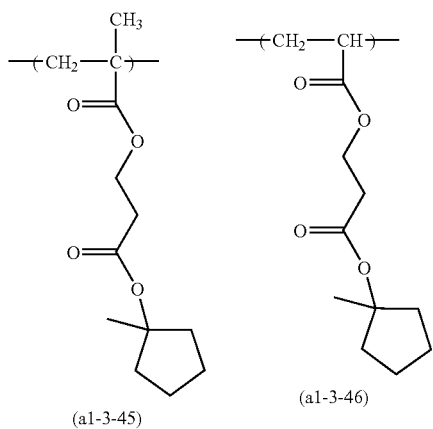
(a1-3-45) (a1-3-46)
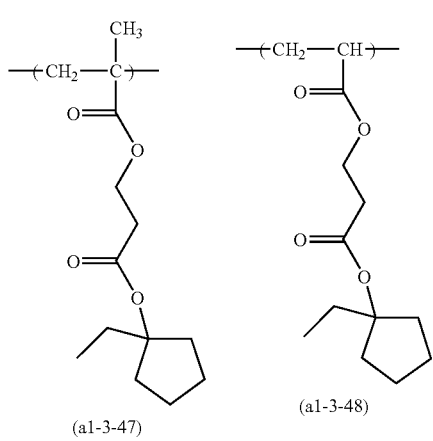
(a1-3-47) (a1-3-48)
[Chemical Formula 33]
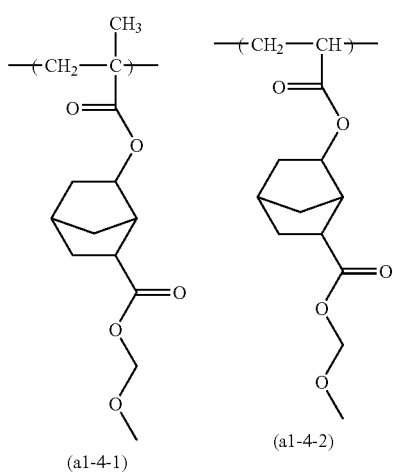
(a1-4-1) (a1-4-2)
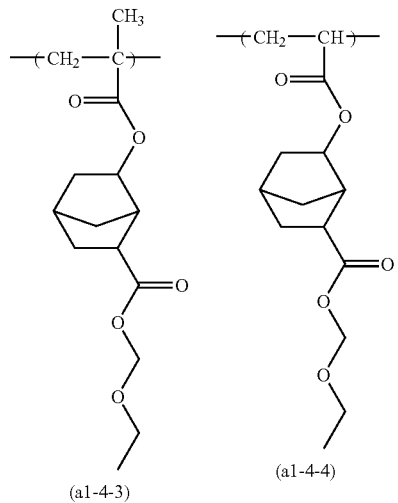
(a1-4-3) (a1-4-4)
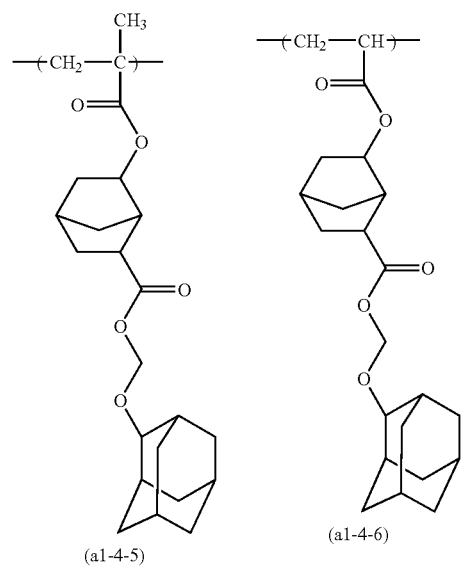
(a1-4-5) (a1-4-6)
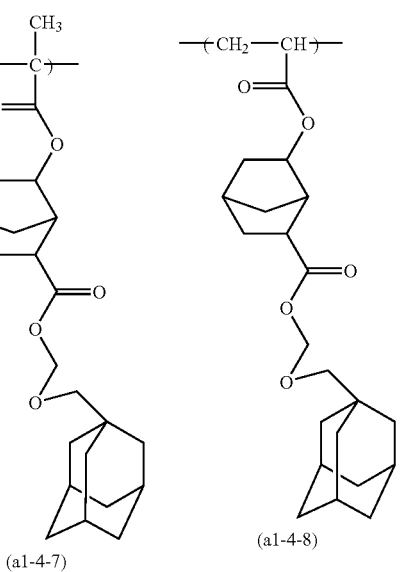
(a1-4-7) (a1-4-8)

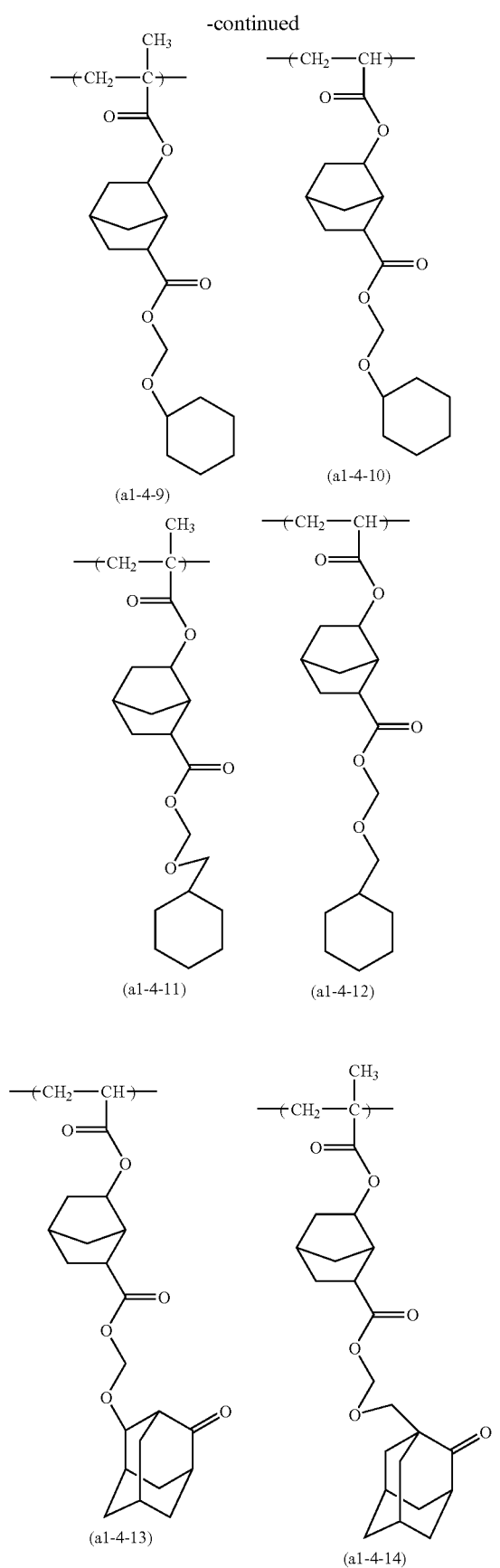

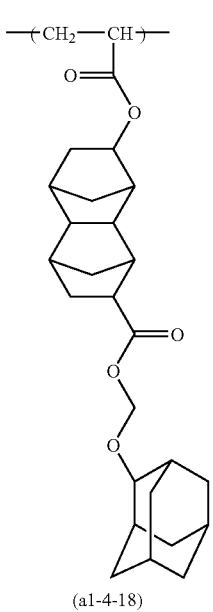
(a1-4-18)
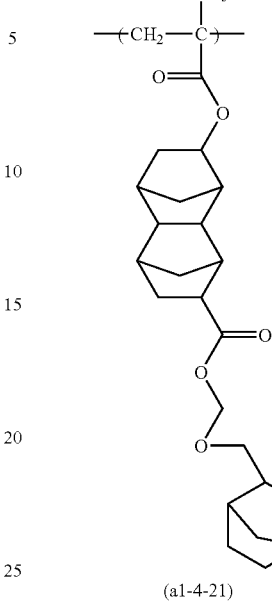
(a1-4-21)  (a1-4-22)
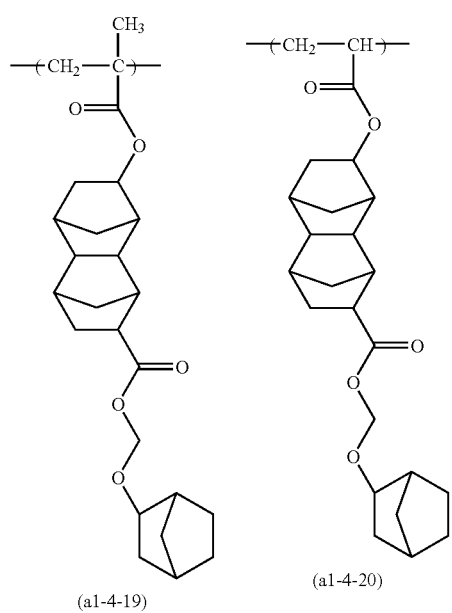
(a1-4-19)  (a1-4-20)
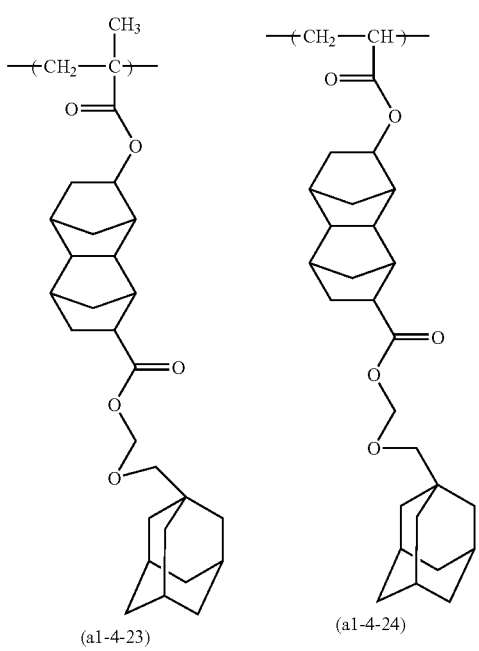
(a1-4-23)  (a1-4-24)

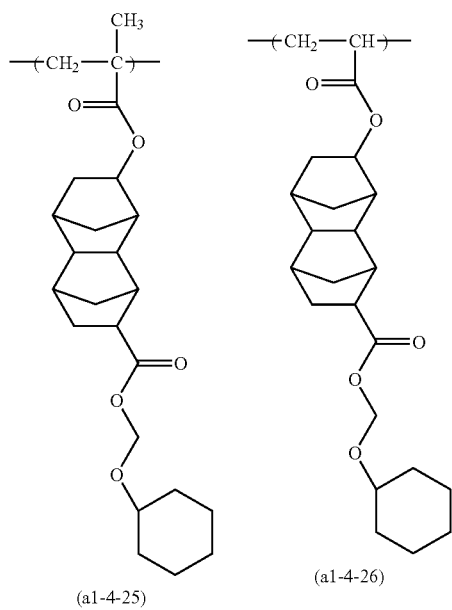

(a1-4-25) (a1-4-26)

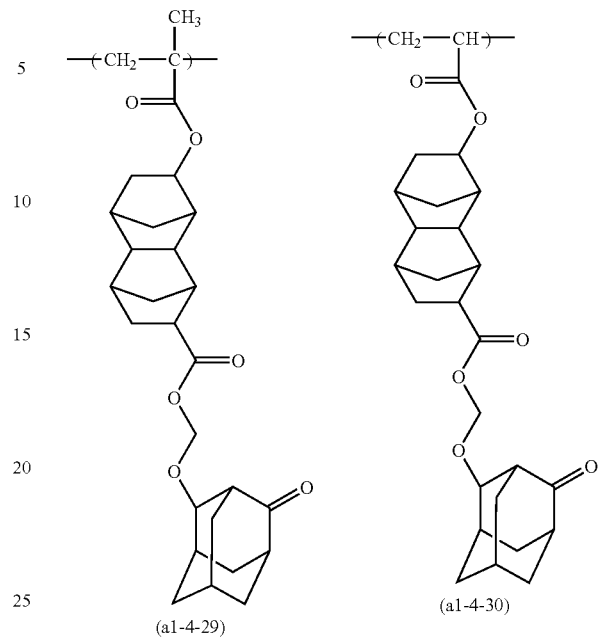

(a1-4-29) (a1-4-30)

The structural unit (a1) can be used alone, or in combinations of two or more different units.

Of these, a structural unit represented by the general formula (a1-1) is preferable, and it is more preferable to use at least one kind selected from the group consisting of the general formula (a1-1-1) to (a1-1-6), and (a1-1-35) to (a1-1-41).

Further, as the structural unit (a1), structural units represented by a general formula (a1-1-01) shown below which includes the structural units represented by formulae (a1-1-1) to (a1-1-4), and structural units represented by a general formula (a1-1-02) shown below which includes the structural units represented by formulae (a1-1-35) to (a1-1-41) are also preferable.

[Chemical Formula 35]

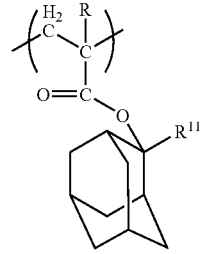

(a1-1-01)

(a1-4-27) (a1-4-28)

(in the formula, R represents a hydrogen atom, a lower alkyl group or a halogenated lower alkyl group; and $R^{11}$ represents a lower alkyl group.)

[Chemical Formula 36]

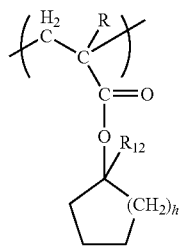

(a1-1-02)

(in the formula, R represents a hydrogen atom, a lower alkyl group, or a halogenated lower alkyl group; $R^{12}$ represents a lower alkyl group; and h represents an integer of 1 to 3.)

In the general formula (a1-1-01), R is as defined above.

The lower alkyl group for $R^{11}$ is the same as the lower alkyl group described above in R, and is preferably a methyl group or an ethyl group.

In the general formula (a1-1-02), R is as defined above.

The lower alkyl group for $R^{12}$ is the same as the lower alkyl group described above in R. $R^{12}$ is preferably a methyl group or an ethyl group, and most preferably an ethyl group. h is preferably 1 or 2, and most preferably 2.

The structural unit (a1) can be used alone, or in combinations of two or more different units.

In the component (A1), the amount of the structural unit (a1) is preferably 10 to 80 mol %, more preferably 20 to 70 mol %, and still more preferably 25 to 50 mol %, based on the combined total of all structural units constituting the component (A1). When this proportion is not less than the lower limit in the above range, then a pattern can be easily formed using a positive resist composition which includes the structural unit (a1), whereas when the proportion is not more than the upper limit in the above range, a good quantitative balance with the other structural units can be attained.

Structural Unit (a2)

Structural unit (a2) is a structural unit derived from an acrylate ester which has a lactone-containing cyclic group.

Here, the term "lactone-containing cyclic group" means a cyclic group containing a single ring (lactone ring) which has a "—O—C(O)—" structure. This lactone ring is counted as the first ring, and groups that contain only the lactone ring are referred to as monocyclic groups, whereas groups that also contain other ring structures are described as polycyclic groups regardless of the structure of the other rings.

In the case of using the component (A1) to form a resist film, the lactone-containing cyclic group of the structural unit (a2) is effective at improving the adhesion between the resist film and a substrate, and improving compatibility with the aqueous developing solution.

The structural unit (a2) can be used arbitrarily without any particular restriction.

Specific examples of the lactone-containing monocyclic group include a group in which one hydrogen atom is eliminated from γ-butyrolactone. Furthermore, specific examples of the lactone-containing polycyclic group include a group in which one hydrogen atom is eliminated from a bicycloalkane, a tricycloalkane, or a tetracycloalkane which contains a lactone ring.

Specific examples of the structural unit (a2) include structural units represented by the general formulae (a2-1) to (a2-5) shown below.

[Chemical Formula 37]

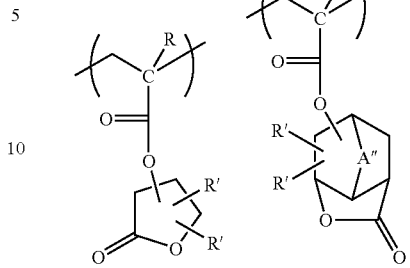

(a2-1)          (a2-2)

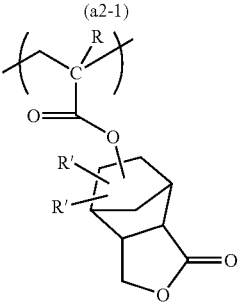 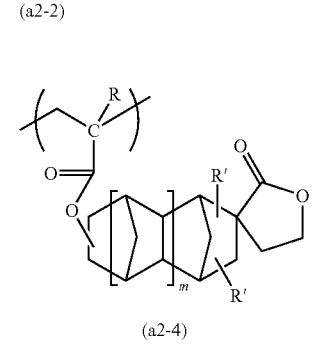

(a2-3)          (a2-4)

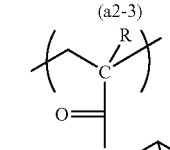
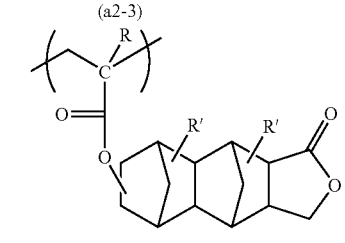
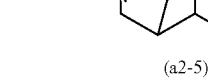

(a2-5)

(wherein, R represents a hydrogen atom, a lower alkyl group, or a halogenated lower alkyl group; R' represents a hydrogen atom, a lower alkyl group, an alkoxy group of 1 to 5 carbon atoms, or the group of —COOR", wherein R" of —COOR" for R' represents a hydrogen atom, or a linear, branched, or cyclic alkyl group of 1 to 15 carbon atoms; m represents an integer of 0 or 1; and A" represents an alkylene group of 1 to 5 carbon atoms or an oxygen atom.)

R in the general formula (a2-1) to (a2-5) is the same as R described above in the structural unit (a1).

The lower alkyl group for R' is the same as the lower alkyl group for R described above in the structural unit (a1).

In the case that R" is a linear or branched alkyl group, the number of carbon atoms is preferably 1 to 10, and more preferably 1 to 5.

In the case that R" is a cyclic alkyl group, the number of carbon atoms is preferably 3 to 15, more preferably 4 to 12, and most preferably 5 to 10. Specific examples of the cyclic alkyl group include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent group. Specific examples thereof include groups in which one or more hydrogen atoms have been removed from a monocycloalkane such as cyclopentane and cyclohexane, and a polycycloalkane such as adamantane, norbornane, isobornane, tricyclodecane, and tetracyclododecane.

Specific examples of the alkylene group of 1 to 5 carbon atoms for A" include a methylene group, an ethylene group, an n-propylene group, and an isopropylene group.

In the general formula (a2-1) to (a2-5), R' is preferably a hydrogen atom in terms of industrial availability.

Specific examples of the structural units represented by the general formulae (a2-1) to (a2-5) include the following.

[Chemical Formula 38]

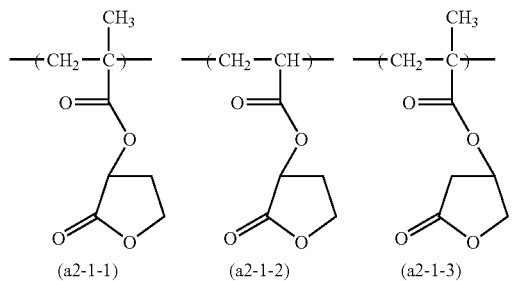

(a2-1-1)  (a2-1-2)  (a2-1-3)

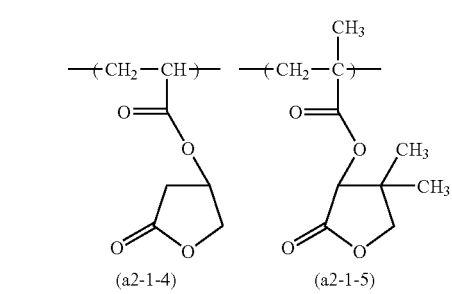

(a2-1-4)  (a2-1-5)

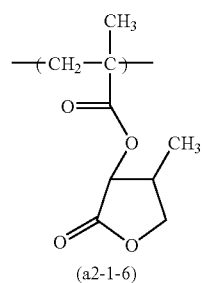

(a2-1-6)

[Chemical Formula 39]

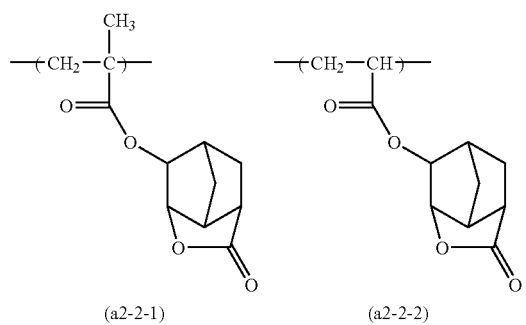

(a2-2-1)  (a2-2-2)

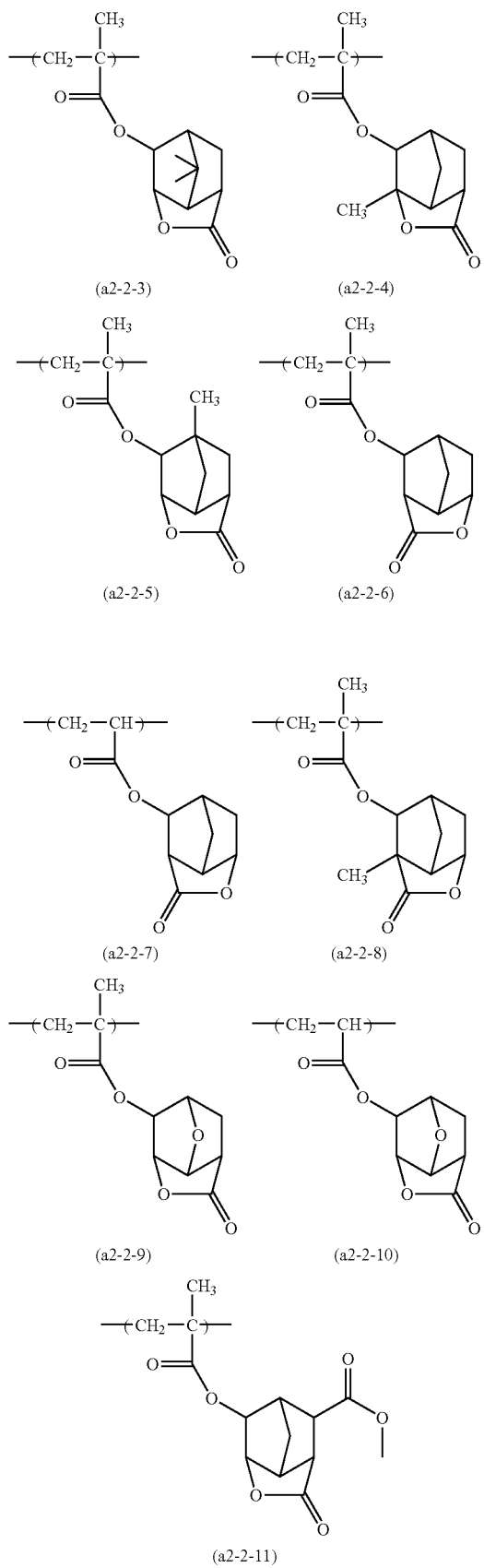

-continued (a2-2-3)  (a2-2-4)

(a2-2-5)  (a2-2-6)

(a2-2-7)  (a2-2-8)

(a2-2-9)  (a2-2-10)

(a2-2-11)

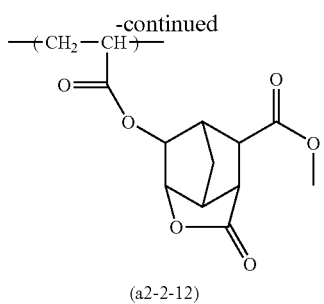
(a2-2-12)
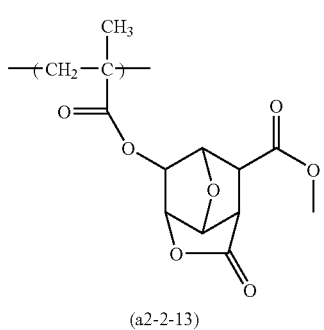
(a2-2-13)
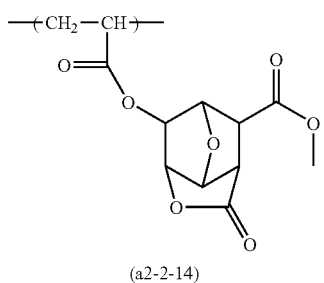
(a2-2-14)
[Chemical Formula 40]
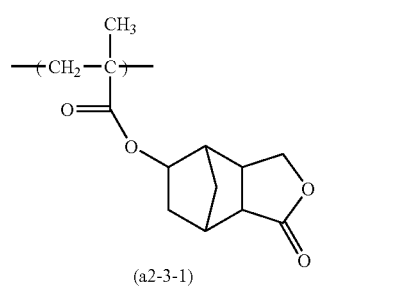
(a2-3-1)
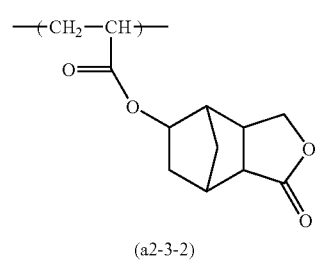
(a2-3-2)
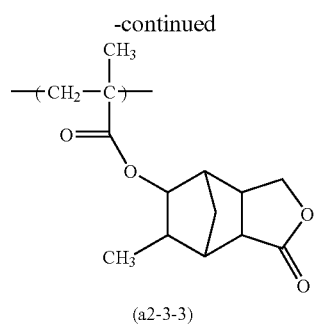
(a2-3-3)
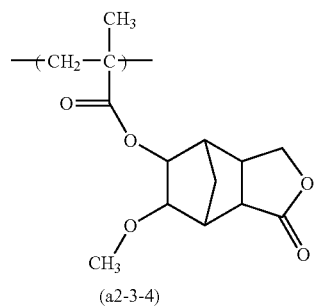
(a2-3-4)
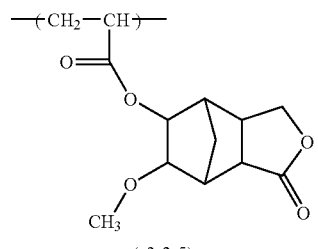
(a2-3-5)
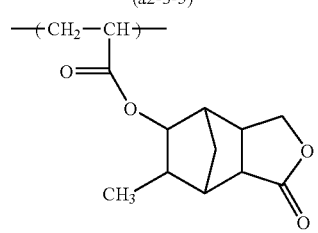
(a2-3-6)
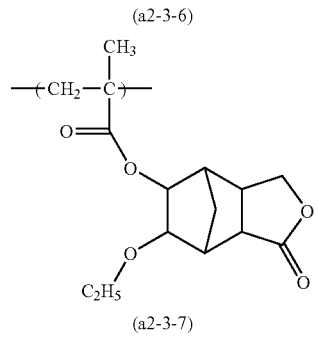
(a2-3-7)
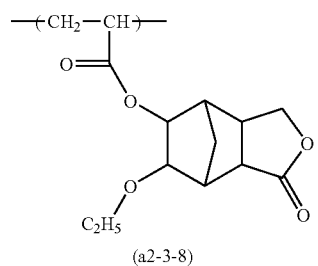
(a2-3-8)

-continued
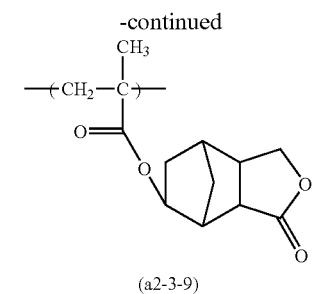
(a2-3-9)
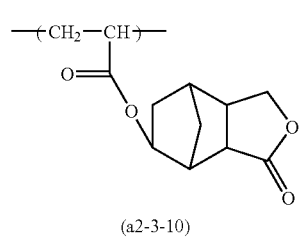
(a2-3-10)
[Chemical Formula 41]
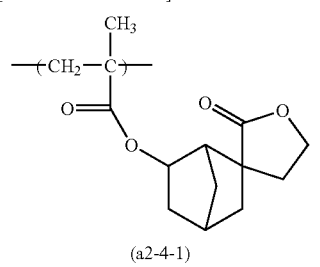
(a2-4-1)
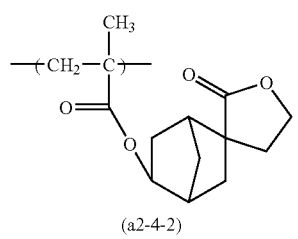
(a2-4-2)
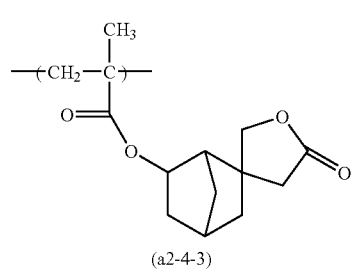
(a2-4-3)
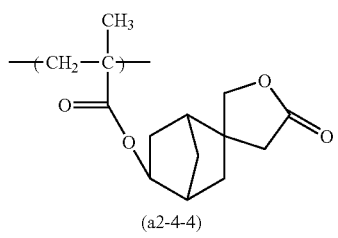
(a2-4-4)
-continued
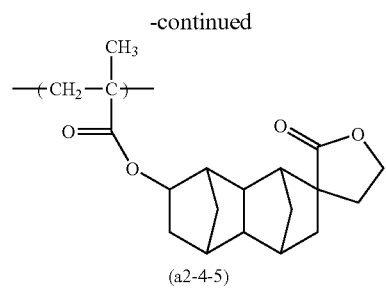
(a2-4-5)
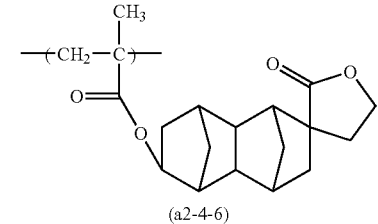
(a2-4-6)
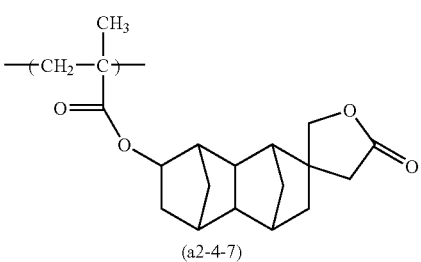
(a2-4-7)
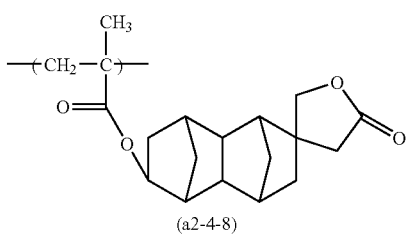
(a2-4-8)
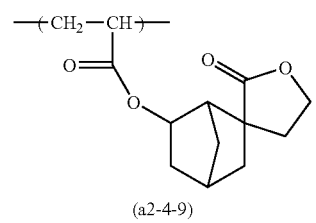
(a2-4-9)
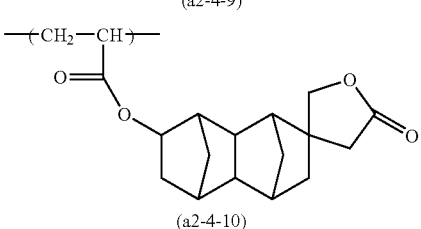
(a2-4-10)
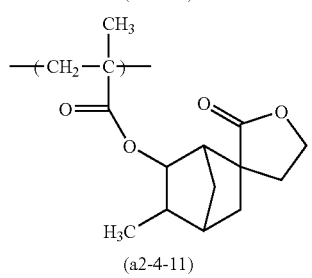
(a2-4-11)

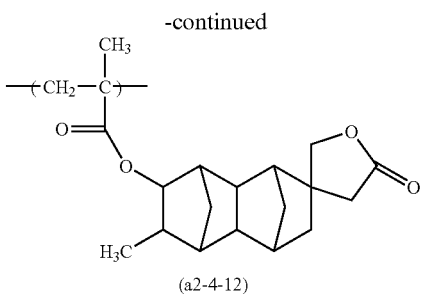

(a2-4-12)

[Chemical Formula 42]

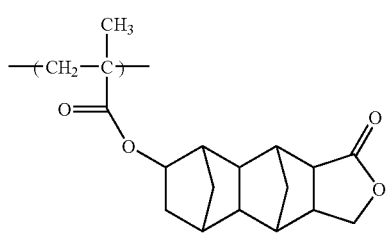

(a2-5-1)

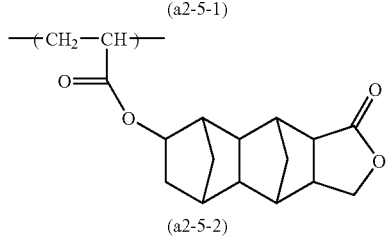

(a2-5-2)

(a2-5-3)

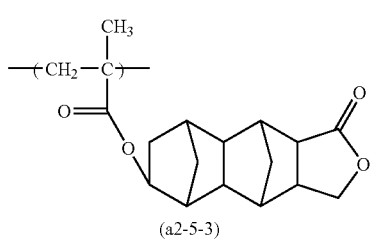

(a2-5-4)

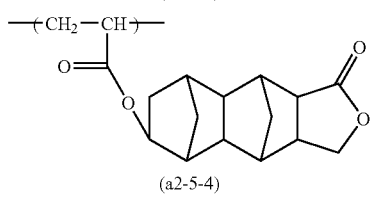

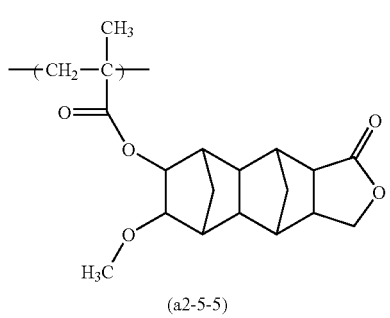

(a2-5-5)

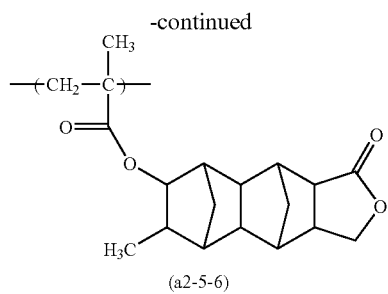

(a2-5-6)

The structural unit (a2) is preferably at least one kind selected from the group consisting of the structural units represented by the general formulae (a2-1) to (a2-5), and more preferably at least one kind selected from the group consisting of the structural units represented by the general formula (a2-1) to (a2-3). Of these, at least one kind selected from the group consisting of the structural units represented by (a2-1-1), (a2-2-1), (a2-2-2), (a2-3-1), (a2-3-2), (a2-3-9) and (a2-3-10) is particularly preferable.

The structural unit (a2) can be used alone, or in combinations of two or more different units.

In the component (A1), the amount of the structural unit (a2) is preferably 5 to 60 mol %, more preferably 10 to 50 mol %, and still more preferably 20 to 50 mol %, based on the combined total of all structural units constituting the component (A1). When this proportion is not less than the lower limit in the above range, then the effect by containing the structural unit (a2) can be sufficiently obtained. When the proportion is not more than the upper limit in the above range, a good quantitative balance with the other structural units can be attained.

Structural Unit (a3)

Structural unit (a3) is a structural unit derived from an acrylate ester which has a polar group-containing aliphatic hydrocarbon group.

By including the structural unit (a3), the hydrophilicity of the component (A1) is improved, and hence, the compatibility of the component (A1) with the developing solution is improved. As a result, the solubility of the exposed portions in an alkali developing solution improves, which contributes to favorable improvements in the resolution.

Examples of the polar group include a hydroxyl group, a cyano group, a carboxyl group, a hydroxyalkyl group in which a part of the hydrogen atoms in an alkyl group is substituted with fluorine atoms. Of these, a hydroxyl group is particularly preferable.

Examples of the aliphatic hydrocarbon group include a linear or branched hydrocarbon group of 1 to 10 carbon atoms (preferably an alkylene group), and a polycyclic aliphatic hydrocarbon group (polycyclic group). The polycyclic group can be appropriately selected from the multitude of structural units proposed as resins in resist compositions for ArF excimer lasers and the like. The polycyclic group preferably has 7 to 30 carbon atoms.

Of these, a structural unit derived from an acrylate ester having the polycyclic aliphatic group which contains a hydroxyl group, cyano group, a carboxyl group, or a hydroxyalkyl group in which a part of the hydrogen atoms within an alkyl group has been substituted with fluorine atoms is more preferable. Examples of the polycyclic group include groups in which two or more hydrogen atoms have been removed from a bicycloalkane, a tricycloalkane, a tetracycloalkane, or the like. Specific examples include a group in which two or more hydrogen atoms have been removed from a polycycloalkane such as an adamantane, a norbornane, an isobornane, a tricyclodecane, or a tetracyclododecane. Of these polycyclic groups, a group in which two or more hydrogen atoms have been removed from an adamantane, a norbornane, or a tetracyclododecane is industrially preferable.

As the structural unit (a3), for example, a structural unit derived from a hydroxyethyl ester of acrylic acid is preferable, when the hydrocarbon group within the polar group-containing aliphatic hydrocarbon group is a linear or branched hydrocarbon group of 1 to 10 carbon atoms. On the other hand, a structural unit represented by a general formula (a3-1), (a3-2), or (a3-3) shown below is preferable, when the hydrocarbon group is a polycyclic group.

[Chemical Formula 43]

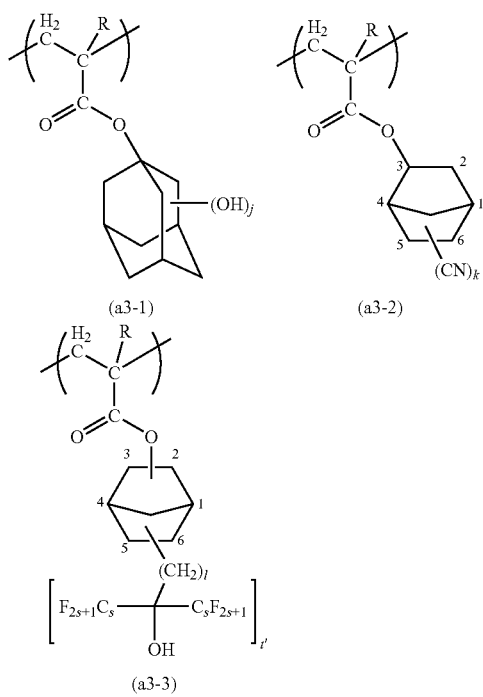

(wherein, R is as defined above; j represents an integer of 1 to 3; k represents an integer of 1 to 3; t' represents an integer of 1 to 3; l represents an integer of 1 to 5; and s represents an integer of 1 to 3.)

In the general formula (a3-1), j is preferably 1 or 2, and more preferably 1. In the case that j is 2, a structural unit in which a hydroxyl group is bonded with the 3-position and 5-position of the adamantyl group is preferable. In the case that j is 1, a structural unit in which a hydroxyl group is bonded with the 3-position of the adamantyl group is preferable.

Of these, it is preferable that j be 1, and the hydroxyl group be bonded with the 3-position of the adamantyl group.

In the general formula (a3-2), k is preferably 1. In the general formula (a3-2), a cyano group is preferably bonded with the 5-position or 6-position of the norbornyl group.

In the general formula (a3-3), t' is preferably 1. l is preferably 1. s is preferably 1. Further, in the general formula (a3-3), it is preferable that a 2-norbonyl group or 3-norbonyl group be bonded at the terminal of the carboxy group of the acrylic acid. It is preferable that a fluorinated alkyl alcohol be bonded with the 5-position or 6-position of the norbornyl group.

The structural unit (a3) can be used alone, or in combinations of two or more different units.

In the component (A1), the amount of the structural unit (a3) is preferably 5 to 50 mol %, more preferably 5 to 40 mol %, and still more preferably 5 to 25 mol %, based on the combined total of all structural units constituting the component (A1). When this proportion is not less than the lower limit in the above range, then the effect by containing the structural unit (a3) can be sufficiently obtained, whereas when the proportion is not more than the upper limit in the above range, good quantitative balance with the other components can be attained.

Structural Unit (a4)

The component (A1) may also have a structural unit (a4) which is different from the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

The structural unit (a4) is preferably, for example, a structural unit derived from an acrylate ester containing a non-acid-dissociable aliphatic polycyclic group. Examples of the polycyclic group include the same as those described above in the structural unit (a1), and any of the multitude of conventional polycyclic groups used within the resin component of resist compositions for ArF excimer lasers or KrF excimer lasers (and preferably for ArF excimer lasers) can be used.

In particular, at least one group selected from amongst a tricyclodecanyl group, an adamantyl group, a tetracyclododecanyl group, an isobornyl group, and a norbornyl group is preferable in terms of industrial availability and the like. These polycyclic groups may contain a linear or branched alkyl group of 1 to 5 carbon atoms as a substituent group.

Specific examples of the structural unit (a4) include a structural unit represented by general formulae (a4-1) to (a4-5) shown below.

[Chemical Formula 44]

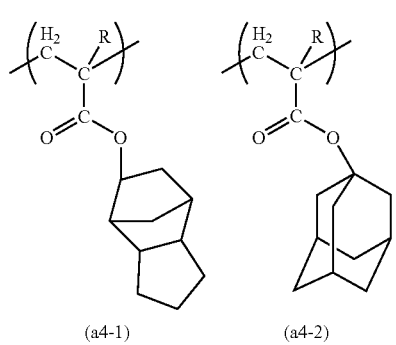

-continued

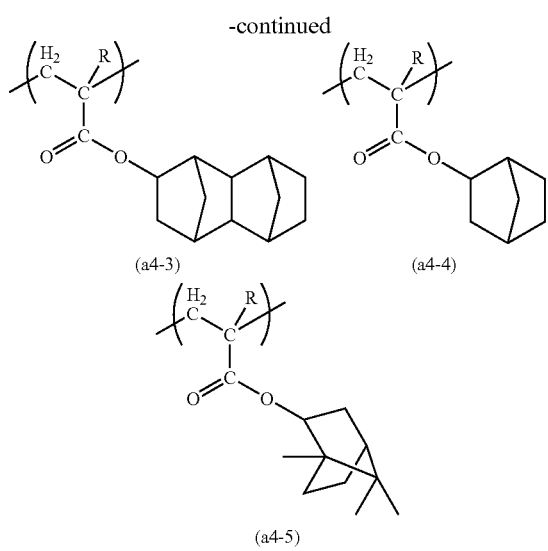

(a4-3) (a4-4)

(a4-5)

(In the formula, R is as defined above.)

When the structural unit (a4) is included in the component (A1), the amount of the structural unit (a4) is preferably within the range from 1 to 30 mol %, and more preferably from 10 to 20 mol %, based on the combined total of all the structural units that constitute the component (A1).

In the present invention, the component (A1) preferably includes a copolymer which contains the structural units (a1), (a2) and (a3). Examples of the copolymer include a copolymer consisting of the structural units (a1), (a2) and (a3); and a copolymer consisting of the structural units (a1), (a2), (a3) and (a4).

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). When a hydroxyalkyl group in which a part of the hydrogen atoms of the alkyl group has been substituted with fluorine atoms is introduced into a copolymer in this manner, the copolymer thus obtained can have an advantageous effect in reducing the levels of developing defects and LER (line edge roughness: non-uniform irregularities within the line side walls).

The weight average molecular weight (Mw) (the polystyrene equivalent value determined by gel permeation chromatography) of the component (A1) is not particularly limited, and is preferably 2,000 to 50,000, more preferably 3,000 to 30,000, and most preferably 5,000 to 20,000. By ensuring that the weight average molecular weight of the polymer compound (A1) is no more than the upper limit, solubility sufficient for a resist relative to a resist solvent can be obtained. By ensuring that it is no less than the lower limit, excellent dry-etching resistance and excellent sectional shape of the resist pattern can be obtained.

Furthermore, the dispersion degree (Mw/Mn) is preferably within a range of 1.0 to 5.0, more preferably 1.0 to 3.0, and most preferably 1.2 to 2.5. Herein, Mn represents the number average molecular weight.

[Component (A2)]

It is preferable that the component (A2) has a molecular weight within a range of 500 to less than 2000, and contains an acid dissociable, dissolution inhibiting group exemplified above in the component (A1) and a hydrophilic group. Specific examples thereof include compounds wherein a portion of the hydrogen atoms of the hydroxyl groups within a compound containing a plurality of phenol structures have been substituted with an aforementioned acid dissociable, dissolution inhibiting group.

The component (A2) is preferably low molecular weight phenol compounds known as sensitizers or heat resistance improvement agents for non-chemically amplified g-line or i-line resists in which a part of hydrogen atoms of hydroxyl groups are substituted with the above acid dissociable, dissolution inhibiting group, and can be used arbitrarily selected from those.

Examples of these low molecular weight phenol compounds include the following: Examples include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Of course, the low molecular weight phenol compounds are not restricted to these examples.

There is no particular restriction on the acid dissociable, dissolution inhibiting group, and examples thereof include those described above.

As the component (A), one kind can be used alone, or two or more kinds can be used in combination.

In the resist composition of the present invention, the content of the component (A) may be adjusted according to the thickness of the resist film to be formed.

<Component (B)>

The component (B) includes an acid generator (B1) represented by the general formula (B1-1) (hereinafter, sometimes referred to as component (B1)). The component (B1) is the same as the compound (B1) in the present invention.

As the component (B1), one kind can be used alone, or two or more kinds can be used in combination.

In the resist composition of the present invention, the amount of the component (B1) in the component (B) is preferably not less than 40% by weight, more preferably not less than 70% by weight, and may be 100% by weight. The amount of the component (B1) is most preferably 100% by weight. When the amount is not less than the lower limit of the above range, the lithography properties such as resolution, mask reproducibility, and line width roughness (LWR) can be improved in the formation of the resist pattern using the resist composition of the present invention.

In the component (B), an acid generator (B2) (hereinafter, referred to as component (B2)) other than the component (B1) may be used in combination with the component (B1).

There is no particular restriction on the component (B2) as long as it is a component other then the component (B1), and those proposed as acid generators for chemically-amplified resists can be used as the component (B2).

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzyl sulfonate-based acid generators; iminosulfonate-based acid generators; and disulfone-based acid generators.

As an onium salt-based acid generator, for example, an acid generator represented by a general formula (b'-1) or (b'-2) shown below can be used.

[Chemical Formula 45]

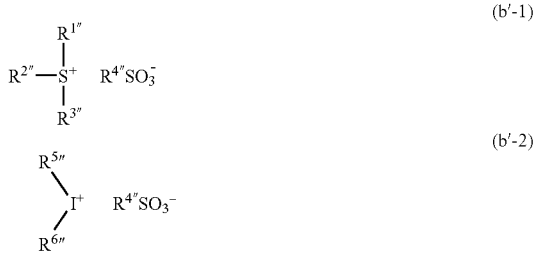

(wherein, $R^{1\prime\prime}$ to $R^{3\prime\prime}$, $R^{5\prime\prime}$ and $R^{6\prime\prime}$ each independently represents an aryl group or an alkyl group; two of $R^{1\prime\prime}$ to $R^{3\prime\prime}$ may mutually be bonded to form a ring together with the sulfur atom; $R^{4\prime\prime}$ represents a linear, branched, or cyclic alkyl group, or a linear, branched or cyclic fluorinated alkyl group; at least one of $R^{1\prime\prime}$ to $R^{3\prime\prime}$ represents an aryl group; and at least one of $R^{5\prime\prime}$ and $R^{6\prime\prime}$ represents an aryl group.)

In the formula (b'-1), $R^{1\prime\prime}$ to $R^{3\prime\prime}$ each independently represents an aryl group or an alkyl group. Here, two of $R^{1\prime\prime}$ to $R^{3\prime\prime}$ in the formula (b-1) may mutually be bonded to form a ring together with the sulfur atom in the formula.

Also, at least one of $R^{1\prime\prime}$ to $R^{3\prime\prime}$ represents an aryl group. Two or more of $R^{1\prime\prime}$ to $R^{3\prime\prime}$ are preferably aryl groups, and all of $R^{1\prime\prime}$ to $R^{3\prime\prime}$ are most preferably aryl groups.

There is no particular restriction on the aryl group for $R^{1\prime\prime}$ to $R^{3\prime\prime}$. For example, the aryl group is an aryl group of 6 to 20 carbon atoms, and a part of or all of hydrogen atoms in the aryl group may be substituted with an alkyl group, an alkoxy group, a halogen atom, a hydroxyl group and the like, or may not be substituted. The aryl group is preferably an aryl group of 6 to 10 carbon atoms because it can be synthesized inexpensively. Specific examples thereof include a phenyl group and a naphthyl group.

In the aryl group, the alkyl group with which hydrogen atoms may be substituted is preferably an alkyl group of 1 to 5 carbon atoms, and most preferably a methyl group, an ethyl group, a propyl group, an n-butyl group, and a tert-butyl group.

In the aryl group, the alkoxy group with which hydrogen atoms may be substituted is preferably an alkoxy group of 1 to 5 carbon atoms, and most preferably a methoxy group, an ethoxy group, an n-propoxy group, an iso-propoxy group, an n-butoxy group, and a tert-butoxy group.

In the aryl group, the alkoxy group with which hydrogen atoms may be substituted is preferably an alkoxy group of 1 to 5 carbon atoms, and most preferably a methoxy group and an ethoxy group.

In the aryl group, the halogen atom with which hydrogen atoms may be substituted is preferably a fluorine atom.

There is no restriction on the alkyl groups for $R^{1\prime\prime}$ to $R^{3\prime\prime}$. Examples thereof include a linear, branched, or cyclic alkyl group of 1 to 10 carbon atoms. The number of carbon atoms is preferably 1 to 5, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

Of these, it is most preferable that $R^{1\prime\prime}$ to $R^{3\prime\prime}$ each independently represents a phenyl group or a naphthyl group.

In the case that two of $R^{1\prime\prime}$ to $R^{3\prime\prime}$ in the formula (b'-1) are mutually bonded to form a ring together with the sulfur atom in the formula, it is preferable to form a 3- to 10-membered ring including the sulfur atom, and it is more preferable to form a 5- to 7-membered ring.

Also, in the case that two of $R^{1\prime\prime}$ to $R^{3\prime\prime}$ in the formula (b'-1) are mutually bonded to form a ring together with the sulfur atom in the formula, the other one of them is preferably an aryl group.

The aryl group is the same as those described above in the aryl group for $R^{1\prime\prime}$ to $R^{3\prime\prime}$.

$R^{4\prime\prime}$ represents a linear, branched or cyclic alkyl group, or a linear, branched or cyclic fluorinated alkyl group.

The number of carbon atoms in the linear or branched alkyl group for $R^{4\prime\prime}$ is preferably from 1 to 10, more preferably from 1 to 8, and most preferably from 1 to 4.

The cyclic alkyl group for $R^{4\prime\prime}$ is the same as the cyclic group described above in $R^{1\prime\prime}$. The number of carbon atoms in the cyclic alkyl group of $R^{4\prime\prime}$ is preferably from 4 to 15, more preferably from 4 to 10, and most preferably from 6 to 10.

The number of carbon atoms in the fluorinated alkyl group is preferably from 1 to 10, more preferably from 1 to 8, and most preferably from 1 to 4. Furthermore, the fluorination rate of the fluorinated alkyl group (proportion of fluorine atoms in the alkyl group) is preferably within a range from 10 to 100%, more preferably from 50 to 100%, and those wherein all hydrogen atoms are substituted with fluorine atoms (perfluoroalkyl groups) are particularly preferable, because the strength of the acid increases.

$R^{4\prime\prime}$ is most preferably a linear or cyclic alkyl group, or a linear or cyclic fluorinated alkyl group.

In the formula (b'-2), $R^{5\prime\prime}$ and $R^{6\prime\prime}$ each independently represents an aryl group or an alkyl group. At least one of $R^{5\prime\prime}$ and $R^{6\prime\prime}$ represents an aryl group. Both of $R^{5\prime\prime}$ and $R^{6\prime\prime}$ preferably represent aryl groups.

The aryl groups for $R^{5\prime\prime}$ and $R^{6\prime\prime}$ are the same as the aryl groups for $R^{1\prime\prime}$ to $R^{3\prime\prime}$.

The alkyl groups for $R^{5\prime\prime}$ and $R^{6\prime\prime}$ are the same as the alkyl group for $R^{1\prime\prime}$ to $R^{3\prime\prime}$.

Of these, it is most preferable that both of $R^{5\prime\prime}$ and $R^{6\prime\prime}$ be phenyl groups.

$R^{4\prime\prime}$ in the formula (b'-2) is the same as $R^{4\prime\prime}$ in the formula (b'-1).

Specific examples of the onium salt-based acid generator represented by the general formula (b'-1) and (b'-2) include diphenyliodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl) diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, diphenyl(1-(4-methoxy)naphthyl)sulfonium trifluoromethanesulfonate, heptafluoropropanesulfonate or nonafluorobutanesulfonate, and di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl) tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl) tetrahydropyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

Also, onium salts whose anion moiety is substituted with a methansulfonate, an n-propanesulfonate, an n-butanesulfonate, or an n-octanesulfonate can be used.

Furthermore, compounds in which the anion moiety within the above general formulas (b'-1) and (b'-2) has been substituted with an anion moiety represented by a general formula (b'-3) or (b'-4) shown below (wherein the cation moiety is the same as that shown in (b'-1) or (b'-2)) can also be used.

[Chemical Formula 46]

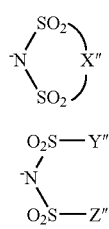

(b'-3)

(b'-4)

(wherein, X" represents an alkylene group of 2 to 6 carbon atoms in which at least one hydrogen atom is substituted with a fluorine atom; and Y" and Z" each independently represents an alkyl group of 1 to 10 carbon atoms in which at least one hydrogen atom is substituted with a fluorine atom.)

X" represents a linear or branched alkylene group in which at least one hydrogen atom is substituted with a fluorine atom. The number of carbon atoms in the alkylene group for X" is 2 to 6, preferably 3 to 5, and most preferably 3.

Y" and Z" each independently represents a linear or branched alkyl group in which at least one hydrogen atom is substituted with a fluorine atom. The number of carbon atoms in the alkyl group for Y" and Z" is 1 to 10, preferably 1 to 7, and more preferably 1 to 3.

Lower numbers of carbon atoms within the alkylene group for X" or the alkyl groups for Y" and Z" result in better solubility within the resist solvent, and are consequently preferred.

Furthermore, in the alkylene group for X" or the alkyl groups for Y" and Z", a higher number of hydrogen atoms that have been substituted with fluorine atoms results in increasing the strength of an acid and also improving the transparency relative to high energy light beams of 200 nm or less, or electron beams, and is consequently preferred. The proportion of fluorine atoms in the alkylene group or alkyl group, that is, the fluorination rate is preferably within a range from 70 to 100%, more preferably from 90 to 100%. A perfluoroalkylene group or a perfluoroalkyl group wherein all hydrogen atoms are substituted with fluorine atoms is most preferable.

Furthermore, a sulfonium salt that contains a cation moiety represented by a general formula (b'-5) or (b'-6) shown below can be used as an onium salt-based acid generator.

[Chemical Formula 47]

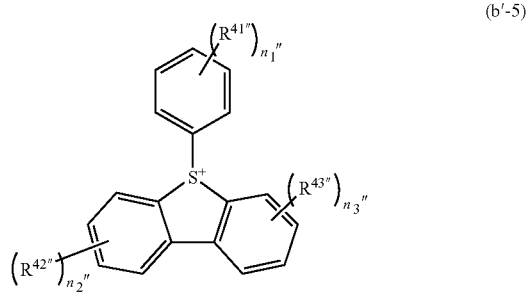

(b'-5)

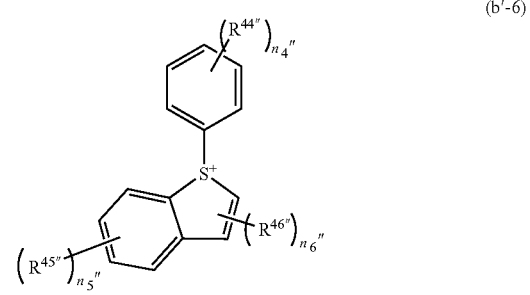

(b'-6)

(wherein, $R^{41''}$ to $R^{46''}$ each independently represents an alkyl group, an acetyl group, an alkoxy group, a carboxy group, a hydroxyl group, or a hydroxyalkyl group; $n_1''$ to $n_5''$ each independently represents an integer of 0 to 3; and $n_6''$ represents an integer of 0 to 2.)

The alkyl group for $R^{41''}$ to $R^{48''}$ is preferably an alkyl group of 1 to 5 carbon atoms. Of these, it is more preferably a linear or branched alkyl group, and still more preferably a methyl group, an ethyl group, a propyl group, an isopropyl group, an n-butyl group, or a tert-butyl group.

The alkoxy group for $R^{41\prime\prime}$ to $R^{46\prime\prime}$ is preferably an alkoxy group of 1 to 5 carbon atoms, more preferably a linear or branched alkoxy group, and particularly preferably a methoxy group or an ethoxy group.

The hydroxyalkyl group for $R^{41\prime\prime}$ to $R^{46\prime\prime}$ is preferably a group in which one or more hydrogen atoms in the alkyl group for $R^{41\prime\prime}$ to $R^{46\prime\prime}$ are substituted with hydrogen atoms, and examples thereof include a hydroxymethyl group, a hydroxyethyl group, and a hydroxypropyl group.

In the case that the symbols $n_1\prime\prime$ to $n_6\prime\prime$ on the bottom-right of $R^{41\prime\prime}$ to $R^{46\prime\prime}$ are an integer of two or more, a plurality of $R^{41\prime\prime}$ to $R^{46\prime\prime}$, respectively, may be the same or different.

$n_1\prime\prime$ is preferably 0 to 2, more preferably 0 or 1, and still more preferably 0.

It is preferable that $n_2\prime\prime$ and $n_3\prime\prime$ be each independently 0 or 1, and it is more preferable that $n_2\prime\prime$ and $n_3\prime\prime$ be 0.

$n_4\prime\prime$ is preferably 0 to 2, and more preferably 0 or 1.

$n_5\prime\prime$ is preferably 0 or 1, and more preferably 0.

$n_6\prime\prime$ is preferably 0 or 1, and more preferably 1.

There is no particular restriction on the anion moiety of the sulfonium salt containing the cation moiety represented by the formula (b'-5) or (b'-6), and the anion moiety may be the same as an anion moiety of onium salt-based acid generators which are conventionally suggested. Examples of such an anion moiety include fluorinated alkyl sulfonate ions such as the anion moiety $(R^{4\prime\prime}SO_3^-)$ of the onium salt-based acid generator represented by the general formula (b'-1) or (b'-2); and the anion moiety represented by the general formula (b'-3) or (b'-4). Of these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly preferable. Specific examples thereof include a trifluoromethylsulfonate ion, a heptafluoro-n-propylsulfonate ion, and a nonafluoro-n-butylsulfonate ion.

In the present specification, the term "oxime sulfonate-based acid generator" represents a compound which has at least one of the groups represented by a general formula (B2-1) shown below, and has a property that generates an acid upon exposure to radiation. These kinds of oxime sulfonate-based acid generators are widely used for a chemically-amplified resist composition, so any oxime sulfonate-based acid generator can be used, arbitrarily selected from these.

[Chemical Formula 48]

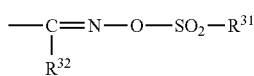

(B2-1)

(in the general formula (B2-1), $R^{31}$ and $R^{32}$ each independently represents an organic group.)

The organic group for $R^{31}$ or $R^{32}$ is a group containing carbon atoms, and may further contain atoms other than carbon atoms (for example, a hydrogen atom, an oxygen atom, a nitrogen atom, a sulfur atom and a halogen atom (a fluorine atom, a chlorine atom and the like)).

The organic group for $R^{31}$ is preferably a linear, branched or cyclic alkyl group or an aryl group. The alkyl group or aryl group may contain a substituent group. There is no particular restriction on the substituent group, and examples thereof include a fluorine atom, and a linear, branched or cyclic alkyl group of 1 to 6 carbon atoms. Here, the term "containing a substituent group" represents that a part or all of hydrogen atoms in the alkyl group or aryl group are substituted with substituent groups.

The number of carbon atoms in the alkyl group of $R^{31}$ is preferably 1 to 20, more preferably 1 to 10, still more preferably 1 to 8, still more preferably 1 to 6, and most preferably 1 to 4. The alkyl group for $R^{31}$ is particularly preferably an alkyl group which is partially or completely halogenated (hereinafter, sometimes referred to as a halogenated alkyl group). Here, a partially halogenated alkyl group represents an alkyl group in which a part of the hydrogen atoms is substituted with halogen atoms, and a completely halogenated alkyl group represents an alkyl group in which all of the hydrogen atoms are substituted with halogen atoms. Examples of the halogen atoms include a fluorine atom, a chlorine atom, a bromine atom and an iodine atom. Of these, a fluorine atom is preferable. That is, the halogenated alkyl group is preferably a fluorinated alkyl group.

The number of carbon atoms in the aryl group for $R^{31}$ is preferably 4 to 20, more preferably 4 to 10, and most preferably 6 to 10. The aryl group is particularly preferably an aryl group which is partially or completely halogenated. Here, a partially halogenated aryl group means an aryl group in which a part of the hydrogen atoms is substituted with halogen atoms, and a completely halogenated aryl group means an aryl group in which all of the hydrogen atoms are substituted with halogen atoms.

$R^{31}$ is particularly preferably an alkyl group of 1 to 4 carbon atoms containing no substituent group, or a fluorinated alkyl group of 1 to 4 carbon atoms.

The organic group for $R^{32}$ is preferably a linear, branched or cyclic alkyl group, an aryl group, or a cyano group. The alkyl group or the aryl group for $R^{32}$ is the same as those described above in the alkyl group or aryl group for $R^{31}$.

$R^{32}$ is particularly preferably a cyano group, an alkyl group of 1 to 8 carbon atoms containing no substituent group, or a fluorinated alkyl group of 1 to 8 carbon atoms.

The oxime sulfonate-based acid generator is more preferably a compound represented by a general formula (B2-2) or (B2-3) shown below.

[Chemical Formula 49]

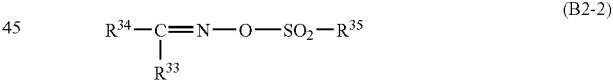

(B2-2)

(in the general formula (B2-2), $R^{33}$ represents a cyano group, an alkyl group containing no substituent group, or a halogenated alkyl group; $R^{34}$ represents an aryl group; and $R^{35}$ represents an alkyl group containing no substituent group, or a halogenated alkyl group.)

[Chemical Formula 50]

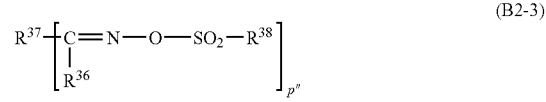

(B2-3)

(in the general formula (B2-3), $R^{36}$ represents a cyano group, an alkyl group containing no substituent group, or a halogenated alkyl group; $R^{37}$ represents a bivalent or trivalent aromatic hydrocarbon group; $R^{38}$ represents an alkyl group containing no substituent group or a halogenated alkyl group; and p" represents an integer of 2 or 3.)

In the general formula (B2-2), the number of carbon atoms in the alkyl group containing no substituent group or the halogenated alkyl group for $R^{33}$ is preferably 1 to 10, more preferably 1 to 8, and most preferably 1 to 6.

$R^{33}$ is preferably a halogenated alkyl group, and more preferably a fluorinated alkyl group.

The fluorinated alkyl group for $R^{33}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group; and heteroaryl groups in which a part of the carbon atoms which constitute the rings of these groups are substituted with heteroatoms such as an oxygen atom, a sulfur atom, and a nitrogen atom. Of these, a fluorenyl group is preferable.

The aryl group for $R^{34}$ may contain a substituent group such as an alkyl group of 1 to 10 carbon atoms, a halogenated alkyl group of 1 to 10 carbon atoms, and an alkoxy group of 1 to 10 carbon atoms. The number of carbon atoms of the alkyl group or halogenated alkyl group in the substituent group is preferably 1 to 8, and more preferably 1 to 4. Also, the halogenated alkyl group is preferably a fluorinated alkyl group.

The number of carbon atoms in the alkyl group containing no substituent group or the halogenated alkyl group for $R^{35}$ is preferably 1 to 10, more preferably 1 to 8, and most preferably 1 to 6.

$R^{35}$ is preferably a halogenated alkyl group, and more preferably a fluorinated alkyl group.

The fluorinated alkyl group for $R^{35}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated, because the strength of the generated acid increases. The fluorinated alkyl group for $R^{35}$ is most preferably a completely fluorinated alkyl group in which 100% of the hydrogen atoms are substituted with fluorine atoms.

In the general formula (B2-3), the alkyl group containing no substituent group or the halogenated alkyl group for $R^{36}$ is the same as those described above in the alkyl group containing no substituent group or the halogenated alkyl group for $R^{33}$.

Examples of the bivalent or trivalent aromatic hydrocarbon group for $R^{37}$ include aryl groups of $R^{34}$ in which one or two hydrogen atoms are further removed.

The alkyl group containing no substituent group or the halogenated alkyl group for $R^{38}$ is the same as those described above in the alkyl group containing no substituent group or the halogenated alkyl group for $R^{35}$.

p" is preferably 2.

Specific examples of the oxime sulfonate-based acid generator include

α-(p-toluenesulfonyloxyimino)-benzylcyanide,
α-(p-chlorobenzenesulfonyloxyimino)-benzylcyanide,
α-(4-nitrobenzenesulfonyloxyimino)-benzylcyanide,
α-(4-nitro-2-trifluoromethylbenzenesulfonyloxyimino)-benzylcyanide,
α-(benzenesulfonyloxyimino)-4-chlorobenzylcyanide,
α-(benzenesulfonyloxyimino)-2,4-dichlorobenzylcyanide,
α-(benzenesulfonyloxyimino)-2,6-dichlorobenzylcyanide,
α-(benzenesulfonyloxyimino)-4-methoxybenzylcyanide,
α-(2-chlorobenzenesulfonyloxyimino)-4-methoxybenzylcyanide,
α-(benzenesulfonyloxyimino)-thien-2-ylacetonitrile,
α-(4-dodecylbenzenesulfonyloxyimino)-benzylcyanide,
α-[(p-toluenesulfonyloxyimino)-4-methoxyphenyl]acetonitrile,
α-[(dodecylbenzenesulfonyloxyimino)-4-methoxyphenyl]acetonitrile,
α-(tosyloxyimino)-4-thienylcyanide,
α-(methylsulfonyloxyimino)-1-cyclopentenylacetonitrile,
α-(methylsulfonyloxyimino)-1-cyclohexenylacetonitrile,
α-(methylsulfonyloxyimino)-1-cycloheptenylacetonitrile,
α-(methylsulfonyloxyimino)-1-cyclooctenylacetonitrile,
α-(trifluoromethylsulfonyloxyimino)-1-cyclopentenylacetonitrile,
α-(trifluoromethylsulfonyloxyimino)-cyclohexylacetonitrile,
α-(ethylsulfonyloxyimino)-ethylacetonitrile,
α-(propylsulfonyloxyimino)-propylacetonitrile,
α-(cyclohexylsulfonyloxyimino)-cyclopentylacetonitrile,
α-(cyclohexylsulfonyloxyimino)-cyclohexylacetonitrile,
α-(cyclohexylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitrile,
α-(ethylsulfonyloxyimino)-1-cyclohexenylacetonitrile,
α-(isopropylsulfonyloxyimino)-1-cyclohexenylacetonitrile,
α-(n-butylsulfonyloxyimino)-1-cyclohexenylacetonitrile,
α-(methylsulfonyloxyimino)-phenylacetonitrile,
α-(methylsulfonyloxyimino)-p-methoxyphenylacetonitrile,
α-(trifluoromethylsulfonyloxyimino)-phenylacetonitrile,
α-(trifluoromethylsulfonyloxyimino)-p-methoxyphenylacetonitrile,
α-(ethylsulfonyloxyimino)-p-methoxyphenylacetonitrile,
α-(propylsulfonyloxyimino)-p-methylphenylacetonitrile, and
α-(methylsulfonyloxyimino)-p-bromophenylacetonitrile.

Also, oxime sulfonate-based acid generators disclosed in Japanese Unexamined Patent Application, First Publication No. Hei9-208554 ([Formula 18] and [Formula 19] in paragraphs [0012] to [0014]), and International Publication WO 2004/074242A2 (Examples 1 to 40 on pages 65 to 85) can be preferably used.

Further, suitable examples thereof include the following.

[Chemical Formula 51]

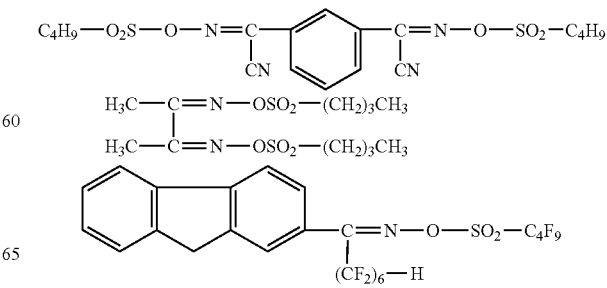

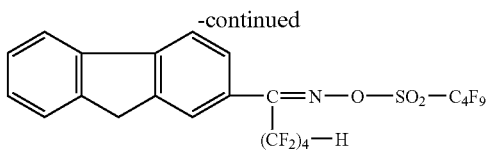

Among the diazomethane-based acid generators, specific examples of bisalkyl- or bisarylsulfonyldiazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Also, diazomethane-based acid generators disclosed in Japanese Unexamined Patent Application, First Publication No. Hei11-035551, Japanese Unexamined Patent Application, First Publication No. Hei11-035552, and Japanese Unexamined Patent Application, First Publication No. Hei11-035573 can be preferably used.

Examples of the poly(bissulfonyl)diazomethanes include
1,3-bis(phenylsulfonyldiazomethylsulfonyl)propane,
1,4-bis(phenylsulfonyldiazomethylsulfonyl)butane,
1,6-bis(phenylsulfonyldiazomethylsulfonyl)hexane,
1,10-bis(phenylsulfonyldiazomethylsulfonyl)decane,
1,2-bis(cyclohexylsulfonyldiazomethylsulfonyl)ethane,
1,3-bis(cyclohexylsulfonyldiazomethylsulfonyl)propane,
1,6-bis(cyclohexylsulfonyldiazomethylsulfonyl)hexane, and
1,10-bis(cyclohexylsulfonyldiazomethylsulfonyl)decane,
which are disclosed in Japanese Unexamined Patent Application, First Publication No. Hei11-322707.

As the component (B2), one kind selected from the above acid generators may be used alone, or two or more kinds may be used in combination.

The amount of the component (B) in the resist composition of the present invention is preferably within a range from 0.5 to 30 parts by mass, and more preferably from 1 to 20 parts by mass, relative to 100 parts by mass of the component (A). When the amount is within the range, a pattern can be sufficiently formed. Also, a uniform solution and excellent storage stability can be obtained. Therefore, an amount within the above range is preferable.

<Optional Components>

In order to improve the resist pattern shape and the post exposure stability of the latent image formed by the pattern-wise exposure of the resist layer, a nitrogen-containing organic compound (D) (hereinafter, referred to as component (D)) can be added to the resist composition as an optional component.

Since a multitude of these components (D) have already been proposed, any of these known compounds can be arbitrarily used. Of these, an aliphatic amine, particularly a secondary aliphatic amine or tertiary aliphatic amine is preferred. An aliphatic amine is an amine having one or more aliphatic groups, and the aliphatic groups preferably have 1 to 12 carbon atoms.

Examples of the aliphatic amine include an amine (alkylamine or alkylalcoholamine) wherein at least one of the hydrogen atoms of $NH_3$ is substituted with an alkyl or hydroxyalkyl group having 12 or less carbon atoms; and a cyclic amine.

Specific examples of the alkylamines or alkylalcoholamines include monoalkylamines such as n-hexylamine, n-heptylamine, n-octylamine, n-nonylamine, or n-decylamine; dialkylamines such as diethylamine, di-n-propylamine, di-n-heptylamine, di-n-octylamine, or dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, or tri-n-dodecylamine; and alkylalcoholamines such as diethanolamine, triethanolamine, diisopropanolamine, triisopropanolamine, di-n-octanolamine, or tri-n-octanolamine. Among these amines, trialkylamines, in which three alkyl groups of 5 to 10 carbon atoms are bonded with a nitrogen atom, are preferable, and tri-n-pentylamine is most preferable.

Examples of the cyclic amine include a heterocyclic compound containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amines include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These may be used either alone, or in combination of two or more different compounds.

The component (D) is typically used in a quantity within a range of 0.01 to 5.0 parts by weight, relative to 100 parts by weight of the component (A).

In the positive resist composition of the present invention, in order to prevent any deterioration in sensitivity, and improve the resist pattern shape and the post exposure stability of the latent image formed by the pattern-wise exposure of the resist layer, at least one compound (E) selected from the group consisting of organic carboxylic acids and phosphorus oxo acids or derivatives thereof (hereinafter, referred to as component (E)) can also be added as an optional component.

Suitable examples of organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly preferable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, phenylphosphonic acid, diphenyl phosphonate and dibenzyl phosphonate.

Examples of phosphinic acid derivatives include phosphinic esters such as phenylphosphinic acid.

As the component (E), one type may be used alone, or two or more types may be used in combination.

As the component (E), an organic carboxylic acid is preferable, and salicylic acid is particularly preferable.

The component (E) is used in a quantity within a range of 0.01 to 5.0 parts by weight, relative to 100 parts by weight of the component (A).

In the positive resist composition of the present invention, if desired, additives having miscibility, for example, additive resins for improving performance of a resist film, surfactants for improving coatability, dissolution inhibitors, plasticizers, stabilizers, colorants, antihalation agents, and dyes can be appropriately added.

<Organic Solvent (S)>

The resist composition of the present invention can be prepared by dissolving materials in an organic solvent (S) (hereinafter, sometimes referred to as component (S)).

The component (S) may be an organic solvent which can dissolve the respective components used in the present invention to give a uniform solution, and one or more kinds of organic solvents can be used, appropriately selected from those which have been conventionally known as a solvent for a chemically-amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, dipropylene glycol; derivatives of the polyhydric alcohols, including compounds having ester bonds such as ethylene glycol monoacetate, diethylene glycol monoacetate, propylene glycol monoacetate and dipropylene glycol monoacetate, and compounds having ether bonds such as monoalkyl ethers (for example, monomethyl ether, monoethyl ether, monopropyl ether and monobutyl ether) and monophenyl ether of the above polyhydric alcohols or the above compounds having ester bonds (of these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, ethyl ethoxypropionate; and aromatic organic solvents such as anisole, ethylbenzyl ether, cresylmethyl ether, diphenyl ether, dibenzyl ether, phenetole, butylphenyl ether, ethylbenzene, diethylbenzene, pentylbenzene, isopropylbenzene, toluene, xylene, cymene, and mesitylene.

These organic solvents may be used either alone, or as a mixed solvent of two or more different solvents.

Of these, propylene glycol monomethyl ether acetate (PGMEA), propylene glycol monomethyl ether (PGME) and EL are preferable.

Also, a mixed solvent obtained by mixing PGMEA and a polar solvent is preferable. The mixing ratio (mass ratio) of PGMEA to the polar solvent may be appropriately decided taking account of compatibility, and is preferably adjusted within a range from 1:9 to 9:1, and more preferably from 2:8 to 8:2.

More specifically, in the case of using EL as the polar solvent, the mass ratio PGMEA:EL is preferably from 1:9 to 9:1, and more preferably from 2:8 to 8:2. Furthermore, in those cases of using PGME as the polar solvent, the mass ratio PGMEA:PGME is preferably from 1:9 to 9:1, more preferably 2:8 to 8:2, and still more preferably 3:7 to 7:3.

Furthermore, as the component (S), mixed solvents of at least one of PGMEA and EL with γ-butyrolactone are also preferred. In such cases, the mass ratio of the former and latter components in the mixed solvents is preferably within a range from 70:30 to 95:5.

There is no particular restriction on the quantity of the component (S), and the quantity should be set in accordance with the required coating film thickness within a concentration that enables favorable application of the solution to a substrate or the like. Typically, the quantity is set so that the solid fraction concentration within the resist composition falls within a range from 2 to 20% by weight, and still more preferably from 5 to 15% by weight.

<<Method of Forming Resist Pattern>>

A method of forming a resist pattern of the present invention includes the steps of forming a resist film on a substrate using the resist composition described above, exposing the resist film, and developing the resist film to form a resist pattern.

The method of forming a resist pattern of the present invention can be performed, for example, in the following manner.

Namely, the resist composition described above is first applied to a substrate using a spinner or the like, a prebake is then conducted under temperature conditions of 80 to 150° C. for 40 to 120 seconds, preferably for 60 to 90 seconds, followed by selective exposure of the thus obtained film with an ArF exposure apparatus or the like, by irradiating ArF excimer laser light through a desired mask pattern, and then PEB (post exposure baking) is conducted under temperature conditions of 80 to 150° C. for 40 to 120 seconds, preferably for 60 to 90 seconds. Subsequently, a developing treatment is conducted using an alkali developing solution such as a 0.1 to 10% by mass aqueous solution of tetramethylammonium hydroxide (TMAH), preferably followed by rinsing with pure water, and drying. Also, according to circumstances, a bake treatment (post bake) may be conducted after the above developing treatment. In this manner, a resist pattern that is faithful to the mask pattern can be obtained.

The substrate is not specifically limited and a conventionally known substrate can be used. For example, substrates for electronic components, and such substrates having prescribed wiring patterns formed thereon can be exemplified. Specific examples thereof include a silicon wafer; a substrate made of a metal such as copper, chromium, iron and aluminum; and a substrate made of glass. As materials for the wiring pattern, for example, copper, aluminum, nickel and gold can be used.

Further, as the substrate, any one of the above-exemplified substrates provided with an inorganic and/or organic film on the surface thereof may be used. As the inorganic film, an inorganic anti-reflection film (inorganic BARC) can be exemplified. As the organic film, an organic anti-reflection film (organic BARC) can be exemplified.

There is no particular restriction on the wavelength used for the exposure, and the exposure can be conducted using radiation such as ArF excimer lasers, KrF excimer lasers, $F_2$ excimer lasers, extreme ultraviolet rays (EUV), vacuum ultraviolet rays (VUV), electron beams (EB), X-rays, and soft X-rays. The resist composition is effective for KrF excimer lasers, ArF excimer lasers, EB and EUV, and particularly effective for ArF excimer lasers.

The exposure of the resist film may be a usual exposure conducted in an inactive gas such as an air or a nitrogen gas (dry exposure), or may be an immersion exposure (liquid immersion lithography).

As described above, the immersion exposure is conventionally conducted under the condition where the region between a lens and a resist film on a wafer is filled with a solvent (immersion solvent) that has a larger refractive index than the refractive index of air.

More specifically, the immersion exposure is performed in the following manner. First, the region between the resist film obtained in the above manner and the lens at the lowermost point of the exposure apparatus is pre-filled with a solvent (immersion solvent) that has a larger refractive index than the refractive index of air, and then, keeping such a condition, the exposure (immersion exposure) is conducted through the desired mask pattern.

The immersion solvent is preferably a solvent that has a refractive index larger than the refractive index of air but smaller than the refractive index of the resist film exposed by the immersion exposure. There is no restriction on the refractive index of the immersion solvent, as long as the solvent has a refractive index within the above range.

Examples of the solvent which has a refractive index larger than that of air but smaller than that of a resist film include water, fluorine-based inactive liquid, a silicon-based solvent, and a hydrocarbon-based solvent.

Specific examples of the fluorine-based inactive liquid include a liquid which has a fluorine-based compound as a main component, such as $C_3HCl_2F_5$, $C_4F_9OCH_3$, $C_4F_9OC_2H_5$, and $C_5H_3F_7$. The fluorine-based inactive liquid preferably has a boiling point within a range from 70 to 180° C., and more preferably from 80 to 160° C. If the fluorine-based inactive liquid has a boiling point within the above range, the solvent used for the immersion exposure can be removed by a convenient method after exposure, and consequently it is preferable.

The fluorine-based inactive liquid is particularly preferably a perfluoroalkyl compound in which all hydrogen atoms of the alkyl groups are substituted with fluorine atoms. Examples of these perfluoroalkyl compounds include perfluoroalkylether compounds and perfluoroalkylamine compounds.

Specific examples of the perfluoroalkylether compounds include a perfluoro(2-butyl-tetrahydrofuran) (boiling point: 102° C.), and specific examples of the perfluoroalkylamine compounds include a perfluorotributylamine (boiling point: 174° C.).

The resist composition of the present invention is a novel resist composition which has not been known conventionally.

Also, according to the resist composition of the present invention, a resist pattern with excellent lithographic properties, such as more favorable resist shape, proximity effect, or mask error factor, can be formed Although the reason is not clear, it can be speculated as follows.

In the resist composition of the present invention, the anion moiety of the component (B1) used as an acid generator has a structure in which a bulky group including a polar group (such as —O—, —C(=O)—) is connected with the skeleton of "$Y^1$—$SO_3$—". Therefore, as compared with a fluorinated alkylsulfonate ion which has conventionally been used as an anion, the anion moiety of the present invention has high polarity and a sterically-bulky structure. It is speculated that, since the anion moiety of the present invention has the intermolecular interaction caused by high polarity and has the sterically-bulky structure, the diffusion of the anion moiety (acid) in the resist film can be suppressed as compared with an anion moiety of conventional acid generators such as nonafluorobutane sulfonate, and consequently, the diffusion of the acid generated in the exposed region toward the non-exposed region can be suppressed. Also, it is speculated that, since the cation moiety of the component (B1) contains a nitrogen atom, the component (B1) functions as a quencher which picks up an acid in the non-exposed region, and consequently, the diffusion of the acid generated in the exposed region toward the non-exposed region can further be suppressed. It is speculated that, by the synergistical action of those described above, the effect of suppressing the diffusion of the acid can be greatly improved, and thus lithography properties such as the mask reproducibility can be improved.

For the same reasons, it is also expected that the exposure margin (EL margin) can be improved. EL margin means the range of the exposure dose at which a resist pattern can be formed with a size which enables the variation for the target size to be kept within a prescribed range, when the exposure is performed changing the exposure dose. That is, EL margin means the range of the exposure dose at which a resist pattern faithful to the mask pattern can be obtained. The larger the value of the EL margin, the smaller the variation of the pattern size depending on the change in the exposure dose becomes, and the more the process margin can be improved. Consequently, a larger value of the EL margin is preferable.

Also, the alkyl chain of the alkylene group or fluorinated alkylene group for $Y^1$ has an excellent degradation property as compared with a perfluoroalkyl chain of 6 to 10 carbon atoms which is persistent (hardly-degradable), and thus it can be handled more safely in terms of the bioaccumulation potential.

EXAMPLES

Next, the present invention will be described in more detail with reference to examples, but the scope of the present invention is not limited to the following examples.

Example 1

A compound represented by the formula shown below was synthesized by the following procedure.

[Chemical Formula 52]

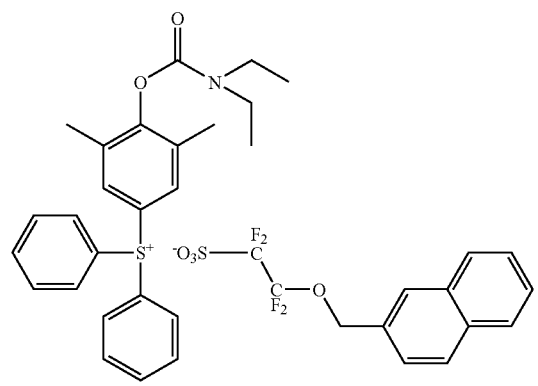

8.53 g of phosphorus oxide and 8.81 g of 2,5-dimethylphenol were gradually added into 60.7 g of methanesulfonic acid, which was controlled at 15° C. to 20° C. While the temperature was controlled at 15° C. to 20° C., the solution obtained above was matured for 30 minutes. Then, the temperature was raised up to 40° C., and the solution was matured for 2 hours. Subsequently, the reaction solution was dropwise added into 109.35 g of pure water which was cooled at 10 to 15° C. After the dropwise addition, 54.68 g of dichloromethane was added into the solution. Then, the solution obtained was stirred, and the dichloromethane layer was collected.

386.86 g of hexane with a temperature of 20 to 25° C. was prepared in another container, and the solution of the dichloromethane layer obtained above was dropwise added into it. After the dropwise addition, the solution was matured for 30 minutes at 20 to 25° C., and then filtratation was conducted, thereby obtaining 17.14 g of the intended compound (yield: 70.9%).

The obtained compound (hereinafter, referred to as compound (1)) was analyzed using $^1$H-NMR. The results are shown below.

$^1$H-NMR (solvent: DMSO-d6, 600 MHz): δ(ppm)=7.61-7.72 (m, 10H, Phenyl), 7.14 (s, 2H, H$^c$), 3.12 (s, 3H, H$^b$), 2.22 (s, 6H, H$^a$).

From the results described above, it could be confirmed that the compound (1) had a structure shown below.

[Chemical Formula 53]

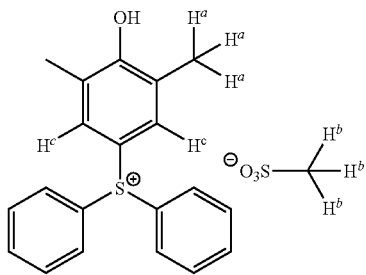

Subsequently, 20.06 g of the compound (1) was dissolved in 300.9 mL of tetrahydrofuran (THF). Iit was confirmed that the compound (1) was dissolved, then 60% concentration of sodium hydroxide (5.18 g) was added into the solution, and the solution obtained was stirred for 30 minutes. Subsequently, a solution of THF (32.4 mL) with diethylcarbamoyl chloride (16.21 g) was added. After the solution was reacted for 20 hours at 65° C., the reaction was stopped by addition of pure water (300 g). A separating treatment was conducted three times using 300 g of tert-butyl methyl ether (TBME) and pure water, and a water layer was recovered. Then, the water layer was dried, thereby obtaining 25 g of the intended compound (yield: 82%, purity 76%).

The obtained compound (hereinafter, referred to as compound (2)) was analyzed using $^1$H-NMR. The results are shown below.

$^1$H-NMR (solvent: DMSO-d6, 400 MHz): δ (ppm)=7.76-7.84 (m, 10H, Phenyl), 7.66 (s, 2H, H$^c$), 3.29-3.47 (qq, 4H, H$^e$), 2.32 (s, 3H, H$^b$), 2.18 (s, 6H, H$^a$), 1.09-1.25 (tt, 6H, H$^d$).

From the results described above, it could be confirmed that the compound (2) had a structure shown below.

[Chemical Formula 54]

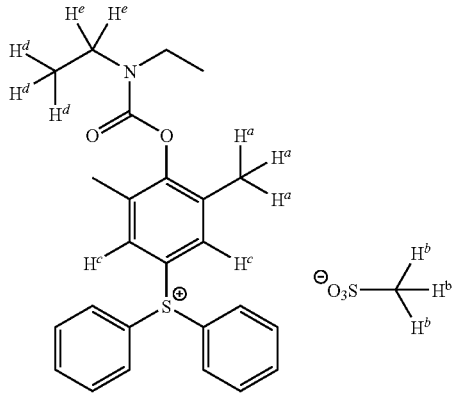

Separately, 6.7 mL of tetrahydrofuran was added into 5.0 g of 2-naphthylmethyloxytetrafluoroethanesulfonylfuloride, and then an aqueous solution of lithium hydroxide (0.98 g) dissolved in 13.6 mL of pure water was dropwise added. Then, it was stirred in an ice bath. As no absorption of $^{19}$F—NMR at -217.6 ppm by —SO$_2$F was observed, it was confirmed that all fluorinated sulfonyl groups were changed to lithium sulfonate. Subsequently, the reaction solution was concentrated and dried, thereby obtaining a white viscous solid. The crude product thus obtained was dissolved in 14.2 ml of acetone, and filtered in order to remove LiF obtained as a by-product. Subsequently, the filtrate was concentrated, thereby obtaining 5.50 g of a compound (3) represented by a general formula (3) shown below.

[Chemical Formula 55]

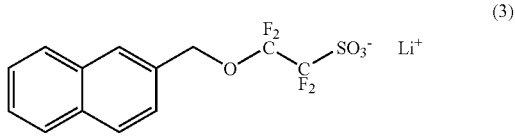

(3)

Next, the compound (2) (4.9 g, purity: 76%) was dissolved in pure water (70 g). 70 g of dichloromethane was added therein, and then the compound (3) (3.0 g) was gradually added. Thereafter, the solution was stirred for 1 hour at 25° C. After the reaction was finished, dichloromethane solution was washed with water, and then it was concentrated to dryness. The powder thus obtained was dispersively washed with hexane, and then it was dried under reduced pressure, thereby obtaining 5.41 g of the intended compound (yield: 94%)

The obtained compound (hereinafter, referred to as compound (b1-11)) was analyzed using $^1$H-NMR. The results are shown below.

$^1$H-NMR (solvent: DMSO-d6, 400 MHz): δ (ppm)=7.76-7.97 (m, 14H, Phenyl+Naphthyl), 7.66 (s, 2H, H$^c$), 7.52-7.55 (m, 3H, Naphthyl), 5.20 (s, 3H, Naphthyl), 3.29-3.47 (qq, 4H, H$^e$), 2.32 (s, 3H, H$^b$), 2.18 (s, 6H, H$^a$), 1.09-1.25 (tt, 6H, H$^d$).

From the results described above, it could be confirmed that the compound (b1-11) had a structure shown below.

[Chemical Formula 56]

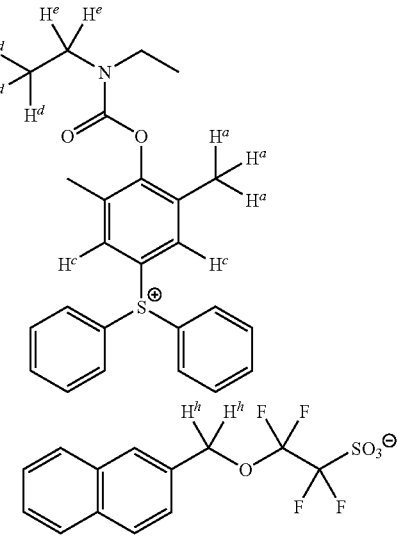

Comparative Synthesis Example 1

A compound represented by the formula shown below was synthesized by the following procedure.

[Chemical Formula 57]

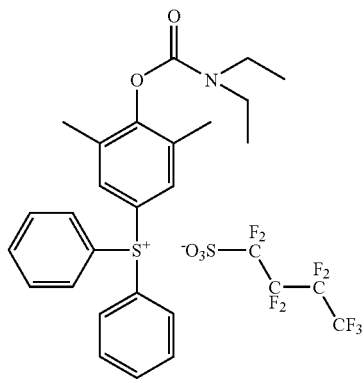

3 g of the compound (2) was dissolved in 47 g of pure water. 47 g of dichloromethane was added therein, and 2.22 g of potassium perfluoro-n-butanesulfonate was gradually added, and then the solution obtained was stirred for 1 hour at 25° C. After the reaction was finished, dichloromethane solution was washed with water, and then it was concentrated to dryness. The powder thus obtained was dispersively washed with hexane, and then it was dried under reduced pressure, thereby obtaining 3.19 g of the intended compound (yield: 97.8%). The compound thus obtained is referred to as compound (3).

The compound (3) was analyzed by $^1$H-NMR and $^{19}$F-NMR. The results are shown below.

$^1$H-NMR (solvent: DMSO-d6, 400 MHz): δ (ppm)=7.76-7.97 (m, 10H, Phenyl), 7.66 (s, 2H, H$^c$), 3.29-3.47 (qq, 4H, H$^e$), 2.18 (s, 6H, H$^a$), 1.09-1.25 (tt, 6H, H$^d$).

$^{19}$F-NMR (DMSO-d6, 376 MHz): δ (ppm)=−77.7, −111.9, −118.5, −122.9.

From the results described above, it could be confirmed that the compound (3) had a structure shown below.

[Chemical Formula 58]

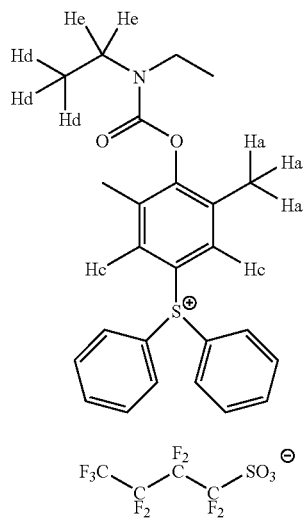

Example 2

A compound represented by the formula shown below was synthesized by the following procedure.

[Chemical Formula 59]

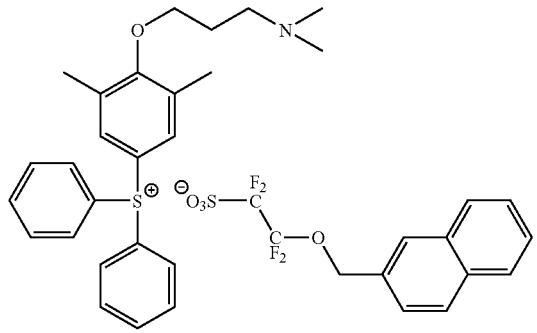

25.76 g of 2,6-dimethylphenol and 500 g of acetone were added in a three-neck flask, and 145.6 g of potassium carbonate was added therein. After the above solution was stirred for 30 minutes, 133.2 g of 1-chloro-3-dimethylaminopropane was added, and further 23.32 g of potassium iodide was added therein. Then, the reaction was conducted for 19 hours under reflux with acetone. The reaction solution was cooled to room temperature, and filtration was conducted. The filtrate obtained by the filtration was dried. 333 g of pure water and 333 g of TBME (tert-butyl methyl ether) were added to the solid thus obtained, and the TBME layer was collected by a separation method. Further, 10% HCl (92.8 g) solution was added into the solution of TBME layer, and then the water layer was collected by a separation method. Thereafter, the solution thus obtained was washed twice using TBME (92.8 g). Subsequently, 10% NaOH (112.2 g) aqueous solution and TBME (92.8 g) were added therein, and the TBME layer was collected by a separation method. Thereafter, the solution thus obtained was washed four times using pure water (92.68 g). The TBME layer thus obtained was concentrated, and dried with a vacuum pump, thereby obtaining 22.01 g of the intended compound (yield: 50.3%).

The obtained compound (hereinafter, referred to as compound (4)) was analyzed using $^1$H-NMR. The results are shown below.

$^1$H-NMR (solvent: DMSO-d6, 400 MHz): δ (ppm)=1.85 (t, 2H, H$^b$), 2.03-2.78 (m, 6H, H$^a$, m, 6H, H$^e$), 2.40 (m, 2H, H$^c$), 3.71 (t, 2H, H$^d$), 6.87 (t, 1H, H$^g$), 6.96 (d, 2H, H$^f$).

From the results described above, it could be confirmed that the compound (4) had a structure shown below.

[Chemical Formula 60]

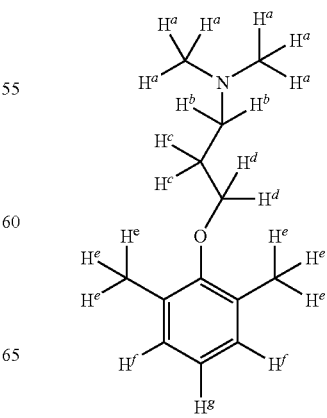

Next, while 43.0 g of methanesulfonic acid was stirred, 5.45 g of diphosphorus pentaoxide was added therein, and then a methanesulfonic acid solution (28.9 wt %, 26.9 g) of the compound (4) (9.55 g) and diphenylsulfoxide was gradually added therein while being cooled with ice. Thereafter, the above solution was stirred for 18 hours at room temperature, and then the reaction solution was dropwise added into a mixture solvent of pure water (261.7 g) and TBME (523.5 g) slowly. The water layer was collected by a separation method, and washed three times with 523.5 g of dichloromethane. Thereafter, 30 wt % NaOH aqueous solution (136.6 g) was dropwise added therein slowly. Then, the solution was further washed three times with 136.6 g of TBME, followed by conducting an extraction treatment three times with 398.3 g of dichloromethane. The dichloromethane layer thus obtained was concentrated, thereby obtaining the intended compound (20.2 g) as a viscous solid.

The obtained compound (hereinafter, referred to as compound (5)) was analyzed using $^1$H-NMR.

$^1$H-NMR (solvent: DMSO-d6, 400 MHz): δ (ppm)=1.86 (t, 2H, H$^b$), 2.07-2.23 (m, 6H, H$^a$), 2.24-2.35 (m, 6H, H$^e$, m, 3H, H$^h$), 2.40 (m, 2H, H$^c$), 3.87 (t, 2H, H$^d$), 7.60 (s, 2H, H$^f$), 7.75-7.86 (m, 10H, Phenyl).

From the results described above, it could be confirmed that the compound (5) had a structure shown below.

[Chemical Formula 61]

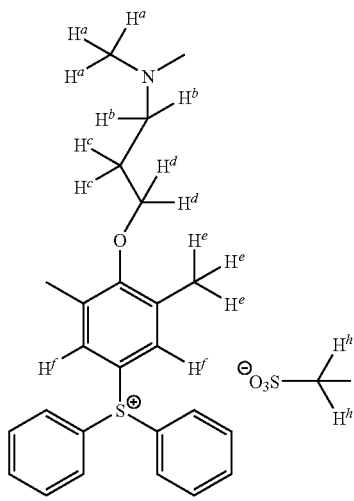

25.1 g of pure water and 62.8 g of dichloromethane were added into 3.70 g of 2-naphthylmethyloxytetrafluoroethanesulfonylfluoride. 16.6 wt % aqueous compound (5) solution (37.7 g) was added therein, and the solution thus obtained was stirred at room temperature for 2 hours. Thereafter, the organic layer was collected by a separation method, and washed four times with pure water (62.8 g). Then, the solvent was distilled away under reduced pressure, thereby obtaining the intended compound (7.00 g).

The compound thus obtained (hereinafter, referred to as compound (b1-12)) was analyzed by $^1$H-NMR and $^{19}$F-NMR.

$^1$H-NMR (solvent: DMSO-d6, 400 MHz): δ (ppm)=1.86 (t, 2H, H$^b$), 2.12 (m, 6H, H$^a$), 2.27 (m, 6H, H$^e$), 2.40 (m, 2H, H$^c$), 3.85 (t, 2H, H$^d$), 5.18 (s, 2H, H$^h$), 7.75-7.62 (m, 15H, H$^h$, H$^i$), 7.73-7.96 (m, 14H, Phenyl, H$^j$).

$^{19}$F-NMR (DMSO-d6, 376 MHz): δ (ppm)=−113.4 (t, 2F, F$^a$), −80.3 (t, 2F, F$^b$).

From the results described above, it could be confirmed that the compound (b1-12) had a structure shown below.

[Chemical Formula 62]

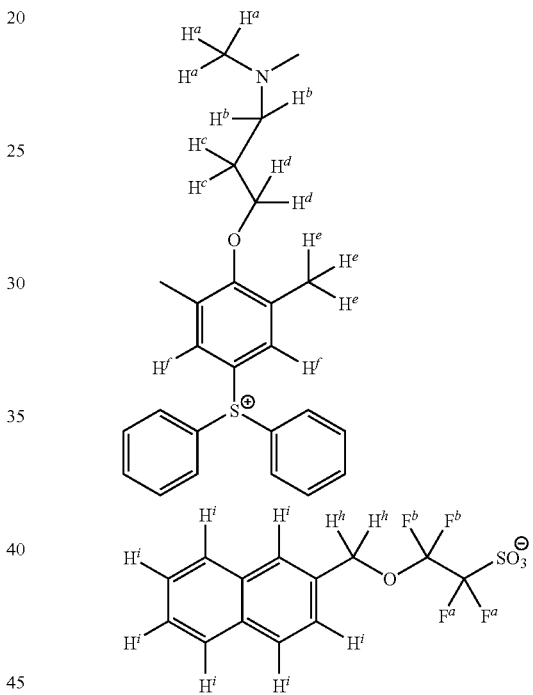

Examples 3 to 5, and Comparative Examples 1 to 3

Each component shown in Table 1 was mixed and dissolved, thereby preparing a positive resist composition.

TABLE 1

|  | Component (A) | Component (B) |  | Component (D) | Component (E) | Component (S) | |
|---|---|---|---|---|---|---|---|
| Example 3 | (A)-1 | (B)-1 |  | (D)-1 | (E)-1 | (S)-1 | (S)-2 |
|  | [100] | [10.32] |  | [1.2] | [1.32] | [2380] | [10] |
| Comparative Example 1 | (A)-1 | (B)-2 |  | (D)-1 | (E)-1 | (S)-1 | (S)-2 |
|  | [100] | [9.79] |  | [1.2] | [1.32] | [2380] | [10] |
| Comparative Example 2 | (A)-1 | (B)-3 |  | (D)-1 | (E)-1 | (S)-1 | (S)-2 |
|  | [100] | [8.0] |  | [1.2] | [1.32] | [2380] | [10] |
| Example 4 | (A)-1 | (B)-3 | (B)-4 |  | (E)-1 | (S)-1 | (S)-2 |
|  | [100] | [6.00] | [1.93] |  | [0.73] | [2200] | [10] |
| Example 5 | (A)-1 | (B)-3 | (B)-4 |  | (E)-1 | (S)-1 | (S)-2 |
|  | [100] | [6.00] | [3.85] |  | [0.73] | [2200] | [10] |

TABLE 1-continued

|  | Component (A) | Component (B) | Component (D) | Component (E) | Component (S) | |
|---|---|---|---|---|---|---|
| Comparative Example 3 | (A)-1 [100] | (B)-3 [6.00] | (D)-1 [0.60] | (E)-1 [0.73] | (S)-1 [2200] | (S)-2 [10] |

(A)-1: the copolymer represented by a general formula (A)-1 shown below (Mw = 7,000; Mw/Mn = 1.8) (in the formula, l:m:n = 45:35:20 (molar ratio))
(B)-1: the above compound (b1-11)
(B)-2: the above compound (3)
(B)-3: 4-methylphenyldiphenylsulfonium nonafluoro-n-butanesulfonate
(B)-4: the above compound (b1-12)
(D)-1: tri-n-pentylamine
(E)-1: salicylic acid
(S)-1: a mixture solvent of PGMEA/PGME = 6/4 (mass ratio)
(S)-2: γ-butyrolactone Here, 10.32 parts by weight of the compound (B)-1, 9.79 parts by weight of the compound (B)-2, and 8.0 parts by weight of the compound (B)-3 are equimolar amounts.

[Chemical Formula 63]

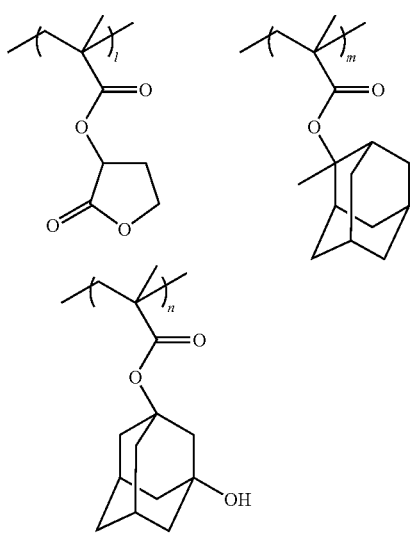

(A)-1

Resist patterns were formed by the following procedure using the resist composition solutions thus obtained, and lithography properties were evaluated.

[Resolution and Sensitivity]

An organic anti-reflection film composition (product name: "ARC29", manufactured by Brewer Science Ltd.) was applied onto an 8-inch silicon wafer using a spinner, and the composition was then baked at 205° C. for 60 seconds to be dried, thereby forming an organic anti-reflection film having a film thickness of 82 nm. Each positive resist composition solution obtained above in Examples 3 to 5, and Comparative Examples 1 to 3 was uniformly applied onto the antireflection film using a spinner, followed by conducting a prebake (PAB) treatment on a hot plate at 100° C. for 60 seconds and then conducting a drying treatment, thereby forming a resist film having a film thickness of 150 nm.

Subsequently, the obtained resist film was selectively exposed by an ArF excimer laser (193 nm), using an ArF exposure apparatus "NSR-S302" (manufactured by Nikon; numerical aperture (NA)=0.60, ⅔ annual illumination) through a mask pattern (6% half tone).

Thereafter, a post exposure baking (PEB) treatment was conducted at 110° C. for 60 seconds, followed by a developing treatment for 30 seconds at 23° C. in a 2.38 weight % aqueous solution of tetramethylammonium hydroxide (TMAH) (product name: "NMD-3", manufactured by Tokyo Ohka Kogyo Co., Ltd.). Then, the resist film was rinsed with pure water for 30 seconds, and dried by shaking.

As a result, in all of the examples, a line and space (L/S) pattern was formed with a line width of 120 nm and a pitch of 240 nm on the resist film.

Here, an optimum exposure "Eop" (mJ/cm$^2$; sensitivity) for forming a line and space pattern with a line width of 120 nm and a pitch of 240 nm was determined The results are shown in Table 2.

[Evaluation of Resist Pattern Shape]

Using the above Eop, a trench pattern with a space width of 140 nm and a pitch of 1540 nm was formed as a target. A cross-sectional shape of the resist pattern thus formed was observed using a scanning electron microscope (SEM) "S4500" (manufactured by Hitachi, Ltd.). The results were evaluated based oh the criterion described below, and the evaluated results are shown in Table 2.

(Criterion)
A: High rectangularity
B: Low rectangularity (top of the pattern is rounded)

[Proximity Effect]

Proximity effect (nm) in the above trench pattern was computed by a following formula. Here, it is more preferable if the proximity effect (nm) is smaller.

Proximity effect (nm)=[mask size of trench pattern (nm)]−[space width of trench pattern (nm)]

Furthermore, when the proximity effect (nm) of comparative example 2 was used as the standard (set to 100%), the percentage (%) (referred to as "proximity effect (%)") which shows how much the proximity effect (nm) of example 2 or comparative example 1 was improved as compared with the proximity effect (nm) of comparative example 2 was computed by a following formula. The results are shown in Table 2. Here, a larger value of the proximity effect (%) shows that the proximity effect is more improved, as compared with comparative example 2.

Proximity effect (%)=100+[1−((proximity effect (nm) of example 2 or comparative example 1)/(proximity effect (nm) of comparative example 2)×100]

[Mask Error Factor (MEF)] 1:1.2 of 120, 1:1 of 130

Using each optimum exposure (Eop) of examples 4 and 5, and comparative example 2, a L/S pattern (line and space pattern) with a pitch of 240 nm was formed by using a mask pattern with a line width of 120 nm or 130 nm as a target size.

Here, a plurality of points was plotted on a graph, based on the target size (nm) as the abscissa axis and a line width (nm) of the L/S pattern formed on the resist film by using each mask pattern as the longitudinal axis. Then, a slope of a straight line which connects the plotted points was computed as the MEF. The closer to 1 the value of MEF (the slope of the straight line), the better the mask reproducibility becomes. The results are shown in Table 2.

TABLE 2

| | Example 3 | Comparative Example 1 | Comparative Example 2 | Example 4 | Example 5 | Comparative Example 3 |
|---|---|---|---|---|---|---|
| Eop (mJ/cm$^2$) | 44.5 | 37.1 | 31.2 | 21.6 | 35.8 | 24.5 |
| Pattern shape | A | B | B | A | A | B |
| Proximity effect (%) | 112.7 | 94.0 | 100 | — | — | — |
| MEF | — | — | — | 1.56 | 1.91 | 2.23 |

From the above results, it is confirmed that lithography properties are excellent in the case of using the compound of the present invention.

INDUSTRIAL APPLICABILITY

According to the present invention, there can be provided a novel compound useful as an acid generator for a resist composition, an acid generator, a resist composition, and a method of forming a resist pattern.

The invention claimed is:

1. A resist composition comprising a base component (A) which exhibits changed solubility in an alkali developing solution under action of acid, and an acid generator component (B) which generates an acid upon exposure, wherein
the acid generator component (B) comprises an acid generator (B1) represented by a general formula (B1-1) shown below:

[Chemical Formula 1]

(B1-1)

$$R^X-Q^1-O-\left[\overset{O}{\underset{\|}{C}}\right]_n-Y^1-SO_3^- \; A^+$$

(wherein, $R^X$ represents a hydrocarbon group which may contain a substituent group; $Q^1$ represents an alkylene group of 1 to 12 carbon atoms which may contain a substituent group, or a single bond; n represents an integer of 0 or 1; $Y^1$ represents an alkylene group of 1 to 4 carbon atoms or a fluorinated alkylene group of 1 to 4 carbon atoms; and $A^+$ represents an organic cation which contains a nitrogen atom), and
said $A^+$ in the general formula (B1-1) comprises a group represented by a general formula (I) shown below:

[Chemical Formula 2]

(I)

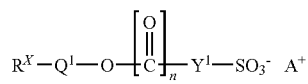

(in the formula, $W^1$ represents an oxygen atom or a sulfur atom; $Q^2$ represents an alkylene group or a single bond; and $R^7$ and $R^8$ each independently represents a hydrogen atom, an alkyl group which may contain a substituent group, an aliphatic cyclic group which may contain a substituent group, or an aromatic cyclic group which may contain a substituent group, wherein $R^7$ and $R^8$ may mutually be bonded to form a ring).

2. The resist composition according to claim 1, wherein the acid generator (B1) is composed of a compound represented by a general formula (B1-1-1) shown below:

[Chemical Formula 3]

(B1-1-1)

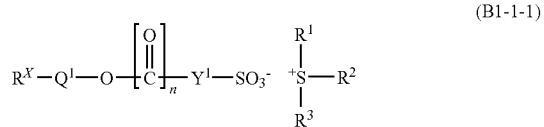

(wherein, $R^X$, $Q^1$, n, and $Y^1$ are as defined above; $R^1$ to $R^3$ each independently represents an aryl group which may contain a substituent group, or an alkyl group which may contain a substituent group, at least one of $R^1$ to $R^3$ represents an aryl group, and at least one of $R^1$ to $R^3$ contains a substituent group represented by a general formula (I-1) shown below; alternatively, $R^1$ and $R^2$ are mutually bonded to form a ring together with the sulfur ion in the formula, $R^3$ represents an aryl group which may contain a substituent group, an alkyl group which may contain a substituent group, or a group of —$R^4$—C(=O)—$R^5$ (wherein, $R^4$ represents an alkylene group of 1 to 5 carbon atoms, and $R^5$ represents an aryl group which may contain a substituent group), and one or both of the ring and $R^3$ contain a substituent group represented by a general formula (I-1) shown below)

[Chemical Formula 4]

(I-1)

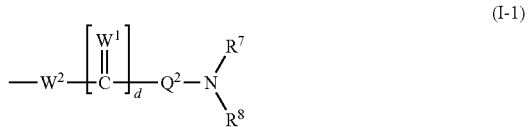

(wherein, $W^1$, $Q^2$, $R^7$, and $R^8$ are as defined above; $W^2$ represents a bivalent linking group; and d represents an integer of 0 or 1).

3. The resist composition according to claim 1, wherein the base component (A) is a base component which exhibits increased solubility in an alkali developing solution under action of acid.

4. The resist composition according to claim 3, wherein the base component (A) comprises a resin component (A1) which exhibits increased solubility in an alkali developing solution under action of acid, and the resin component (A1) comprises a structural unit (a1) derived from an acrylate ester which has an acid dissociable, dissolution inhibiting group.

5. The resist composition according to claim 4, wherein the resin component (A1) further comprises a structural unit (a2) derived from an acrylate ester which has a lactone-containing cyclic group.

6. The resist composition according to claim 4, wherein the resin component (A1) further comprises a structural unit (a3) derived from an acrylate ester which has a polar group-containing aliphatic hydrocarbon group.

7. The resist composition according to claim 5, wherein the resin component (A1) further comprises a structural unit (a3) derived from an acrylate ester which has a polar group-containing aliphatic hydrocarbon group.

8. A method of forming a resist pattern comprising: forming a resist film on a substrate using the positive resist composition according to any one of claims 1 and 2 to 7; exposing the resist film; and developing the resist film to form a resist pattern.

9. A compound represented by a general formula (B1-1) shown below:

[Chemical Formula 5]

(B1-1)

$$R^X-Q^1-O-\left[\overset{O}{\underset{\|}{C}}\right]_n-Y^1-SO_3^-\ A^+$$

(wherein, $R^X$ represents a hydrocarbon group which may contain a substituent group; $Q^1$ represents an alkylene group of 1 to 12 carbon atoms which may contain a substituent group, or a single bond; n represents an integer of 0 or 1; $Y^1$ represents an alkylene group of 1 to 4 carbon atoms or a fluorinated alkylene group of 1 to 4 carbon atoms; and $A^+$ represents an organic cation which contains a nitrogen atom), and said $A^+$ in the general formula (B1-1) comprises a group represented by a general formula (I) shown below:

[Chemical Formula 6]

(I)

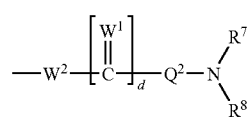

(in the formula, $W^1$ represents an oxygen atom or a sulfur atom; $Q^2$ represents an alkylene group or a single bond; and $R^7$ and $R^8$ each independently represents a hydrogen atom, an alkyl group which may contain a substituent group, an aliphatic cyclic group which may contain a substituent group, or an aromatic cyclic group which may contain a substituent group, wherein $R^7$ and $R^8$ may mutually be bonded to form a ring).

10. The compound according to claim 9, wherein the compound (B1-1) is a compound represented by a general formula (B1-1-1) shown below:

[Chemical Formula 7]

(B1-1-1)

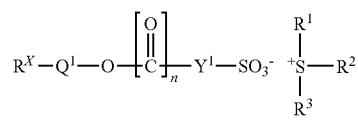

(wherein, $R^X$, $Q^1$, n, and $Y^1$ are as defined above; $R^1$ to $R^3$ each independently represents an aryl group which may contain a substituent group, or an alkyl group which may contain a substituent group, at least one of $R^1$ to $R^3$ represents an aryl group, and at least one of $R^1$ to $R^3$ contains a substituent group represented by a general formula (I-1) shown below; alternatively, $R^1$ and $R^2$ are mutually bonded to form a ring together with the sulfur ion in the formula, $R^3$ represents an aryl group which may contain a substituent group, an alkyl group which may contain a substituent group, or the group $-R^4-C(=O)-R^5$ (wherein, $R^4$ represents an alkylene group of 1 to 5 carbon atoms, and $R^5$ represents an aryl group which may contain a substituent group), and one or both of the ring and $R^3$ contain a substituent group represented by a general formula (I-1) shown below)

[Chemical Formula 8]

(I-1)

$$-W^2-\left[\overset{W^1}{\underset{\|}{C}}\right]_d-Q^2-N\overset{R^7}{\underset{R^8}{\diagup}}$$

(wherein, $W^1$, $Q^2$, $R^7$, and $R^8$ are as defined above; $W^2$ represents a bivalent linking group; and d represents an integer of 0 or 1).

11. An acid generator which consists of a compound according to claim 9 or 10.

* * * * *